US007417054B2

(12) United States Patent
Carruthers et al.

(10) Patent No.: US 7,417,054 B2
(45) Date of Patent: Aug. 26, 2008

(54) NAPHTHYRIDINE COMPOUNDS

(75) Inventors: Nicholas I. Carruthers, Poway, CA (US); John M. Keith, San Diego, CA (US); Michael A. Letavic, San Diego, CA (US); Chandravadan R. Shah, San Diego, CA (US)

(73) Assignee: Janssen Pharmaceutica N.V. (BG)

( * ) Notice: Subject to any disclaimer, the term of this patent is extended or adjusted under 35 U.S.C. 154(b) by 258 days.

(21) Appl. No.: 11/424,751

(22) Filed: Jun. 16, 2006

(65) Prior Publication Data
US 2006/0287292 A1 Dec. 21, 2006

Related U.S. Application Data

(60) Provisional application No. 60/692,003, filed on Jun. 17, 2005.

(51) Int. Cl.
*A01N 43/42* (2006.01)
*A61K 31/44* (2006.01)
*C07D 471/02* (2006.01)
(52) U.S. Cl. .................................. 514/300; 546/122
(58) Field of Classification Search .............. 546/122; 514/300
See application file for complete search history.

(56) References Cited

U.S. PATENT DOCUMENTS

| 4,113,869 | A | 9/1978 | Gardner |
| 2006/0194837 | A1 | 8/2006 | Carruthers |

FOREIGN PATENT DOCUMENTS

| EP | 0978512 A1 | 2/2000 |
| EP | 1113007 A1 | 7/2001 |
| GB | 1335261 A1 | 10/1973 |
| WO | 9640142 | * 12/1996 |
| WO | WO 01/32624 | 5/2001 |
| WO | WO 2005/111036 A1 | 11/2005 |

OTHER PUBLICATIONS

PCT Search Report for PCT/US2006/023788 dated Nov. 15, 2006.
U.S. Appl. No. 11/424,734, filed Jun. 16, 2006, Apodaca.
Alves-Rodrigues, A. et al. Pharmacological Characterisation of the Histamine $H_3$ Receptor in the Rat Hippocampus. *Brain Res.* 1998, 788(1-2), 179-186.
Arrang, J.-M. et al. Auto-Inhibition of Brain Histamine Release by a Novel Class ($H_3$) of Histamine Receptor. *Nature* (London) 1983, 302(5911), 832-837.
Berge, S.M. et al. Pharmaceutical Salts. *J. Pharm. Sci.*, 1977, 66:1-19.
Blandizzi, C. et al. Histamine $H_3$ Receptors Mediate Inhibition of Noradrenaline Release from Intestinal Symphathetic Nerves. *Br. J. Pharmacol.* 2000, 129(7), 1387-1396.
Bonnet, U. Moclobemide: Evolution, Pharmacodynamic, and Pharmacokinetic Properties. *CNS Drug Rev.* 2002, 8(3), 283-308.

Chen, Z. Effect of histamine H3-receptor antagonist clobenpropit on spatial memory of radial maze performance in rats. *Acta Pharmacol. Sin.* 2000, 21(10), 905-910.
Cheng, Y-C et al.: Relationship Between the Inhibition Constant ($K_1$) and the Concentration of Inhibitor Which Causes 50 Per Cent Inhibition ($I_{50}$) of an Enzymatic Reaction*. Biochemical Pharmacology, vol. 22 (1973), 3099-3108.
Darmani, N.A. and S.L. Reeves. The Mechanisms by which the Selective 5-$HT_{1A}$ Receptor Antagonist S-(+)UH 301 Produces Head-Twitches in Mice. *Pharmacol., Biochem. Behav.* 1996, 55(1), 1-10.
Fink, K. et al. Involvement of Presynaptic $H_3$ Receptors in the Inhibitory Effect of Histamine on Serotonin Release in the Rat Brain Cortex. *Naunyn-Schmiedeberg's Arch. Pharmacol.* 1990, 342(5), 513-519.
Fox, G.B. et al. Effects of Histamine $H_3$ Receptor Ligands GT-2331 and Ciproxifan in a Repeated Acquisition Avoidance Response in the Spontaneously Hypertensive Rat Pup. *Behav. Brain Res.* 2002, 131(1-2), 151-161.
Fox, G.B. et al. Differential in Vivo Effects of $H_3$ Receptor Ligands in a New Mouse Dipsogenia Model. *Pharmacol., Biochem. Behav.* 2002, 72, 741-750.
Griffiths, R.I. et al. Medical Resource Use and Cost of Venlaxafine or Tricyclic Antidepressant Therapy. *Pharmacoeconomics* 1999, 15(5), 495-505.
Hatta, E. et al. Activation of Histamine $H_3$ Receptors Inhibits Carrier-Mediated Norepinephrine Release in a Human Model of Protracted Myocardial Infarction. *J. Pharmacol. Exp. Ther.* 1997, 283(2), 494-500.
Hill, S.J. et al. International Union of Pharmacology. XIII. Classification of Histamine Receptors. *Pharmacol. Rev.* 1997, 49(3), 253-278.
Kelly, S.A. et al.: A convergent approach to huperzine A and analogues. *Org. Biomol. Chem.* 2003, 1, 2865-2876.
Kraly, F.S. et al. $H_1$, $H_2$, and $H_3$ Receptors Contribute to Drinking Elicited by Exogenous Histamine and Eating in Rats. *Pharmacol., Biochem. Behav.* 1996, 53(2), 347-354.
Laitinen, K.S.M. et al. Endogenous Serotonin Modulates Histamine Release in the Hypothalamus as Measured by in Vivo Microdialysis. *Eur. J. Pharmacol.* 1995, 285(2), 159-164.
Lamberti, C. et al. Antidepressant-like Effects of Endogenous Histamine and of Two Histamine $H_1$ Receptor Agonists in the Mouse Forced Swim Test. *Br. J. Pharmacol.* 1998, 123(7), 1331-1336.
Leurs, R. et al. Histamine Homologues Discriminating between Two Functional $H_3$ Receptor Assays. Evidence for $H_3$ Receptor Homogeneity? *J. Pharmacol. Exp. Ther.* 1996, 276(3), 1009-1015.
Lin, J.S. et al. Involvement of Histaminergic Neurons in Arousal Mechanisms Demonstrated with $H_3$-Receptor Ligands in the Cat. *Brain Res.* 1990, 523(2), 325-330.
Lovenberg, T.W. et al. Cloning and Functional Expression of the Human Histamine $H_3$ Receptor. *Molec. Pharmacol.* 1999, 55(6), 1101-1107.

(Continued)

*Primary Examiner*—D. Margaret Seaman
*Assistant Examiner*—Niloofar Rahmani

(57) ABSTRACT

Certain naphthyridine compounds are histamine $H_3$ receptor and serotonin transporter modulators useful in the treatment of histamine $H_3$ receptor- and serotonin-mediated diseases.

34 Claims, No Drawings

OTHER PUBLICATIONS

Lovenberg, T.W. Cloning of Rat Histamine H3 Receptor Reveals Distinct Species Pharmacological Profiles. *J. Pharmacol. Exp. Ther.* 2000, 293, 771-778.

Maryanoff, B.E. et al.: Pyrroloisoquinoline Antidepressants. 2. In-Depth Exploration of Structure-Activity Relationships. J. Med. Chem., vol. 30(8) (1987), 1433-1454. XP000941930.

Maryanoff, B.E. et al.: Pyrroloisequinoline Antidepressants. 3. A Focus on Serotonin. J. Med. Chem, vol. 33 (1990), 2793-2797. XP002398543.

Menza, M.A. et al. Modafinil Augmentation of Antidepressant Treatment in Depression. *J. Clin. Psych.* 2000, 61(5), 378-381.

Miyazaki, S. et al. Effects of Thioperamide on the cholinergic system and the step-through passive avoidance test in mice. *Meth. Find. Exp. Clin. Pharmacol.* 1995, 17(10), 653-658.

Miyazaki, S. et al. Effects of Thioperamide, A Histamine $H_3$-Receptor Antagonist, on a Scopolamine-Induced Learning Deficit Using an Elevated Plus-Maze Test in Mice. *Life Sci.* 1995, 57(23), 2137-2144.

Monti, J.M. et al. Effects of Selective Activation or Blockade of the Histamine $H_3$ Receptor on Sleep and Wakefulness. *Eur. J. Pharmacol.* 1991, 205(3), 283-287.

Monti, J.M. et al. Sleep and Waking during Actue Histamine $H_3$ Agonist BP 2.94 or H3 Antagonist Carboperamide (MR 16155) Administration in Rats. *Neuropsychopharmacology* 1996, 15(1), 31-35.

Olver, J.S. et al. Third Generation Anti-depressants: Do They Offer Advantages over the SSRIs? *CNS Drugs* 2001, 15(12), 941-954.

Orsetti, M. et al. Histamine $H_3$-Receptor Antagonism Improves Memory Retention and Reverses the Cognitive Deficit Induced by Scopolamine in a Two-Trial Place Recognition Task. *Behav. Brain Res.* 2001, 124(2), 235-242.

Parent, M. et al. Analysis of Amino Acids and Catecholamines, 5-Hydroxytryptamine and Their Metabolites in Brain Areas in the Rat Using in Vivo Microdialysis. Methods 2001, 23(1), 11-20.

Perez-Garcia, C. et al. Effects of Histamine $H_3$ Receptor Ligands in Experimental Models of Anxiety and Depression. *Psychopharmacology* 1999, 142(2), 215-220.

Riemann, D. et al. Sleep and Sleep-Wake Manipulations in Bipolar Depression. *Neuropsychobiology* 2002, 45(Suppl. 1), 7-12.

Schlicker, E. et al. Histamine H3 Receptor-Mediated Inhibition of Serotonin Release in the Rat Brain Cortex. *Naunyn-Schmiedeberg's Arch. Pharmacol.* 1988, 337(5), 588-590.

Sharpley, A.L., and P.J. Cowen. Effects of Pharmacologic Treatments on the Sleep of Depressed Patients. *Biol. Psych.* 1995, 37(2), 85-98.

Tomita, T. et al.: Structure-Activity Relationships of Dopamine- and Norepinephrine-Uptake Inhibitors. Chem. Pharm. Bull., vol. 38(6), (1990), 1563-1569. XP 002047151.

* cited by examiner

NAPHTHYRIDINE COMPOUNDS

CROSS REFERENCE TO RELATED APPLICATION

This application claims the benefit under 35 U.S.C. § 119 (e) of provisional application Ser. No. 60/692,003, filed on Jun. 17, 2005, which is incorporated herein by reference in its entirety.

FIELD OF THE INVENTION

The present invention provides compounds that are modulators of the histamine $H_3$ receptor and the serotonin transporter. More particularly, the present invention provides naphtyridine compounds and methods for using them to treat disorders and conditions mediated by the histamine $H_3$ receptor and the serotonin transporter. As a consequence of these activities the compounds of the present invention will have therapeutic utility for the treatment of depression and a range of related disorders.

BACKGROUND OF THE INVENTION

Depression is a chronic illness with an estimated lifetime prevalence of 17%. The total annual cost of depression in the USA is estimated at $44 billion. As such, it represents a major health problem with a serious pharmacoeconomic impact (Griffiths, R. I. et al. *Pharmacoeconomics* 1999, 15(5), 495-505). Although the biochemical basis of depression is not completely elucidated, the most commonly accepted hypothesis states that depression occurs when monoaminergic neurotransmission in the brain is impaired. This theory is largely based on the observation that compounds that improve noradrenergic and/or serotoninergic neurotransmission often have beneficial effects in depression. Such an improvement in monoaminergic neurotransmission can be achieved in several ways. The biological effect of noradrenaline is terminated by two mechanisms: reuptake from the synaptic cleft into the neuron via the norepinephrine transporter (NET), and degradation by monoamine oxidase (MAO). For serotonin, reuptake in the neuron via the serotonin transporter (SERT) likewise limits its availability in the synaptic cleft.

Currently, clinical treatment of depression relies mainly on four types of drugs: 1) MAO inhibitors; 2) tricyclic antidepressants (TCA); 3) selective serotonin reuptake inhibitors (SSRI); and 4) other drugs such as reboxetine and venlafaxine. MAOs have long been used as second-line drugs because of their potentially dangerous side effects, and more recently, reversible MAO-A selective inhibitors with improved profiles have been described (Bonnet, U. *CNS Drug Rev.* 2002, 8(3), 283-308). TCAs such as amitryptiline display complex pharmacological activities. They inhibit reuptake of noradrenaline and serotonin via their respective transporters, but also have affinity at muscarinic and histamine $H_1$ receptors. Thus, their efficacy in treating depression is counterbalanced by numerous unwanted side effects. The SSRIs, which represent the largest and most successful group of antidepressants, show a higher selectivity for the SERT than for the NET, although the exact affinity ratio varies from drug to drug. This class of drugs is characterized by a milder side-effect profile than the MAO-inhibitors or the TCAs. Other drugs have been described, such as reboxetine, which preferentially targets the NET, and venlafaxine, which has dual activity at the SERT and NET (Olver, J. S. et al. *CNS Drugs* 2001, 15(12), 941-954).

Although remarkable progress has been made in the treatment of depression, there remains opportunity for improvement. The delay between start of treatment and subjective improvement is a case in point. Most drugs do not cause an improvement in the Hamilton Rating Scale for Depression until after several weeks of treatment, potentially leaving the patient subject to severe mental anguish during this time. Currently available drugs have a limited response rate and in most clinical trials only about 30% of patients show clinical improvement (Menza, M. A. et al. *J. Clin. Psych.* 2000, 61(5), 378-381). Psychiatrists frequently have to evaluate several drugs for individual patients before a satisfactory therapeutic response is observed. Consequently there is a significant therapeutic need for drugs with a faster onset of action, improved side effect profiles and higher response ratio.

In order to appreciate the rationale for a combined SERT/$H_3$ antagonist, it is necessary to understand the physiology of the histamine $H_3$ receptor. This receptor was described in 1983 (Arrang, J.-M. et al. *Nature (London)* 1983, 302(5911), 832-837) as a presynaptic, auto-inhibitory receptor on histaminergic neurons with a characteristic pharmacology. Activation of the $H_3$ receptor was shown to decrease the amount of histamine released from the nerve terminals and to inhibit the activity of histidine decarboxylase, the rate-limiting enzyme in the synthesis of histamine. The cloning and characterization of the human $H_3$ receptor made it possible to explore its pharmacology (Lovenberg, T. W. et al. *Molec. Pharmacol.* 1999, 55(6), 1101-1107). It is now known that the $H_3$ receptor is expressed on a variety of neurons and thus, when activated, decreases the release of a number of other neurotransmitters including noradrenaline, dopamine, and acetylcholine (Hill, S. J. et al. *Pharmacol. Rev.* 1997, 49(3), 253-278). For the purpose of this discussion, we will focus on its known effects on the release of the neurotransmitters involved in depression, noradrenaline and serotonin. Although the serotoninergic cell bodies are found in the dorsal raphe nucleus while the histaminergic cells are located in the tuberomammillary nucleus of the hypothalamus, both systems have extensive projections throughout the brain. In several regions, such as the suprachiasmatic nucleus (Laitinen, K. S. M. et al. *Eur. J. Pharmacol.* 1995, 285(2), 159-164) and striatum both neurotransmitters are present. It is known that activation of the $H_3$ receptor leads to a decreased release of serotonin, for instance in rat cortex slices (Fink, K. et al. *Naunyn-Schmiedeberg's Arch. Pharmacol.* 1990, 342(5), 513-519; Schlicker, E. et al. *Naunyn-Schmiedeberg's Arch. Pharmacol.* 1988, 337(5), 588-590). Functional antagonists of the $H_3$ receptor lead to an increased release of noradrenaline in the central (mouse cortex slices, Leurs, R. et al. *J. Pharmacol. Exp. Ther.* 1996, 276(3), 1009-1015; the rat hippocampus, Alvez-Rodrigues, A. et al. *Brain Res.* 1998, 788(1-2), 179-186) and peripheral nervous system (human myocardial nerves, Hatta, E. et al. *J. Pharmacol. Exp. Ther.* 1997, 283(2), 494-500; guinea-pig intestinal sympathetic nerves, Blandizzi, C. et al. *Br. J. Pharmacol.* 2000, 129(7), 1387-1396). However, there is little evidence that $H_3$ receptor antagonists alone are capable of increasing serotonin levels in vivo to those required for antidepressant effects. Microdialysis studies of the effect of $H_3$ antagonists on serotonin levels in the brain of live animals are lacking. There are sparse reports indicating that thioperamide, an $H_3$ receptor antagonist, may have an antidepressant effect per se in the mouse or rat forced swim test (Lamberti, C. et al. *Br. J. Pharmacol.* 1998, 123(7), 1331-1336; Perez-Garcia, C. et al. *Psychopharmacology* 1999, 142(2), 215-220).

The rationale for combining $H_3$ receptor blockade and SERT activity in one single molecule is the expectation that both mechanisms will contribute synergistically to enhanced concentrations of serotonin in the synaptic cleft. Antagonism at the $H_3$ receptor will provide increased release of serotonin-containing vesicles into the synaptic cleft, and concomitant blockade of the SERT will decrease the neuronal reuptake of these neurotransmitter molecules. Thus, higher concentrations of serotonin will be achieved, leading to an enhanced therapeutic effect.

Among the prominent vegetative symptoms of depression are disturbed sleep and the daytime fatigue associated with it. Polysomnographic investigations have shown severe disturbances in the sleep architecture of depressed patients. Among the typical abnormalities observed are: discontinuous sleep, decreased slow-wave sleep, shorter latency to REM sleep and an increased intensity and duration of REM sleep (Riemann, D. et al. *Neuropsychobiology* 2002, 45(Suppl. 1), 7-12). It is believed that suppression of REM sleep is involved in antidepressant efficacy. This is illustrated by the dramatic success of overnight deprivation of (REM) sleep (Riemann et al. 2002). Another non-pharmacological treatment for depression, electroconvulsant therapy, likewise decreases REM sleep. Virtually all of the available antidepressant drugs, regardless of their neurochemical mechanism of action, suppress REM sleep, nefazodone (a $5$-$HT_{2A}$ antagonist) being the exception (Sharpley, A. L., Cowen, P. J. *Biol. Psych.* 1995, 37(2), 85-98). Antidepressant drugs also affect slow-wave-sleep, although in a less clear manner. $H_3$ antagonists share this REM-sleep suppressing property and one of the main biological effects of histamine $H_3$ antagonists is to improve wakefulness. Administration of $H_3$ antagonists has been shown to decrease REM and non-REM sleep in several animal species. For example, the $H_3$ antagonist carboperamide induces waking in rats (Monti, J. M. et al. *Neuropsychopharmacology* 1996, 15(1), 31-35). Another $H_3$ antagonist, thioperamide, decreased both REM and non-REM sleep in rats (Monti, J. M. et al. *Eur. J. Pharmacol.* 1991, 205(3), 283-287) and cats (Lin, J.-S. et al. *Brain Res.* 1990, 523(2), 325-330). It is of interest to note that although $H_3$ antagonists promote wakefulness, they do so much less potently than amphetamine derivatives. They may thus be considered mild stimulants. The daytime correlate of disturbed sleep is fatigue. Indeed, fatigue and lethargy are prominent symptoms of depression, and there is considerable interest in the use of stimulants to augment antidepressant therapy (Menza et al., 2000). However, most of the available stimulants, like the amphetamine derivatives and methylphenidate, carry a considerable risk of abuse and are not ideal therapeutic choices. Modafinil, a wake-promoting compound of unknown mechanism with a lower addictive potential, is marketed for the treatment of narcolepsy. In a small series of patients it was shown that addition of a low dose of modafinil to traditional antidepressant therapy resulted in a faster onset of action. Fatigue was particularly responsive to this therapy, but the cognitive and physical subscales of the Hamilton Rating Scale for Depression also improved (Menza et al., 2000). The behavioral profile of $H_3$ antagonists (suppression of sleep with no stimulation of locomotor activity and limited addictive potential) is much like that of modafinil. Therefore, a combined $H_3$/SSRI compound would provide symptomatic relief for the fatigue during the first weeks of treatment, before the mood-elevating effect of the SSRI can be noticed.

Depression is also associated with a number of cognitive symptoms such as impaired memory and concentration difficulties. $H_3$ antagonists have been shown to improve memory in a variety of memory tests, including the elevated plus maze in mice (Miyazaki, S. et al. *Life Sci.* 1995, 57(23), 2137-2144), a two-trial place recognition task (Orsetti, M. et al. *Behav. Brain Res.* 2001, 124(2), 235-242), the passive avoidance test in mice (Miyazaki, S. et al. *Meth. Find. Exp. Clin. Pharmacol.* 1995, 17(10), 653-658) and the radial maze in rats (Chen, Z. *Acta Pharmacol. Sin.* 2000, 21(10), 905-910). Also, in the spontaneously hypertensive rat, an animal model for the learning impairments in attention-deficit disorders, $H_3$ antagonists were shown to improve memory (Fox, G. B. et al. *Behav. Brain Res.* 2002, 131(1-2), 151-161). Although no human studies are available, the evidence indicates that a combined SERT/$H_3$ antagonist will provide additional benefit in combating the cognitive impairments associated with depression.

In summary, the combination of $H_3$ receptor antagonism with SERT activity will result in the production of drugs with an improved antidepressant profile compared to an SSRI alone. These drugs will be especially efficacious in ameliorating the symptoms of fatigue, disturbed sleep and memory loss associated with depression.

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety. In addition, U.S. Patent Appl. No. 60/637,173 is also incorporated by reference.

SUMMARY OF THE INVENTION

The invention features a compound of formula (I):

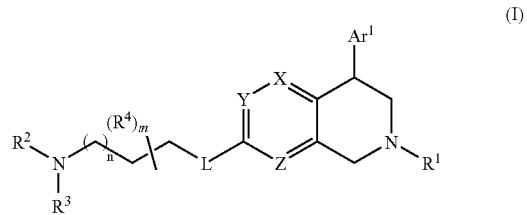

wherein
one or two of X, Y, and Z is N, and the remaining of X, Y, and Z are $CR^5$;

L is —O— or —$CH_2$— and n is 1 or 2; or L is —C≡C— and n is 0 or 1;

m is 0, 1, or 2;

$R^1$ is —H; or is —$C_{1-6}$alkyl, —$C_{3-6}$alkenyl, —$C_{3-6}$alkynyl, —$C_{3-7}$cycloalkyl, —$C_{1-6}$alkyl$C_{3-7}$cycloalkyl, —$COOC_{1-6}$alkyl, or —COObenzyl, each optionally mono-, di-, or tri-substituted with $R^a$;

$R^a$ is selected from the group consisting of —OH, —$OC_{1-6}$alkyl, phenyl optionally substituted with —$OC_{1-4}$alkyl or halo, —CN, —$NO_2$, —N($R^b$)$R^c$ (wherein $R^b$ and $R^c$ are independently —H or —$C_{1-6}$alkyl), —C(O)N($R^b$)$R^c$, —N($R^b$)C(O)$R^b$, —N($R^b$)$SO_2C_{1-6}$alkyl, —C(O)$C_{1-6}$alkyl, —S(O)$_{0-2}$—$C_{1-6}$alkyl, —$SO_2$N($R^b$)$R^c$, —$SCF_3$, halo, —$CF_3$, —$OCF_3$, —COOH, and —$COOC_{1-6}$alkyl;

$R^2$ and $R^3$ are independently selected from —H, or from the group consisting of:

A) —$C_{1-6}$alkyl, —$C_{3-6}$alkenyl, —$C_{3-6}$alkynyl, —$C_{3-7}$cycloalkyl, —$C_{1-6}$alkyl$C_{3-7}$cycloalkyl, benzyl;

B) phenyl or pyridyl, optionally fused at two adjacent carbon ring members to a three- or four-membered hydrocarbon moiety to form a fused five- or six-membered aromatic ring, which moiety has one carbon atom replaced by >O, >S, >NH, or >N($C_{1-4}$alkyl), and which moiety has up to one additional carbon atom optionally replaced by —N═;

C) a 4-8 membered heterocyclic ring, said heterocyclic ring having a carbon atom which is the point of attachment, having 1 or 2 heteroatom members selected from >O, >S(O)$_{0-2}$, and >NH, and having 0 or 1 double bonds; and D) a monocyclic aromatic hydrocarbon group having five or six ring atoms, having a carbon atom which is the point of attachment, having one carbon atom replaced by >O, >S, >NH, or >N($C_{1-4}$alkyl), having up to one additional carbon atom optionally replaced by —N═, and optionally benzofused or pyridofused;

where each of A)-D) is optionally mono-, di-, or tri-substituted with a moiety selected from the group consisting of —OH, —$C_{1-4}$alkylOH, —O$C_{1-6}$alkyl, —CN, —NO$_2$, —N($R^d$)$R^e$ (wherein $R^d$ and $R^e$ are independently —H or —$C_{1-6}$alkyl), —C(O)N($R^d$)$R^e$, —N($R^d$)C(O)$R^d$, —N($R^d$)SO$_2$$C_{1-6}$alkyl, —C(O)$C_{1-6}$alkyl, —S(O)$_{0-2}$—$C_{1-6}$alkyl, —SO$_2$N($R^d$)$R^e$, —SCF$_3$, halo, —CF$_3$, —OCF$_3$, —COOH, —COO$C_{1-6}$alkyl, —OC(O)N($R^d$)$R^e$, and —OC(O)O$R^d$;

or, alternatively, $R^2$ and $R^3$ may be taken together with the nitrogen to which they are attached to form a 4-8 membered heterocyclic ring, said heterocyclic ring having 0 or 1 additional heteroatom members separated from the nitrogen of attachment by at least one carbon member and selected from >O, >S(O)$_{0-2}$, >NH, and >N$R^f$, having 0 or 1 double bonds, having 0, 1, or 2 carbon members separated from the nitrogen of attachment by at least one carbon member which is a carbonyl, optionally benzo or pyrido fused, optionally having one carbon member that forms a bridge, and having 0-5 carbon member substituents $R^{ff}$, $R^f$ is selected from the group consisting of —$C_{1-6}$alkyl optionally mono-, di-, or tri-substituted with halo, —$C_{3-6}$alkenyl, —$C_{3-6}$alkynyl, —$C_{3-7}$cycloalkyl, —$C_{1-6}$alkyl$C_{3-7}$cycloalkyl, —$C_{2-6}$alkylOH, —C(O)N($R^g$)$R^h$ (wherein $R^g$ and $R^h$ are independently —H or —$C_{1-6}$alkyl), —C(O)$R^i$ (where $R^i$ is —$C_{1-6}$alkyl, —$C_{3-8}$cycloalkyl, phenyl, or 5- or 6-membered aromatic heterocyclyl, each optionally mono-, di-, or tri-substituted with —$C_{1-3}$alkyl, —OH, —O$C_{1-6}$alkyl, —CF$_3$, or halo), —S(O)$_{0-2}$—$C_{1-6}$alkyl, and —COO$C_{1-6}$alkyl;

$R^{ff}$ is selected from the group consisting of —$C_{1-6}$alkyl optionally mono-, di-, or tri-substituted with halo, —$C_{2-6}$alkenyl, —$C_{2-6}$alkynyl, —$C_{3-7}$cycloalkyl, —$C_{1-6}$alkyl$C_{3-7}$cycloalkyl, halo, —OH, —$C_{1-6}$alkylOH, —O$C_{1-6}$alkyl, —O$C_{2-3}$alkylO—, —CN, —NO$_2$, —N($R^g$)$R^h$ (wherein $R^g$ and $R^h$ are independently —H or —$C_{1-6}$alkyl), —C(O)N($R^g$)$R^h$, —N($R^g$)C(O)$R^g$, —N($R^g$)SO$_2$$C_{1-6}$alkyl, —C(O)$R^i$ (where $R^i$ is —$C_{1-6}$alkyl, —$C_{3-8}$cycloalkyl, phenyl, or 5- or 6-membered aromatic heterocyclyl, each optionally mono-, di-, or tri-substituted with —$C_{1-3}$alkyl, —OH, —O$C_{1-6}$alkyl, —CF$_3$, or halo), —S(O)$_{0-2}$—$C_{1-6}$alkyl, —SO$_2$N($R^y$)$R^z$, —SCF$_3$, —OCF$_3$, —COOH, and —COO$C_{1-6}$alkyl;

$R^4$ is —OH, —O$C_{1-6}$alkyl, —CF$_3$, —$C_{1-6}$alkyl, or halo; two $R^4$ substituents may be taken together to form methylene or ethylene; or one of $R^4$ is taken together with $R^2$ to form methylene, ethylene, or propylene; wherein each methylene, ethylene, or propylene is optionally substituted with —OH, —O$C_{1-6}$alkyl, —S$C_{1-6}$alkyl, —CF$_3$, —$C_{1-6}$alkyl, amino, or halo;

$R^5$ is selected from the group consisting of —H, —$C_{1-6}$alkyl, —OH, —O$C_{1-6}$alkyl, —S$C_{1-6}$alkyl, and halo;

$Ar^1$ is an aryl or heteroaryl ring selected from the group consisting of:

a) phenyl, optionally mono-, di-, or tri-substituted with $R^j$ or di-substituted on adjacent carbons with —O$C_{1-4}$alkyleneO— optionally mono- or di-substituted with fluoro, —(CH$_2$)$_{2-3}$NH—, —(CH$_2$)$_{1-2}$NH(CH$_2$)—, —(CH$_2$)$_{2-3}$N($C_{1-4}$alkyl)-, or —(CH$_2$)$_{1-2}$N($C_{1-4}$alkyl)(CH$_2$)—;

$R^j$ is selected from the group consisting of
1) —OH, —$C_{1-6}$alkyl, —O$C_{1-6}$alkyl optionally mono-, di-, or tri-substituted with halo, —$C_{2-6}$alkenyl, —O$C_{3-6}$alkenyl, —$C_{2-6}$alkynyl, —O$C_{3-6}$alkynyl, —$C_{3-6}$cycloalkyl, —O$C_{3-6}$cycloalkyl, —CN, —NO$_2$, —N($R^k$)$R^l$ (wherein $R^k$ and $R^l$ are independently —H or —$C_{1-6}$alkyl), —N($R^k$)CO$R^l$, —N($R^k$)SO$_2$$C_{1-6}$alkyl, —C(O)$C_{1-6}$alkyl, —S(O)$_{0-2}$—$C_{1-6}$alkyl, —C(O)N($R^m$)$R^n$ (wherein $R^m$ and $R^n$ are independently —H or —$C_{1-6}$alkyl, or $R^m$ and $R^n$ taken together with their nitrogen of attachment form a 4-8 membered heterocyclic ring having 1 or 2 heteroatom members selected from >O, >S(O)$_{0-2}$, >NH, and >N$C_{1-6}$alkyl, having 0 or 1 double bonds, having 0 or 1 carbonyl members), —SO$_2$N($R^m$)$R^n$, —SCF$_3$, halo, —CF$_3$, —COOH, —COO$C_{1-6}$alkyl, and —COO$C_{3-7}$cycloalkyl; and 2) a 4-8 membered saturated or partially saturated heterocyclic ring, having 1 or 2 heteroatom members selected from >O, >S(O)$_{0-2}$, >NH, and >N$C_{1-6}$alkyl, having 0 or 1 carbonyl members; said ring optionally mono-, di-, or tri-substituted with $R^p$;

$R^p$ is a substituent independently selected from the group consisting of —OH, —$C_{1-6}$alkyl, —O$C_{1-6}$alkyl, phenyl, —CN, —NO$_2$, —N($R^q$)$R^r$ (wherein $R^q$ and $R^r$ are independently —H, —$C_{1-6}$alkyl, or —$C_{2-6}$alkenyl), —C(O)N($R^q$)$R^r$, —N($R^q$)C(O)$R^r$, —N($R^q$)SO$_2$$C_{1-6}$alkyl, —C(O)$C_{1-6}$alkyl, —S(O)$_{0-2}$—$C_{1-6}$alkyl, —SO$_2$N($R^q$)$R^r$, —SCF$_3$, halo, —CF$_3$, —OCF$_3$, —OCHF$_2$, —COOH, and —COO$C_{1-6}$alkyl;

b) phenyl or pyridyl fused at two adjacent carbon ring members to a three membered hydrocarbon moiety to form a fused five membered aromatic ring, which moiety has one carbon atom replaced by >O, >S, >NH, or >N($C_{1-4}$alkyl), and which moiety has up to one additional carbon atom optionally replaced by —N═, the fused rings optionally mono-, di-, or tri-substituted with $R^t$;

$R^t$ is a substituent independently selected from the group consisting of —OH, —$C_{1-6}$alkyl, —O$C_{1-6}$alkyl, phenyl, —CN, —NO$_2$, —N($R^u$)$R^v$ (wherein $R^u$ and $R^v$ are independently —H or —$C_{1-6}$alkyl), —C(O)N($R^u$)$R^v$, —N($R^u$)C(O)$R^v$, —N($R^u$)SO$_2$$C_{1-6}$alkyl, —C(O)$C_{1-6}$alkyl, —S(O)$_{0-2}$—$C_{1-6}$alkyl, —SO$_2$N($R^u$)$R^v$, —SCF$_3$, halo, —CF$_3$, —OCF$_3$, —OCHF$_2$, —COOH, and —COO$C_{1-6}$alkyl;

c) phenyl fused at two adjacent ring members to a four membered hydrocarbon moiety to form a fused six membered aromatic ring, which moiety has 0, 1, or 2 carbon atoms replaced by —N═, the fused rings optionally mono-, di-, or tri-substituted with $R^t$;

d) a monocyclic aromatic hydrocarbon group having five ring atoms, having a carbon atom which is the point of attachment, having one carbon atom replaced by >O, >S, >NH, or >N($C_{1-4}$alkyl), having up to one additional carbon atom optionally replaced by —N═, optionally mono- or di-substituted with $R^t$, and optionally benzofused or pyridofused at two adjacent carbon atoms, where the benzofused or pyridofused moiety is optionally mono-, di-, or tri-substituted with $R^t$; and e) a monocyclic aromatic hydrocarbon group having six ring atoms, having a carbon atom which is the point of attachment, having one or two carbon atoms replaced by —N=, optionally mono- or di-substituted with $R^t$, and optionally benzofused or pyridofused at two adjacent carbon atoms, where the benzofused or pyridofused moiety is optionally mono- or di-substituted with $R^t$;

and enantiomers, diastereomers, hydrates, solvates and pharmaceutically acceptable salts, esters, and amides thereof.

Isomeric forms of the compounds of formula (I), and of their pharmaceutically acceptable salts, esters, and amides, are encompassed within the present invention, and reference herein to one of such isomeric forms is meant to refer to at least one of such isomeric forms. One of ordinary skill in the art will recognize that compounds according to this invention may exist, for example in a single isomeric form whereas other compounds may exist in the form of a regioisomeric mixture.

The invention also features pharmaceutical compositions containing such compounds and methods of using such compounds and compositions in the treatment or prevention of disease states mediated by the histamine $H_3$ receptor and the serotonin transporter.

Compounds of the present invention are useful in combination with other therapeutic agents as a combination therapy method, including use in combination with $H_1$ receptor antagonists, $H_2$ receptor antagonists, $H_3$ receptor antagonists, and neurotransmitter modulators such as serotonin-norepinephrine reuptake inhibitors, selective serotonin reuptake inhibitors (SSRIs), noradrenergic reuptake inhibitors, non-selective serotonin re-uptake inhibitors (NSSRIs), and modafinil.

Additional features and advantages of the invention will become apparent from the detailed description and examples below, and the appended claims.

DETAILED DESCRIPTION

Particular preferred compounds of the invention comprise a compound of formula (I), or an enantiomer, diastereomer, hydrate, solvate thereof, or a pharmaceutically acceptable salt, amide or ester thereof, wherein n, m, L, X, Y, Z, $R^{1-4}$, and $Ar^1$ have any of the meanings defined hereinabove and equivalents thereof, or at least one of the following assignments and equivalents thereof. Such assignments may be used where appropriate with any of the definitions, claims or embodiments defined herein:

Preferably, X is N.
Preferably, Y is N.
Preferably, Z is N.
Preferably, Y and Z are N.
Preferably, L is —O— and n is 1.
Preferably, L is —CH$_2$— and n is 1.
Preferably, L is —C≡C— and n is 0.
Preferably, m is 0 or 1.
Preferably, $R^1$ is selected from the group consisting of hydrogen, methyl, ethyl, propyl, isopropyl, butyl, pentyl, hexyl, benzyl, allyl, propargyl, cyclopropyl, cyclobutyl, cyclopentyl, cyclohexyl, cyclopropylmethyl, —COOCH$_3$, —COO-t-butyl, and —COObenzyl.

More preferably, $R^1$ is methyl, ethyl, propyl, allyl, propargyl, or benzyl.

Even more preferably, $R^1$ is hydrogen or methyl.

Preferably, $R^2$ and $R^3$ are independently selected from —H, or, optionally substituted, from the group consisting of:

A) methyl, ethyl, isopropyl, butyl, pentyl, hexyl, allyl, propargyl, cyclopropyl, cyclobutyl, cyclopentyl, cyclohexyl, cyclopropylmethyl, benzyl, B) phenyl, pyridyl, 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl, C) azetidinyl, pyrrolidinyl, piperidinyl, and D) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, and 3-indazolyl.

More preferably, $R^2$ and $R^3$, optionally substituted, are independently selected from methyl, ethyl, isopropyl, pyrrolidinyl, piperidinyl, 2-benzothiazolyl, and methoxyethyl.

Even more preferably, $R^2$ and $R^3$ are, independently, ethyl, isopropyl, methoxyethyl, or 2-benzothiazolyl.

In a preferred embodiment, $R^2$ and $R^3$, optionally substituted, are taken together with the nitrogen to which they are attached to form a ring selected from the group consisting of azetidinyl, pyrrolidinyl, piperidinyl, morpholinyl, thiomorpholinyl, piperazinyl, homopiperidinyl, 1,3-dihydro-isoindol-2-yl, 5,6-dihydro-4H-pyrimidin-1-yl, and 1,1-dioxo-1λ$^6$-thiomorpholin-4-yl.

In an alternative embodiment, $R^2$ and $R^3$ are taken together with the nitrogen to which they are attached to form a 4-8 membered heterocyclic ring, said heterocyclic ring selected from piperidine, pyrrolidine, and morpholine, said ring substituted with 1 or 2 substituents $R^{ff}$.

Preferably, $R^{ff}$ is selected from the group consisting of methyl, ethyl, isopropyl, butyl, hexyl, —CF$_3$, —CHF$_2$, vinyl, allyl, propargyl, cyclopropyl, cyclopentyl, cyclopropylmethyl, cyclobutylethyl, bromo, chloro, fluoro, iodo, —OH, hydroxymethyl, hydroxyethyl, methoxy, ethoxy, isopropoxy, pentyloxy, —O(CH$_2$)$_2$O—, —O(CH$_2$)$_3$O—, —CN, amino, methylamino, dimethylamino, diethylamino, diethylcarbamoyl, methanesulfanyl, methanesulfonyl, methanesulfonamido, —C(O)R$^i$, —COOH, and ethoxycarbonyl.

More preferably, $R^{ff}$ is selected from the group consisting of methyl, fluoro, —OH, —CF$_3$, hydroxymethyl, hydroxyethyl, dimethylamino, ethoxycarbonyl, and —O(CH$_2$)$_2$O—.

Preferably, $R^i$ is selected from the group consisting of methyl, pyridyl, isopropyl, cyclobutyl, cyclopropyl, N-methylpyrrolyl, and 1-methylimidazolyl.

More preferably, $R^2$ and $R^3$ are taken together with the nitrogen to which they are attached to form azetidinyl, 2-methylpyrrolidinyl, 3-hydroxypyrrolidinyl, 3-dimethylaminopyrrolidinyl, 2,5-dimethylpyrrolidinyl, 2-trifluoromethylpyrrolidinyl, 2-hydroxymethylpyrrolidinyl, piperidinyl, 4-fluoropiperidinyl, 3,3-difluoropiperidinyl, 4,4-difluoropiperidinyl, 3-trifluoromethylpiperidinyl, 4-trifluoromethylpiperidinyl, 1,4-dioxa-8-aza-spiro[4.5]dec-8-yl, morpholinyl, 4-cyanopiperidinyl, 4-carboethoxypiperidinyl, 3-hydroxypiperidinyl, 4-hydroxypiperidinyl, 2-hydroxymethylpiperidinyl, 3-hydroxymethylpiperidinyl, 4-hydroxymethylpiperidinyl, 4-hydroxyethylpiperidinyl, 3-methylmorpholin-4-yl, 3-hydroxymethylmorpholin-4-yl, 2-hydroxymethylmorpholin-4-yl, 2,6-dimethylmorpholin-4-yl, 1,3-dihydro-isoindol-2-yl, 5,6-dihydro-4H-pyrimidin-1-yl, 1,1-dioxo-1λ$^6$-thiomorpholin-4-yl, or 2-methylmorpholin-4-yl.

Even more preferably, $R^2$ and $R^3$ are taken together with the nitrogen to which they are attached to form piperidinyl, 4-fluoropiperidinyl, 4,4-difluoropiperidinyl, morpholinyl, or 3-methylmorpholin-4-yl.

Preferably, $R^4$ is methoxy, ethoxy, isopropoxy, pentyloxy, —$CF_3$, methyl, ethyl, propyl, isobutyl, pentyl, chloro, or fluoro.

More preferably, $R^4$ is hydroxy, methyl, methoxy, fluoro, or —$CF_3$.

Preferably, two $R^4$ are taken together to form methylene.

Preferably, $R^2$ and one of $R^4$ are taken together to form ethylene or propylene.

Preferably, $R^5$ is hydrogen, methyl, ethyl, isopropyl, hexyl, hydroxyl, methoxy, ethoxy, isopropoxy, methylsulfanyl, bromo, chloro, fluoro, or iodo.

More preferably, $R^5$ is hydrogen.

Preferably, $Ar^1$, optionally substituted, is selected from the group consisting of:

a) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl, b) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl, c) naphthyl, 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl, d) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, 3-indazolyl, and e) pyridinyl, pyridinyl-N-oxide, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl, [1,5], [1,6], [1,7], or [1,8]naphthyridin-2-, 3-, or 4-yl, [2,5], [2,6], [2,7], [2,8]naphthyridin-1-, 3-, or 4-yl.

More preferably, $Ar^1$, optionally substituted, is selected from the group consisting of phenyl, pyridyl, pyrazinyl, thiazolyl, pyrazolyl, and thiophenyl.

Even more preferably, $Ar^1$ is selected from the group consisting of phenyl, 2-methoxyphenyl, 3-methoxyphenyl, 4-methoxyphenyl, 2,4-dimethoxyphenyl, 2,5-dimethoxyphenyl, 3,4-dimethoxyphenyl, 3,5-dimethoxyphenyl, 3,4,5-trimethoxyphenyl, 2-methylphenyl, 3-methylphenyl, 4-methylphenyl, 4-ethylphenyl, 3-ethynylphenyl, 4-ethynylphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 3-iodophenyl, 4-iodophenyl, 2-trifluoromethylphenyl, 3-trifluoromethylphenyl, 4-trifluoromethylphenyl, 3-trifluoromethoxyphenyl, 4-trifluoromethoxyphenyl, 4-difluoromethoxyphenyl, 3-cyanophenyl, 4-cyanophenyl, 3-acetylphenyl, 4-acetylphenyl, 3,4-difluorophenyl, 3,4-dichlorophenyl, 2,3-difluorophenyl, 2,3-dichlorophenyl, 2,4-difluorophenyl, 2,4-dichlorophenyl, 2,5-dichlorophenyl, 3,5-dichlorophenyl, 3-nitrophenyl, 4-nitrophenyl, 3-chloro-4-fluorophenyl, 3-chloro-4-methoxyphenyl, 3-chloro-4-difluoromethoxyphenyl, 3-fluoro-4-chlorophenyl, benzo[1,3]dioxol-4 or 5-yl, 2-hydroxyphenyl, 3-hydroxyphenyl, 4-hydroxyphenyl, 4-hydroxy-2-methylphenyl, 4-hydroxy-3-fluorophenyl, 3,4-dihydroxyphenyl, 4-aminophenyl, 4-dimethylaminophenyl, 4-carbamoylphenyl, 4-fluoro-3-methylphenyl, 4-methanesulfanylphenyl, 4-methanesulfinylphenyl, 4-methanesulfonylphenyl, 4-trifluoromethanesulfanylphenyl, thiophen-2-yl, thiophen-3-yl, 2-pyridinyl, 3-pyridinyl, 4-pyridinyl, 2-chloro-5-pyridinyl, 2-dimethylamino-5-pyridinyl, 2-methoxy-5-pyridinyl, 2-thiomethyl-5-pyridinyl, 2-hydroxy-5-pyridinyl, oxazol-5-yl, thiazol-5-yl, thiazol-2-yl, 2H-pyrazol-3-yl, pyrazin-2-yl, 1-naphthyl, 2-naphthyl, 4-imidazol-1-ylphenyl, 4-pyrazol-1-ylphenyl, 1H-indol-5-yl, 1H-benzimidazol-5-yl, benzo[b]thiophen-7-yl, and 4-biphenyl.

In a particular embodiment, $Ar^1$, optionally substituted with halo, is 4-methoxyphenyl or 4-methanesulfanylphenyl.

It is understood that some compounds referred to herein are chiral and/or have geometric isomeric centers, for example E- and Z- isomers. The present invention encompasses all such optical, including stereoisomers and racemic mixtures, diastereomers, and geometric isomers that possess the activity that characterizes the compounds of this invention. Compounds of the invention may exist as single enantiomers, mixtures of enantiomers, or racemic mixtures. In certain embodiments, the absolute configuration of a single enantiomer may be unknown. In addition, certain compounds referred to herein can exist in solvated as well as unsolvated forms. It is understood that this invention encompasses all such solvated and unsolvated forms that possess the activity that characterizes the compounds of this invention.

Compounds according to the present invention that have been modified to be detectable by some analytic technique are also within the scope of this invention. The compounds of the present invention may be labeled with radioactive elements such as $^{125}I$, $^{18}F$, $^{11}C$, $^{64}Cu$, and the like for use in imaging or for radioactive treatment of patients. An example of such compounds is an isotopically labeled compound, such as an $^{18}F$ isotopically labeled compound that may be used as a probe in detection and/or imaging techniques, such as positron emission tomography (PET) and single-photon emission computed tomography (SPECT). Preferably, compounds of the present invention labeled with $^{18}F$ or $^{11}C$ may be used as a positron emission tomography (PET) molecular probe for studying disorders mediated by the histamine $H_3$ receptor and the serotonin transporter. Another example of such compounds is an isotopically labeled compound, such as a deuterium and/or tritium labeled compound that may be used in reaction kinetic studies. The compounds described herein may be reacted with appropriate functionalized radioactive reagents using conventional chemistry to provide radiolabeled compounds.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with a compound of formula (I) or with a compound that converts to a compound of formula (I) in vivo after administration to the patient. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Preferred compounds, which are tetrahydronaphthyridine compounds, are selected from the group consisting of:

| EX | CHEMICAL NAME |
|---|---|
| 1 | 4-(2-Fluoro-phenyl)-7-(3-piperidin-1-yl-propoxy)-1,2,3,4-tetrahydro-[2,6]naphthyridine; |
| 2 | 4-(2-Fluoro-phenyl)-2-methyl-7-(3-piperidin-1-yl-propoxy)-1,2,3,4-tetrahydro-[2,6]-naphthyridine; |
| 3 | 2-Methyl-4-phenyl-7-(3-piperidin-1-yl-propoxy)-1,2,3,4-tetrahydro-[2,6]-naphthyridine; |
| 4 | 4-Phenyl-7-(3-piperidin-1-yl-propoxy)-1,2,3,4-tetrahydro-[2,6]naphthyridine; |
| 5 | Diethyl-[3-(8-phenyl-5,6,7,8-tetrahydro-[2,6]naphthyridin-3-yloxy)-propyl]-amine; |
| 6 | 4-(4-Methoxy-phenyl)-7-(3-piperidin-1-yl-propoxy)-1,2,3,4-tetrahydro-[2,6]-naphthyridine; |
| 7 | Diethyl-[3-(6-methyl-8-phenyl-5,6,7,8-tetrahydro-[2,6]naphthyridin-3-yloxy)-propyl]-amine; |
| 8 | 4-(4-Methoxy-phenyl)-2-methyl-7-(3-piperidin-1-yl-propoxy)-1,2,3,4-tetrahydro-[2,6]-naphthyridine; |
| 9 | 4-(4-Methoxy-phenyl)-7-[2-(1-methyl-pyrrolidin-2-yl)-ethoxy]-1,2,3,4-tetrahydro-[2,6]-naphthyridine; |
| 10 | 4-(4-Methoxy-phenyl)-2-methyl-7-[2-(1-methyl-pyrrolidin-2-yl)-ethoxy]-1,2,3,4-tetrahydro-[2,6]-naphthyridine; |
| 11 | 4-(4-Methoxy-phenyl)-7-(3-morpholin-4-yl-propoxy)-1,2,3,4-tetrahydro-[2,6]-naphthyridine; |
| 12 | 4-(4-Methoxy-phenyl)-2-methyl-7-(3-morpholin-4-yl-propoxy)-1,2,3,4-tetrahydro-[2,6]-naphthyridine; |
| 13 | 4-(3-Methoxy-phenyl)-7-(3-piperidin-1-yl-propoxy)-1,2,3,4-tetrahydro-[2,6]-naphthyridine; |
| 14 | 4-(3-Methoxy-phenyl)-2-methyl-7-(3-piperidin-1-yl-propoxy)-1,2,3,4-tetrahydro-[2,6]-naphthyridine; |
| 15 | 4-(3,4-Dichloro-phenyl)-7-(3-piperidin-1-yl-propoxy)-1,2,3,4-tetrahydro-[2,6]-naphthyridine; |
| 16 | 4-(3,4-Dichloro-phenyl)-2-methyl-7-(3-piperidin-1-yl-propoxy)-1,2,3,4-tetrahydro-[2,6]-naphthyridine; |
| 17 | 4-(4-Fluoro-phenyl)-7-(3-piperidin-1-yl-propoxy)-1,2,3,4-tetrahydro-[2,6]naphthyridine; |
| 18 | 4-(4-Fluoro-phenyl)-2-methyl-7-(3-piperidin-1-yl-propoxy)-1,2,3,4-tetrahydro-[2,6]-naphthyridine; |
| 19 | 7-[3-(4,4-Difluoro-piperidin-1-yl)-propoxy]-4-(4-methoxy-phenyl)-1,2,3,4-tetrahydro-[2,6]-naphthyridine; |
| 20 | Diethyl-{3-[8-(4-methoxy-phenyl)-5,6,7,8-tetrahydro-[2,6]naphthyridin-3-yloxy]-propyl}-amine; |
| 21 | {3-[8-(3,4-Dichloro-phenyl)-5,6,7,8-tetrahydro-[2,6]naphthyridin-3-yloxy]-propyl}-diethyl-amine; |
| 22 | 7-(1-Benzyl-piperidin-4-yloxy)-4-(4-methoxy-phenyl)-1,2,3,4-tetrahydro-[2,6]-naphthyridine; |
| 23 | 4-(4-Chloro-phenyl)-7-(3-piperidin-1-yl-propoxy)-1,2,3,4-tetrahydro-[2,6]naphthyridine; |
| 24 | 4-(3-Chloro-phenyl)-7-(3-piperidin-1-yl-propoxy)-1,2,3,4-tetrahydro-[2,6]naphthyridine; |
| 25 | 4-(2-Chloro-phenyl)-7-(3-piperidin-1-yl-propoxy)-1,2,3,4-tetrahydro-[2,6]naphthyridine; |
| 26 | 4-(3,4-Dichloro-phenyl)-7-(3-morpholin-4-yl-propoxy)-1,2,3,4-tetrahydro-[2,6]-naphthyridine; |
| 27 | 4-(3-Chloro-phenyl)-2-methyl-7-(3-piperidin-1-yl-propoxy)-1,2,3,4-tetrahydro-[2,6]-naphthyridine; |
| 28 | 7-[3-(4,4-Difluoro-piperidin-1-yl)-propoxy]-4-(4-methoxy-phenyl)-2-methyl-1,2,3,4-tetrahydro-[2,6]naphthyridine; |
| 29 | Diethyl-{3-[8-(4-methoxy-phenyl)-6-methyl-5,6,7,8-tetrahydro-[2,6]naphthyridin-3-yloxy]-propyl}-amine; |
| 30 | {3-[8-(3,4-Dichloro-phenyl)-6-methyl-5,6,7,8-tetrahydro-[2,6]naphthyridin-3-yloxy]-propyl}-diethyl-amine; |
| 31 | 7-(1-Isopropyl-piperidin-4-ylmethoxy)-4-(4-methoxy-phenyl)-1,2,3,4-tetrahydro-[2,6]-naphthyridine; |
| 32 | 4-(3-Fluoro-phenyl)-7-(3-piperidin-1-yl-propoxy)-1,2,3,4-tetrahydro-[2,6]-naphthyridine; |
| 33 | 4-(3-Chloro-4-fluoro-phenyl)-7-(3-piperidin-1-yl-propoxy)-1,2,3,4-tetrahydro-[2,6]-naphthyridine; |
| 34 | 4-(3-Fluoro-phenyl)-2-methyl-7-(3-piperidin-1-yl-propoxy)-1,2,3,4-tetrahydro-[2,6]-naphthyridine; |
| 35 | 4-(3-Chloro-4-fluoro-phenyl)-2-methyl-7-(3-piperidin-1-yl-propoxy)-1,2,3,4-tetrahydro-[2,6]naphthyridine; |
| 36 | 4-(4-Chloro-phenyl)-2-methyl-7-(3-piperidin-1-yl-propoxy)-1,2,3,4-tetrahydro-[2,6]-naphthyridine; |
| 37 | 4-(3,4-Dichloro-phenyl)-7-(1-isopropyl-piperidin-4-ylmethoxy)-1,2,3,4-tetrahydro-[2,6]naphthyridine; |
| 38 | 4-(3,4-Dichloro-phenyl)-2-methyl-7-(3-piperidin-1-yl-propoxy)-1,2,3,4-tetrahydro-[2,6]-naphthyridine (enantiomer A); |
| 39 | 4-(3,4-Dichloro-phenyl)-2-methyl-7-(3-piperidin-1-yl-propoxy)-1,2,3,4-tetrahydro-[2,6]-naphthyridine (enantiomer B); |
| 40 | 7-(1-Isopropyl-piperidin-4-ylmethoxy)-4-(4-methoxy-phenyl)-2-methyl-1,2,3,4-tetrahydro-[2,6]-naphthyridine; |
| 41 | 4-(3,4-Dichloro-phenyl)-7-(1-isopropyl-piperidin-4-ylmethoxy)-2-methyl-1,2,3,4-tetrahydro-[2,6]naphthyridine; |
| 42 | 4-(4-Methoxy-phenyl)-7-(piperidin-4-yloxy)-1,2,3,4-tetrahydro-[2,6]naphthyridine; |
| 43 | 4-(4-Methoxy-phenyl)-2-methyl-7-(1-methyl-piperidin-4-yloxy)-1,2,3,4-tetrahydro-[2,6]naphthyridine; |
| 44 | 7-(3-Piperidin-1-yl-propoxy)-4-(4-trifluoromethoxy-phenyl)-1,2,3,4-tetrahydro-[2,6]naphthyridine; |
| 45 | 4-(3,4-Dichloro-phenyl)-7-(3-piperidin-1-yl-propoxy)-1,2,3,4-tetrahydro-[2,6]-naphthyridine (enantiomer A); |
| 46 | 4-(3,4-Dichloro-phenyl)-7-(3-piperidin-1-yl-propoxy)-1,2,3,4-tetrahydro-[2,6]-naphthyridine (enantiomer B); |
| 47 | 7-(3-Morpholin-4-yl-propoxy)-4-phenyl-1,2,3,4-tetrahydro-[2,6]naphthyridine; |
| 48 | 8-(4-Methoxy-phenyl)-6-methyl-3-(4-piperidin-1-yl-but-1-ynyl)-5,6,7,8-tetrahydro-[1,6]naphthyridine; |
| 49 | 8-(4-Methoxy-phenyl)-6-methyl-3-(4-piperidin-1-yl-butyl)-5,6,7,8-tetrahydro-[1,6]-naphthyridine; |
| 50 | 5-(4-Methoxy-phenyl)-7-methyl-2-(3-piperidin-1-yl-propoxy)-5,6,7,8-tetrahydro-[1,7]naphthyridine; and |
| 51 | 5-(4-Methoxy-phenyl)-7-methyl-2-(4-piperidin-1-yl-but-1-ynyl)-5,6,7,8-tetrahydro-[1,7]naphthyridine. |

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety. Where chemical symbols are used, it is understood that they are read from left to right, and that otherwise their spatial orientation has no significance.

The compounds as described above may be made according to processes within the skill of the art and/or that are described in the schemes and examples that follow. To obtain the various compounds herein, starting materials may be employed that carry the ultimately desired substituents though the reaction scheme with or without protection as appropriate. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", $3^{rd}$ ed., John Wiley & Sons, 1999. The protecting groups may be removed at a convenient subsequent stage using methods known from the art. Alternatively, it may be necessary to employ, in the place of the ultimately desired substituent, a suitable group that may be carried through the reaction scheme and replaced as appropriate with the desired substituent. Such compounds, precursors, or prodrugs are also within the scope of the invention. Reactions may be performed between the melting point and the reflux temperature of the solvent, and preferably between 0° C. and the reflux temperature of the solvent.

The naphthyridine compounds of formula (I) may be prepared by a number of reaction schemes. Access to compounds of formula (I) is described in Schemes A-D. Persons skilled in the art will recognize that certain compounds are more advantageously produced by one scheme as compared to the other.

SCHEME A

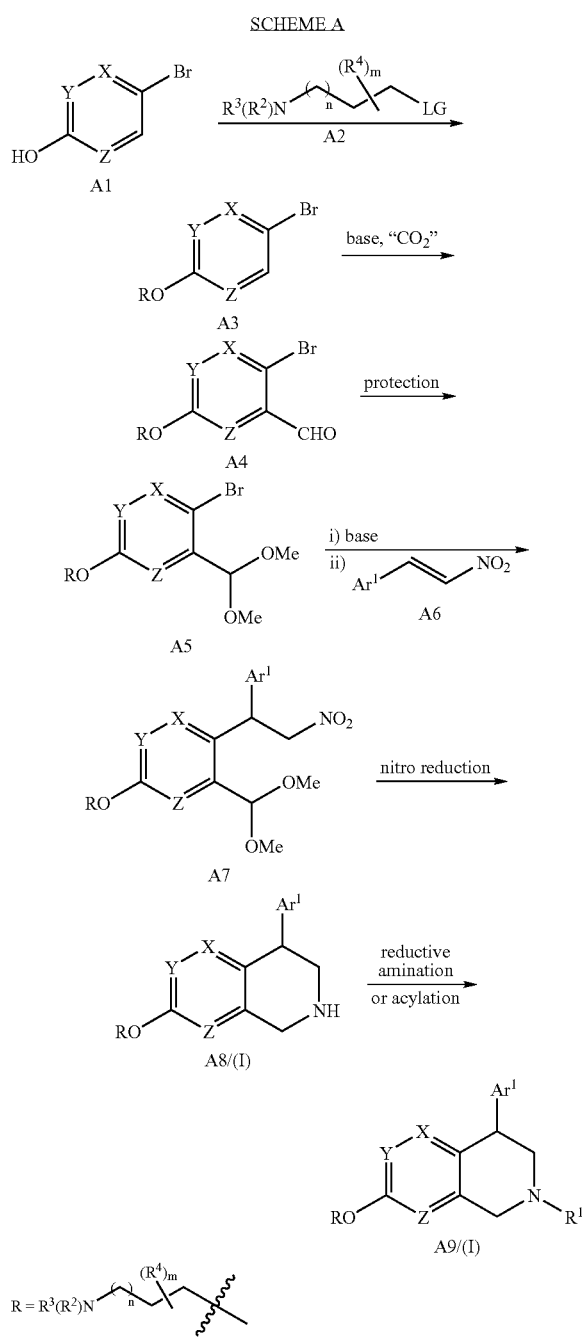

Referring to Scheme A, reagents of formulae A1, A2, and A6 are commercially available, or are prepared according to known methods. Derivatives A1 are reacted with alkylating agents A2, where LG is a halide or tosylate leaving group, using a suitable base such as NaH, at temperatures between −78° C. and room temperature, to form ethers A3. Alternatively, derivatives A1 may be reacted with alcohols A2 (where LG is OH) according to a Williamson ether synthesis protocol (using a suitable base such as $K_2CO_3$, $Na_2CO_3$, or NaH, in a solvent such as acetonitrile, with or without catalytic KI or NaI) or under Mitsunobu conditions. Ethers A3 are reacted with a strong base such as LDA, in a solvent such as THF, at reduced temperatures such as −78° C., and subsequently with a $CO_2$ equivalent, such as DMF, ethyl chloroformate, or the like, to install an aldehyde or related functionality that may be converted to aldehydes A4. Where Z is N, compounds A4 may be alternatively be prepared according to Kelly, S. A. et al. Org. Biomol. Chem. 2003, 1(16), 2865-2876. Aldehydes A4 may be protected as their acetal analogs A5 according to standard methods, such as treatment with $(MeO)_3CH$ and $H_2SO_4$ in MeOH. Acetals A5 may be also formed in situ or during purification of aldehydes A4. Acetals A5 are then reacted under halogen-metal exchange conditions, such as with BuLi, in a solvent such as THF or toluene, at reduced temperatures such as −78° C., and coupled with nitroolefins A6, to provide nitroalkanes A7. Where X is N, compounds of A7 may alternatively be prepared from 2-chloro-5-hydroxy-nicotinic acid (Nemec, J. et al. J. Het. Chem. 1974, 11(4), 569-573) using methods known in the art. Nitroalkanes are reduced, preferably by treatment with Zn in acetic acid at elevated temperatures, effecting cyclization to form naphthyridines A8. Formation of cyclized products may require treatment with a strong acid such as 6 N HCl, and/or reduction of an intermediate imine with a reducing agent such as $NaBH_4$ and the like. Compounds A8 may be further processed to other compounds of formula (I) by reductive amination or acylation. Other embodiments of $R^1$ may be introduced by acylation or peptide coupling protocols known to one skilled in the art.

SCHEME B

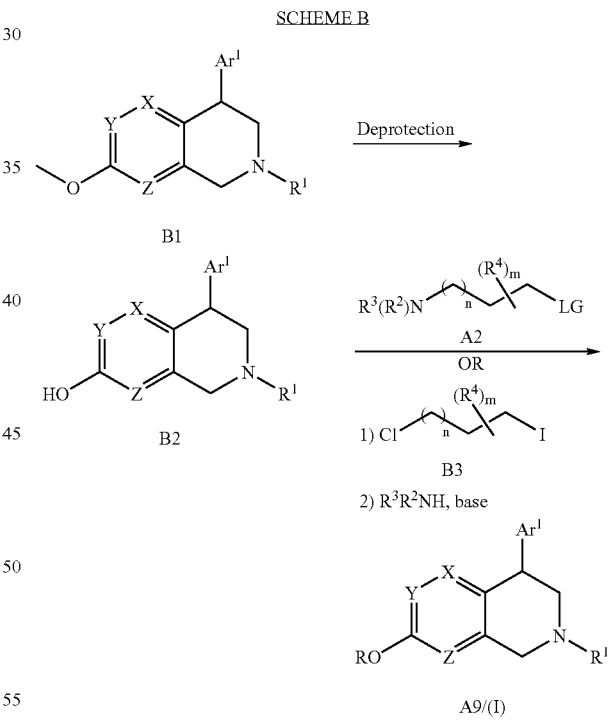

Referring to Scheme B, compounds of formula (I) may also be prepared from methyl ethers B1, which are accessible according to the methods described in Scheme A. Deprotection of the methyl group may be accomplished by treatment under acidic conditions, such as 4 M HCl at elevated temperatures or TMSCl/NaI. Alternatively, where the methoxy group is not ortho to a ring N, deprotection may be effected by treatment with $BBr_3$. The resulting alcohols B2 may be alkylated or coupled with alkylating agents A2 as described in Scheme A. Alternatively, alcohols B2 may be alkylated with alkyl iodides B3, using a base such as NaH, in a solvent such as DMF or THF or mixtures thereof; the resulting intermediate alkyl chlorides (not shown) may be displaced with suitable amines R³R²NH, in the presence of a base such as Na₂CO₃, in a polar solvent such as n-butanol, with or without catalytic NaI, to form compounds of formula (I).

SCHEME C

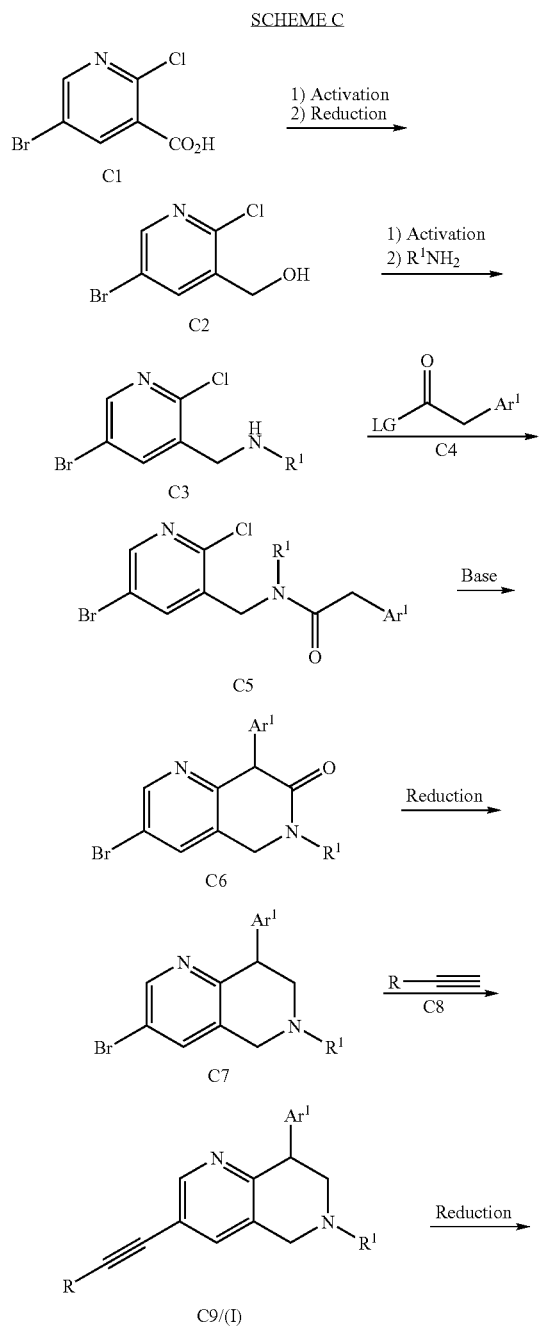

-continued

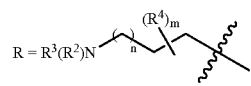

Referring to Scheme C, acid C1 is commercially available or may be prepared according to the procedures described by Gero, T. W. et al. (Synth. Commun. 1989, 19(3-4), 553-559). The acid functionality is reduced using conditions known to one skilled in the art. Preferred conditions involve: first converting the acid to a carbonate, such as an isobutyl carbonate, by treatment with isobutyl chloroformate in the presence of a tertiary amine base such as Et₃N, in a solvent such as THF; and then reducing the intermediate with a suitable reducing agent such as NaBH₄. Alcohols C2 are then converted to amines C3 by: first converting alcohol functionality into a suitable leaving group such as a mesylate or halide, and preferably to the corresponding mesylates through treatment with MsCl, in the presence of a tertiary amine base such as Et₃N or DIPEA, in a solvent such as CH₂Cl₂ or THF; and then displacing the leaving group with amines R¹NH₂, with or without the addition of a base such as Et₃N, Na₂CO₃, K₂CO₃, or excess R¹NH₂, in a polar solvent such as EtOH or n-butanol. One skilled in the art will recognize that where the ultimately desired R¹ is an acyl group, a suitable nitrogen protecting group, such as a benzyl protecting group, may be installed at this stage, and subsequently removed and replaced with the appropriate acyl group at the end of the sequence as described in Scheme A. Amines C3 may then be reacted with acylating agents C4 to form amides C5. Where LG is a halide, such as chloride, reactions include treatment with a suitable tertiary amine base, such as Et₃N or N-methylmorpholine, in a solvent such as CH₂Cl₂ or THF. Where LG is OH, coupling is effected under peptide coupling conditions known in the art. Cyclization to form compounds C6 is performed in the presence of a strong base, such as NaH, in a polar, aprotic solvent such as DMSO. Reduction of compounds C6, using a reducing agent such as BH₃, in a solvent such as THF, provides aryl bromides C7. Preferably, reductions are performed at elevated temperatures. Bromides C7 may then be coupled with alkynes C8, under Sonogashira or other palladium-catalyzed conditions, to provide alkynes C9, which are embodiments of formula (I). Preferred conditions include a palladium catalyst such as (Ph₃P)₂PdCl₂, with or without additives such as Et₂NH, CuI, and Ph₃P, or the like, in a polar solvent such as DMF or NMP. Preferably, reactions are performed at elevated temperatures. Alkynes C9 may then be hydrogenated, in the presence of a suitable catalyst such as Pd on BaSO4, in a solvent such as EtOH, to form alkanes C10, which are embodiments of formula (I).

SCHEME D

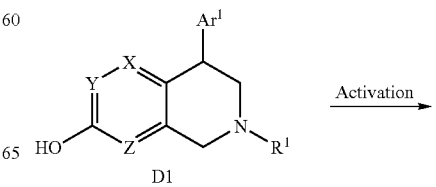

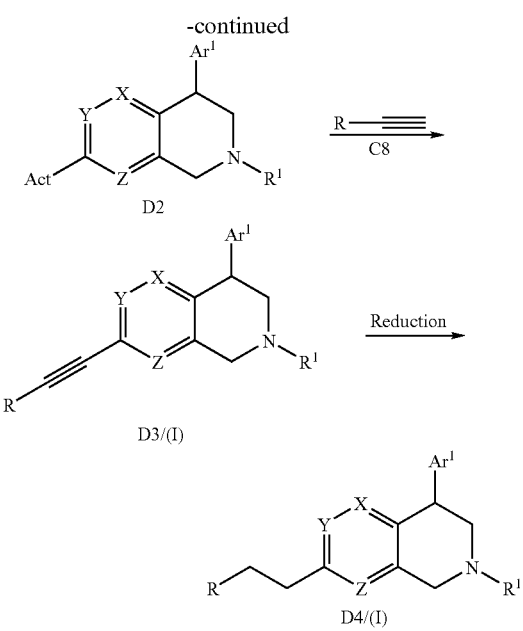

Referring to Scheme D, alcohols D1 may be prepared according to the methods described in Scheme A and B, and may be activated to an aryl chloride, aryl bromide, or aryl triflate by treatment with a reagent such as POCl$_3$ or triflic anhydride to form chlorides D2. Preferably, reactions are performed with POCl$_3$ at elevated temperatures. Activated compounds D2 may be coupled with alkynes C8 and reduced to form alkynes D3 and alkanes D4, respectively, as described in Scheme C.

Those skilled in the art will recognize that, if required, a group such as a protected amino group or surrogate, may be used in place of "R" and later transformed into the group "R".

Compounds prepared according to the schemes described above may be obtained as single enantiomers, diastereomers, or regioisomers, or as racemic mixtures or mixtures of enantiomers, diastereomers, or regioisomers. Where regioisomeric or diastereomeric mixtures are obtained, isomers may be separated using conventional methods such as chromatography or crystallization. Where racemic (1:1) and non-racemic (not 1:1) mixtures of enantiomers are obtained, single enantiomers may be isolated using conventional separation methods known to one skilled in the art. Particularly useful separation methods may include chiral chromatography, recrystallization, resolution, diastereomeric salt formation, or derivatization into diastereomeric adducts followed by separation.

For therapeutic use, salts of the compounds of the present invention are those that are pharmaceutically acceptable. However, salts of acids and bases that are non-pharmaceutically acceptable may also find use, for example, in the preparation or purification of a pharmaceutically acceptable compound. All salts, whether pharmaceutically acceptable or not are included within the ambit of the present invention.

Pharmaceutically acceptable salts, esters, and amides of compounds according to the present invention refer to those salt, ester, and amide forms of the compounds of the present invention which would be apparent to the pharmaceutical chemist, i.e., those which are non-toxic and which would favorably affect the pharmacokinetic properties of said compounds of the present invention. Those compounds having favorable pharmacokinetic properties would be apparent to the pharmaceutical chemist, i.e., those which are non-toxic and which possess such pharmacokinetic properties to provide sufficient palatability, absorption, distribution, metabolism and excretion. Other factors, more practical in nature, which are also important in the selection, are cost of raw materials, ease of crystallization, yield, stability, hygroscopicity and flowability of the resulting bulk drug.

Examples of acids that may be used in the preparation of pharmaceutically acceptable salts include the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Compounds of the present invention containing acidic protons may be converted into their therapeutically active non-toxic metal or amine addition salt forms by treatment with appropriate organic and inorganic bases. Appropriate base salt forms comprise, for example, the ammonium salts; the alkali and earth alkaline metal salts (e.g. lithium, sodium, potassium, magnesium, calcium salts, which may be prepared by treatment with, for example, magnesium hydroxide, calcium hydroxide, potassium hydroxide, zinc hydroxide, or sodium hydroxide); and amine salts made with organic bases (e.g. primary, secondary and tertiary aliphatic and aromatic amines such as L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine). See, e.g., S. M. Berge, et al., "Pharmaceutical Salts", J. Pharm. Sci., 1977, 66:1-19, which is incorporated herein by reference.

Pharmaceutically acceptable esters and amides are those that are within a reasonable benefit/risk ratio, pharmacologically effective and suitable for contact with the tissues of patients without undue toxicity, irritation, or allergic response. Representative pharmaceutically acceptable amides of the invention include those derived from ammonia, primary $C_{1-6}$alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl)amines.

Representative pharmaceutically acceptable esters of the invention include $C_{1-7}$alkyl, $C_{5-7}$cycloalkyl, phenyl, substituted phenyl, and phenyl$C_{1-6}$alkyl- esters. Preferred esters include methyl esters. Furthermore, examples of suitable esters include such esters where one or more carboxyl substituents is replaced with p-methoxybenzyloxy-carbonyl, 2,4, 6-trimethyl benzyloxy-carbonyl, 9-anthryloxycarbonyl, $CH_3SCH_2COO$—, tetrahydrofur-2-yloxycarbonyl, tetrahydropyran-2-yloxy-carbonyl, fur-2-yloxycarbonyl, benzoylmethoxycarbonyl, p-nitrobenzyloxy-carbonyl, 4-pyridyl methoxycarbonyl, 2,2,2-trichloroethoxycarbonyl, 2,2,2-tribromoethoxycarbonyl, t-butyloxycarbonyl, t-amyloxycarbonyl, diphenylmethoxycarbonyl, triphenylmethoxycarbonyl, adamantyloxycarbonyl, 2-benzyloxyphenyloxycarbonyl, 4-methylthiophenyloxycarbonyl, or tetrahydropyran-2-yloxycarbonyl.

The compounds of the present invention are modulators of the histamine $H_3$ receptor and of the serotonin transporter, and as such, the compounds are useful in the treatment of histamine $H_3$ and serotonin-mediated disease states. Compounds of the present invention possess serotonin transporter and $H_3$ receptor modulating activity. As modulators, the compounds may act as antagonists or agonists. The effect of an antagonist may also be produced by an inverse agonist.

The compounds of the present invention are useful in methods for treating or preventing neurologic or CNS disorders including sleep/wake and arousal/vigilance disorders (e.g. insomnia, jet lag, and disturbed sleep), attention deficit hyperactivity disorders (ADHD), attention-deficit disorders, learning and memory disorders, learning impairment, memory impairment, memory loss, cognitive dysfunction, migraine, neurogenic inflammation, dementia, mild cognitive impairment (pre-dementia), Alzheimer's disease, epilepsy, narcolepsy with or without associated cataplexy, cataplexy, disorders of sleep/wake homeostasis, idiopathic somnolence, excessive daytime sleepiness (EDS), circadian rhythym disorders, sleep/fatigue disorders, fatigue, drowsiness associated with sleep apnea, sleep impairment due to perimenopausal hormonal shifts, Parkinson's-related fatigue, MS-related fatigue, depression-related fatigue, chemotherapy-induced fatigue, work-related fatigue, eating disorders, obesity, motion sickness, vertigo, schizophrenia, substance abuse, bipolar disorders, manic disorders and depression. Said methods comprise the step of administering to a mammal suffering therefrom an effective amount of at least one compound of the present invention.

Particularly, as modulators of the histamine $H_3$ receptor and the serotonin transporter, the compounds of the present invention may be used in the treatment or prevention of depression, disturbed sleep, fatigue, lethargy, cognitive impairment, memory impairment, memory loss, learning impairment, and attention-deficit disorders.

The present invention also contemplates a method of treating or preventing a disease or condition mediated by the histamine $H_3$ receptor and the serotonin transporter with a combination therapy, comprising administering at least one compound of the present invention in combination with one or more therapeutic agents. Suitable therapeutic agents include: $H_1$ receptor antagonists, $H_2$ receptor antagonists, $H_3$ receptor antagonists, and neurotransmitter modulators such as serotonin-norepinephrine reuptake inhibitors, selective serotonin reuptake inhibitors (SSRIs), noradrenergic reuptake inhibitors, non-selective serotonin re-uptake inhibitors (NSSRIs), and modafinil. In a particular embodiment, a combination therapy method includes administering at least one compound of the present invention and administering modafinil, for example, for the treatment of narcolepsy, excessive daytime sleepiness (EDS), Alzheimer's disease, depression, attention-deficit disorders, MS-related fatigue, post-anesthesia grogginess, cognitive impairment, schizophrenia, spasticity associated with cerebral palsy, age-related memory decline, idiopathic somnolence, or jet-lag.

Compounds of the present invention may be administered in pharmaceutical compositions to treat patients (humans and other mammals) with disorders mediated by the $H_3$ receptor and serotonin transporter. Thus, the invention features pharmaceutical compositions containing at least one compound of the present invention and a pharmaceutically acceptable carrier. A composition of the invention may further include at least one other therapeutic agent (for example, a combination formulation or combination of differently formulated active agents for use in a combination therapy method).

The present invention also features methods of using or preparing or formulating such pharmaceutical compositions. The pharmaceutical compositions can be prepared using conventional pharmaceutical excipients and compounding techniques known to those skilled in the art of preparing dosage forms. It is anticipated that the compounds of the invention can be administered by oral, parenteral, rectal, topical, or ocular routes, or by inhalation. Preparations may also be designed to give slow release of the active ingredient. The preparation may be in the form of tablets, capsules, sachets, vials, powders, granules, lozenges, powders for reconstitution, liquid preparations, or suppositories. Preferably, compounds may be administered by intravenous infusion or topical administration, but more preferably by oral administration.

For oral administration, the compounds of the invention can be provided in the form of tablets or capsules, or as a solution, emulsion, or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives agents. Suitable inert fillers include sodium and calcium carbonate, sodium and calcium phosphate, lactose, starch, sugar, glucose, methyl cellulose, magnesium stearate, mannitol, sorbitol, and the like; typical liquid oral excipients include ethanol, glycerol, water and the like. Starch, polyvinyl-pyrrolidone, sodium starch glycolate, microcrystalline cellulose, and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate to delay absorption in the gastrointestinal tract, or may be coated with an enteric coating. Capsules for oral use include hard gelatin capsules in which the active ingredient is mixed with a solid, semi-solid, or liquid diluent, and soft gelatin capsules wherein the active ingredient is mixed with water, an oil such as peanut oil or olive oil, liquid paraffin, a mixture of mono and di-glycerides of short chain fatty acids, polyethylene glycol 400, or propylene glycol.

Liquids for oral administration may be suspensions, solutions, emulsions or syrups or may be presented as a dry product for reconstitution with water or other suitable vehicles before use. Compositions of such liquid may contain pharmaceutically-acceptable excipients such as suspending agents (for example, sorbitol, methyl cellulose, sodium alginate, gelatin, hydroxyethylcellulose, carboxymethylcellulose, aluminium stearate gel and the like); non-aqueous vehicles, which include oils (for example, almond oil or fractionated coconut oil), propylene glycol, ethyl alcohol or water; preservatives (for example, methyl or propyl p-hydroxybenzoate or sorbic acid); wetting agents such as lecithin; and, if needed, flavoring or coloring agents.

The compounds of this invention may also be administered by non-oral routes. The compositions may be formulated for rectal administration as a suppository. For parenteral use, including intravenous, intramuscular, intraperitoneal, or subcutaneous routes, the compounds of the invention will generally be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit dose form such as ampules or disposable injection devices, in multi-dose forms such as vials from which the appropriate dose may be withdrawn, or in a solid form or pre-concentrate that can be used to prepare an injectable formulation. Another mode of administration of the compounds of the invention may utilize a patch formulation to affect transdermal delivery. The compounds of this invention may also be administered by inhalation, via the nasal or oral routes using a spray formulation consisting of the compound of the invention and a suitable carrier.

Methods are known in the art for determining effective doses for therapeutic and prophylactic purposes for the pharmaceutical compositions or the drug combinations of the present invention, whether or not formulated in the same composition. The specific dosage level required for any particular patient will depend on a number of factors, including severity of the condition being treated, the route of administration, and the weight of the patient. For therapeutic purposes, "effective dose" or "effective amount" refers to that amount of each active compound or pharmaceutical agent, alone or in combination, that elicits the biological or medicinal response in a tissue system, animal, or human that is being sought by a researcher, veterinarian, medical doctor, or other clinician, which includes alleviation of the symptoms of the disease or disorder being treated. For prophylactic purposes (i.e., inhibiting the onset or progression of a disorder), the term "effective dose" or "effective amount" refers to that amount of each active compound or pharmaceutical agent, alone or in combination, that inhibits in a subject the onset or progression of a disorder as being sought by a researcher, veterinarian, medical doctor, or other clinician, the delaying of which disorder is mediated, at least in part, by the modulation of the histamine $H_3$ receptor and/or the serotonin transporter. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together. Combinations of three or more drugs are analogously possible. Methods of combination therapy include co-administration of a single formulation containing all active agents; essentially contemporaneous administration of more than one formulation; and administration of two or more active agents separately formulated.

It is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

Preferably, oral doses range from about 0.05 to 200 mg/kg, daily, taken in 1 to 4 separate doses. Some compounds of the invention may be orally dosed in the range of about 0.05 to about 50 mg/kg daily, others may be dosed at 0.05 to about 20 mg/kg daily, while still others may be dosed at 0.1 to about 10 mg/kg daily. Infusion doses can range from about 1 to 1000 µg/kg/min of inhibitor, admixed with a pharmaceutical carrier over a period ranging from several minutes to several days. For topical administration compounds of the present invention may be mixed with a pharmaceutical carrier at a concentration of about 0.1% to about 10% of drug to vehicle.

EXAMPLES

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention.

Protocol for Preparative Reversed-Phase HPLC

| | | |
|---|---|---|
| Instrument: Gilson ® | | |
| Column: YMC-Pack ODS-A, 5 µm, 75 × 30 mm | | |
| Flow rate: 25 mL/min | | |
| Detection: $\lambda$ = 220 & 254 nm | | |
| Gradient ($CH_3CN/H_2O$, 0.05% trifluoroacetic acid) | | |
| 1) | 0.0 min | 15% $CH_3CN$/85% $H_2O$ |
| 2) | 20.0 min | 99% $CH_3CN$/1% $H_2O$ |

Protocol for HPLC (Reversed-Phase)

| | | |
|---|---|---|
| Method A: | | |
| Instrument: Hewlett Packard Series 1100 | | |
| Column: Agilent ZORBAX ® Bonus RP, 5 µm, 4.6 × 250 mm | | |
| Flow rate: 1 mL/min | | |
| Detection: $\lambda$ = 220 & 254 nm | | |
| Gradient ($CH_3CN/H_2O$, 0.05% trifluoroacetic acid) | | |
| 1) | 0.0 min | 1% $CH_3CN$/99% $H_2O$ |
| 2) | 20.0 min | 99% $CH_3CN$/1% $H_2O$ |

| | | |
|---|---|---|
| Method B: | | |
| Instrument: Hewlett Packard HPLC | | |
| Column: Agilent ZORBAX ® Eclipse XDB-C8, 5 µm, 4.6 × 150 mm | | |
| Flow rate: 1 mL/min | | |
| Detection: $\lambda$ = 220 & 254 nm | | |
| Gradient ($CH_3CN/H_2O$, 0.05% trifluoroacetic acid) | | |
| 1) | 0.0 min | 1% $CH_3CN$/99% $H_2O$ |
| 2) | 8.0 min | 99% $CH_3CN$/1% $H_2O$ |
| 3) | 12.0 min | 99% $CH_3CN$/1% $H_2O$ |

Protocol for Preparative SFC

Instrument: Thar Technologies®
Column: Chiracel AD, 10 µm, 250×20 mm
Flow rate: 37 gm/min
Detection: λ=220 & 254 nm
Mobile phase: Isocratic 30% IPA/70% $CO_2$
Pressure: 150 Bar
Temperature: 35° C.

Protocol for Analytical SFC

Instrument: Jasco®
Column: Chiracel AD, 10 µm, 250×4.6 mm
Flow rate: 1 gm/min
Detection: λ=220 & 254 nm
Mobile phase: Isocratic 30% IPA/70% $CO_2$
Pressure: 150 Bar
Temperature: 35° C.

Mass spectra were obtained on an Agilent series 1100 MSD using electrospray ionization (ESI) in either positive or negative modes as indicated. Calculated mass corresponds to the exact mass.

Thin-layer chromatography was performed using Merck silica gel 60 $F_{254}$ 2.5 cm×7.5 cm 250 µm or 5.0 cm×10.0 cm 250 µm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Normal phase flash column chromatography (FCC) was typically performed with RediSep® silica gel columns.

Chiral chromatography was performed using SFC HPLC (Chiralpak AD-h column), IPA/MeOH/$CO_2$, or by chiral HPLC (21×250 mm Chiracel AD-H, 5 µM (Chiral Technologies), 0.2% diethylamine in EtOH, 8 mL/min).

Where a potential chiral center is designated with a solid bond (not bold or hashed), the structure is meant to refer to a racemic mixture, a mixture of enantiomers, or a single enantiomer as described. Where a single enantiomer is described without enantiomeric designation at the chiral center, it is understood that the absolute configuration of the single enantiomer is unknown.

Unless otherwise specified, solutions were dried over $Na_2SO_4$, and were concentrated using a rotary evaporator under reduced pressure.

Example 1

4-(2-Fluoro-phenyl)-7-(3-piperidin-1-yl-propoxy)-1,2,3,4-tetrahydro-[2,6]naphthyridine

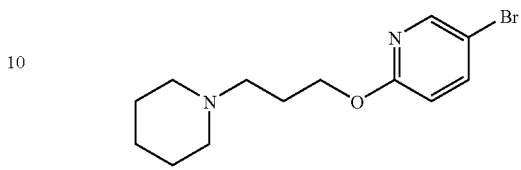

Step A. 5-Bromo-2-(3-piperidin-1-yl-propoxy)-pyridine. A solution of 3-piperidin-1-yl-propan-1-ol (5.8 mL, ~4.6 g, 32.2 mmol) in DMF (250 mL) was treated with NaH (60% in oil; 2.58 g, 67.3 mmol). The mixture was stirred at room temperature (rt) for 1 h, and then was treated with 2,5-dibromopyridine (6.81 g, 28.7 mmol). After 18 h, MeOH (10 mL) was added slowly, and the mixture was diluted with satd. aq. $NaHCO_3$, and extracted with EtOAc (2×). The organic layers were combined, washed with $H_2O$ (3×), dried, and concentrated to give oil. The residue was purified ($SiO_2$; 2 M $NH_3$ in MeOH/DCM) to give the title compound (7.38 g, 86%) as an off-white solid. MS (ESI): mass calcd. for $C_{13}H_{19}BrN_2O$, 298.07; m/z found, 299.3 $[M+H]^+$. $^1$H NMR ($CDCl_3$): 8.17 (dd, J=2.5, 0.6, 1H), 7.62 (dd, J=8.8, 2.5, 1H), 6.64 (dd, J=8.8, 0.6, 1H), 4.28 (t, J=6.5, 2H), 2.47-2.33 (m, 6H), 2.00-1.90 (m, 2H), 1.62-1.56 (m, 4H), 1.47-1.40 (m, 2H).

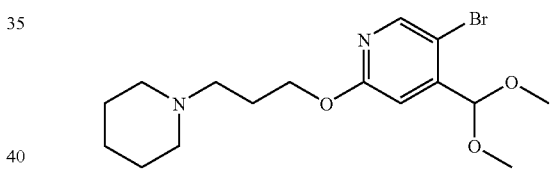

Step B. 5-Bromo-4-dimethoxymethyl-2-(3-piperidin-1-yl-propoxy)-pyridine. A −78° C. of $iPr_2NH$ (1.7 mL, 12.2 mmol) in THF (35 mL) was treated with n-BuLi (2.5 M in hexanes; 4.8 mL). The mixture was allowed to warm to 0° C., then was cooled to −78° C. and treated with a pre-cooled, 0° C. solution of 5-bromo-2-(3-piperidin-1-yl-propoxy)-pyridine (3.60 g, 12.0 mmol) in THF (25 mL) via cannula. After 30 min, DMF (1.8 mL, 23.3 mmol) was added, and the mixture was allowed to warm to 0° C. The mixture was diluted with satd. aq. $NaHCO_3$ and extracted with DCM. The organic layer was dried and concentrated to give an oil. The oil was purified ($SiO_2$; 2 M $NH_3$ in MeOH/DCM) to give a mixture of the aldehyde and a methanol hemi-acetal, which was used directly in the next step. A 0° C. solution of the mixture in MeOH (20 mL) was treated with conc. $H_2SO_4$ (1 mL). After 2.5 days at 0° C., the mixture was concentrated, neutralized with satd. aq. $NaHCO_3$, and extracted with DCM. The organic layer was dried and concentrated. The crude mixture was chromatographed ($SiO_2$; 1-10% 2 M $NH_3$ in MeOH/DCM) to give the title compound (1.66 g, 37%) as an oil. MS (ESI): mass calcd. for $C_{16}H_{25}BrN_2O_3$, 372.10; m/z found, 373.40 $[M+H]^+$. $^1$H NMR ($CDCl_3$): 8.21 (s, 1H), 6.98 (s, 1H), 4.29 (t, J=6.5, 2H), 3.38 (s, 6H), 2.48-2.35 (m, 6H), 2.00-1.92 (m, 4H), 1.47-1.40 (m, 2H).

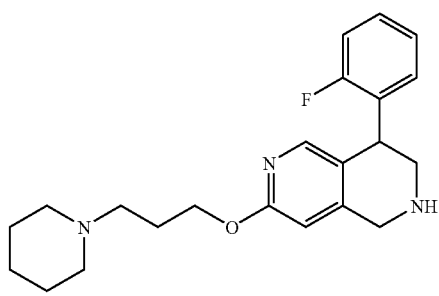

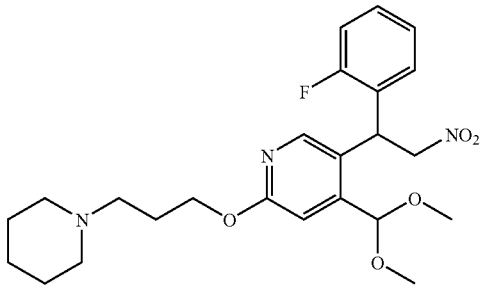

Step C. 1-(3-{3-Dimethoxymethyl-4-[1-(2-fluoro-phenyl)-2-nitro-ethyl]-phenoxy}-propyl)-piperidine. A −78° C. solution of 5-bromo-4-dimethoxymethyl-2-(3-piperidin-1-yl-propoxy)-pyridine (359 mg, 0.962 mmol) in THF (8 mL) was treated with n-BuLi (2.5 M in hexanes; 0.4 mL). After 20 min at −78° C., the mixture was treated with a solution of 1-fluoro-2-(2-nitro-vinyl)-benzene (171 mg, 1.02 mmol) in THF (5 mL). After 20 min at −78° C., the mixture was treated with acetic acid (1 mL) and was allowed to warm to 0° C. The mixture was concentrated and the residue was chromatographed (SiO$_2$; 1-10% 2 M NH$_3$ in MeOH/DCM) to give the title compound (285 mg, 64%) as an oil. MS (ESI): mass calcd. for C$_{24}$H$_{32}$FN$_3$O$_5$, 461.23; m/z found, 462.5 [M+H]$^+$. $^1$H NMR (CDCl$_3$): 8.03 (s, 1H), 7.30-7.24 (m, 2H), 7.15-7.03 (m, 2H), 6.95 (s, 1H), 5.55 (t, 8.2, 1H), 5.43 (s, 1H), 5.02-4.92 (m, 2H), 4.34-4.27 (m 2H), 3.35 (s, 3H), 3.27 (s, 3H), 2.55-2.42 (m, 6H), 2.05-1.95 (m, 2H), 1.69-1.60 (m, 4H), 1.49-1.42 (m, 2H).

Step D. A solution of 1-(3-{3-dimethoxymethyl-4-[1-(2-fluoro-phenyl)-2-nitro-ethyl]-phenoxy}-propyl)-piperidine (280 mg, 0.607 mmol) in acetic acid (5 mL) was treated with Zn powder (308 mg, 4.7 mmol), and the resulting mixture was heated at 40° C. for 16 h. The mixture was cooled to 0° C. and filtered, washing with MeOH. The filtrated was concentrated, and the resulting oil was treated with 6 N HCl at 0° C. for 3 d. The mixture was neutralized by the slow addition of satd. aq. NaHCO$_3$, and then was extracted with DCM. The organic layer was dried and concentrated. The crude material was chromatographed (SiO$_2$; 1-10% 2 M NH$_3$ in MeOH/DCM) to give the title compound (60.9 mg, 27%) as an oil. MS (ESI): mass calcd. for C$_{22}$H$_{28}$FN$_3$O, 369.22; m/z found, 370.5 [M+H]$^+$. $^1$H NMR (CDCl$_3$): 7.71 (s, 1H), 7.26-7.17 (m, 1H), 7.10-7.00 (m, 2H), 6.88-6.80 (m, 1H), 6.47 (s, 1H), 4.41 (t, J=5.1, 1H), 4.27 (t, J=6.5, 1H), 4.08 (d, J=17.4, 1H), 4.01 (d, J=17.2, 1H), 3.34 (dd, J=13.2, 5.0, 1H), 3.14 (dd, J=13.1, 5.7, 1H), 2.49-2.35 (m, 6H), 2.00-1.91 (m, 2H), 1.64-1.54 (m, 4H), 1.47-1.39 (m, 2H).

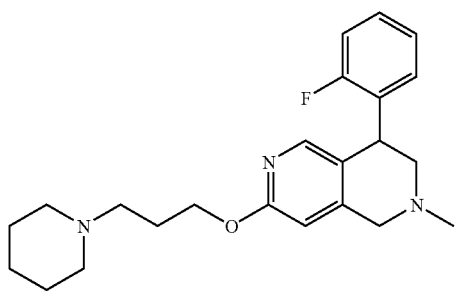

Example 2

4-(2-Fluoro-phenyl)-2-methyl-7-(3-piperidin-1-yl-propoxy)-1,2,3,4-tetrahydro-[2,6]-naphthyridine A solution of 4-(2-fluoro-phenyl)-7-(3-piperidin-1-yl-propoxy)-1,2,3,4-tetrahydro-[2,6]naphthyridine (50.2 mg, 0.136 mmol) in MeOH (5 mL) was treated with paraformaldehyde (62 mg). The mixture was heated at 55° C. for 1 h, cooled to 0° C., and was treated with NaBH$_4$ (66 mg, 1.74 mmol). After 2 h at 0° C., the mixture was diluted with satd. aq. NaHCO$_3$ and extracted with DCM. The organic layer was dried and concentrated. The residue was chromatographed (SiO$_2$; 1-10% 2 M NH$_3$ in MeOH/DCM) to give the title compound (20.4 mg, 39%) as an oil. MS (ESI): mass calcd. for C$_{23}$H$_{30}$FN$_3$O, 383.24; m/z found, 384.5 [M+H]$^+$. $^1$H NMR (CDCl$_3$): 7.69 (s, 1H), 7.23-7.17 (m, 1H), 6.47 (s, 1H), 4.57-4.54 (m, 1H), 4.26 (t, J=6.7, 2H), 3.62 (d, J=15.9, 1H), 3.58 (d, J=15.9, 1H), 2.97 (dd, J=12.0, 5.1, 1H), 2.65 (dd, J=11.5, 7.5, 1H), 2.47-2.36 (m, 9H), 1.98-1.91 (m, 2H), 1.61-1.55 (m, 4H), 1.47-1.39 (m, 2H).

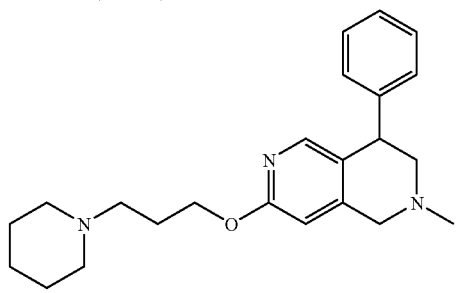

Example 3

2-Methyl-4-phenyl-7-(3-piperidin-1-yl-propoxy)-1,2,3,4-tetrahydro-[2,6]-naphthyridine

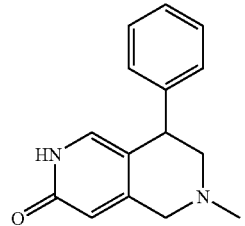

Step A. 6-Methyl-8-phenyl-5,6,7,8-tetrahydro-2H-[2,6]naphthyridin-3-one. A 0° C. solution of 7-methoxy-2-methyl-4-phenyl-1,2,3,4-tetrahydro-[2,6]naphthyridine (74.5 mg, 0.293 mmol) in CH$_3$CN (1 mL) was treated with TMSCl (1 mL) and NaI (~10 mg). The resulting mixture was stirred at 0° C. for 30 min, then at 50° C. for 18 h. The mixture was concentrated, diluted with satd. aq. NaHCO$_3$ and extracted with DCM. The organic layer was dried and concentrated. $^1$H NMR indicated ~30% conversion to the desired product. The material was diluted with CH$_3$CN (2 mL), treated with TMSCl (1 mL) and NaI (~10 mg) and heated at 60° C. for 18 h. The mixture was concentrated, neutralized with satd. aq. NaHCO$_3$ and extracted with DCM. The organic layer was dried and concentrated. The crude mixture was chromatographed (SiO$_2$; 1-10% 2 M NH$_3$ in MeOH/DCM) to give the title compound (29.6 mg, 42%). $^1$H NMR (CDCl$_3$): 7.33-7.23 (m, 3H), 7.20-7.16 (m, 2H), 6.83 (s, 1H), 6.26 (s, 1H), 4.06-4.00 (m, 1H), 3.73 (d, J=15.9, 1H), 3.40 (d, J=15.2, 1H), 3.03-2.97 (m, 1H), 2.46 (dd, J=11.6, 10.0, 1H), 2.41 (s, 3H).

Step B. A solution of 6-methyl-8-phenyl-5,6,7,8-tetrahydro-2H-[2,6]naphthyridin-3-one (82.8 mg, 0.326 mmol) in DMF (3 mL) and THF (2 mL) was treated with NaH (60% in oil; 62 mg). After 30 min, 1-chloro-3-iodopropane (0.075 mL) was added. After 1 h at 0° C., the mixture was diluted with satd. aq. NaHCO₃ and extracted with DCM. The organic layer was washed with H₂O (2×), dried, and concentrated. The residue was diluted with n-butanol (5 mL) and treated with piperidine (1.5 mL), Na₂CO₃ (150 mg), and KI (~10 mg). After 18 h at 55° C., the mixture was cooled, concentrated, neutralized with satd. aq. NaHCO₃, and extracted with DCM. The organic layer was dried and concentrated. Preparative TLC (SiO₂; 10% 2 M NH₃ in MeOH/DCM) gave the title compound (2.5 mg, 2%). ¹H NMR (CDCl₃): 7.34-7.19 (m, 5H), 6.84 (s, 1H), 6.31 (s, 1H), 4.05-4.00 (m, 1H), 3.88-3.82 (m, 2H), 3.66 (d, J=15.9, 1H), 3.40 (d, J=16.0, 1H), 2.99-2.93 (m, 1H), 2.46-2.40 (m, 1H), 2.39 (s, 3H), 2.55-2.06 (m, 6H), 1.87-1.74 (m, 2H), 1.46-1.33 (m, 6H). 6-Methyl-8-phenyl-2-(3-piperidin-1-yl-propyl)-5,6,7,8-tetrahydro-2H-[2,6]naphthyridin-3-one (22.6 mg, 19%) was also obtained. ¹H NMR (CDCl₃): 7.65 (s, 1H), 7.32-7.17 (m, 5H), 6.45 (s, 1H), 4.27-4.18 (m, 3H), 3.65 (d, J=15.7, 1H), 3.53 (d, J=15.6, 1H), 3.04-2.99 (m, 1H), 2.58-2.37 (m, 9H), 2.00-1.91 (m, 2H), 1.70-1.54 (m, 5H), 1.47-1.40 (m, 2H).

The compounds in Examples 4-47 were prepared by the methods described above.

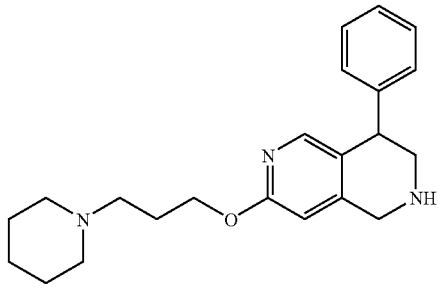

Example 4

4-Phenyl-7-(3-piperidin-1-yl-propoxy)-1,2,3,4-tetrahydro-[2,6]naphthyridine

MS (ESI): mass calcd. for C₂₂H₂₉N₃O, 351.23; m/z found, 352.5 [M+H]⁺. ¹H NMR (CDCl₃): 7.71 (s, 1H), 7.33-7.20 (m, 3H) 7.11-7.07 (m, 2H), 6.46 (s, 1H), 4.27 (t, J=6.5, 2H), 4.11-3.99 (m, 3H), 3.36 (dd, J=13.9, 5.1, 1H), 3.08 (dd, J=13.2, 6.3, 1H), 2.51-2.37 (m, 6H), 2.01-1.91 (m, 2H), 1.65-1.56 (m, 4H), 1.47-1.41 (m, 2H).

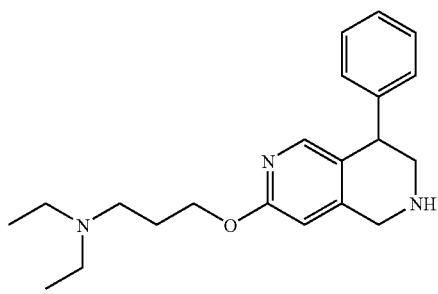

Example 5

Diethyl-[3-(8-phenyl-5,6,7,8-tetrahydro-[2,6]naphthyridin-3-yloxy)-propyl]-amine MS (ESI): mass calcd. for C₂₁H₂₉N₃O, 339.23; m/z found, 340.5 [M+H]⁺. ¹H NMR (CDCl₃): 7.71 (s, 1H), 7.32-7.21 (m, 2H), 7.11-7.07 (m, 2H), 6.46 (s, 1H), 4.26 (t, J=6.4, 2H), 4.12-3.99 (m, 3H), 3.36 (dd, J=13.3, 5.1, 1H), 3.08 (dd, J=13.1, 6.5, 1H), 2.63-2.50 (m, 6H), 1.95-1.86 (m, 2H), 1.07-1.00 (m, 6H).

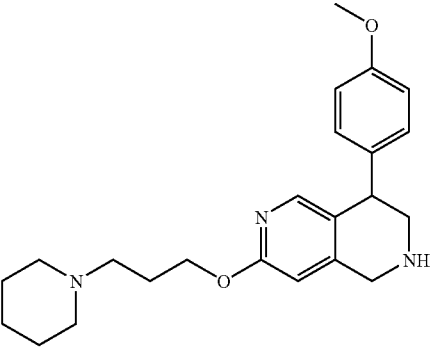

Example 6

4-(4-Methoxy-phenyl)-7-(3-piperidin-1-yl-propoxy)-1,2,3,4-tetrahydro-[2,6]-naphthyridine MS (ESI): mass calcd. for C₂₃H₃₁N₃O₂, 381.24; m/z found, 382.5 [M+H]⁺. ¹H NMR (CDCl₃): 7.71 (s, 1H), 7.02-6.99 (m, 2H), 6.86-6.82 (m, 2H), 6.45 (s, 1H), 4.26 (t, J=6.4, 2H), 4.10-3.97 (m, 3H), 3.79 (s, 3H), 3.32 (dd, J=13.1, 5.3, 1H), 3.04 (dd, J=13.1, 6.3, 1H), 2.50-2.35 (m, 7H), 1.99-1.91 (m, 2H), 1.48-1.40 (m, 2H).

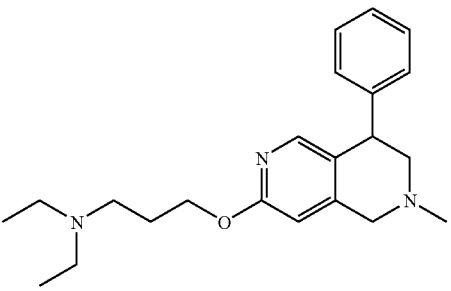

Example 7

Diethyl-[3-(6-methyl-8-phenyl-5,6,7,8-tetrahydro-[2,6]naphthyridin-3-yloxy)-propyl]-amine MS (ESI): mass calcd. for C₂₂H₃₁N₃O, 353.25; m/z found, 354.5 [M+H]⁺. ¹H NMR (CDCl₃): 7.66 (s, 1H), 7.33-7.17 (m, 5H), 6.46 (s, 1H), 4.27-4.17 (m, 3H), 3.70 (d, J=15.7, 1H), 3.53 (d, J=15.7, 1H), 3.04-2.94 (m, 1H), 2.06-2.05 (m, 7H), 2.41 (s, 3H), 1.93 (m, 2H), 1.02 (t, J=7.2, 6H).

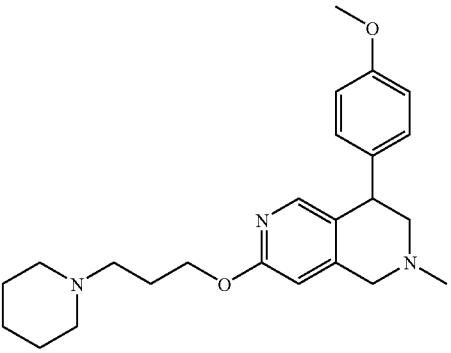

Example 8

4-(4-Methoxy-phenyl)-2-methyl-7-(3-piperidin-1-yl-propoxy)-1,2,3,4-tetrahydro-[2,6]-naphthyridine MS (ESI): mass calcd. for $C_{24}H_{33}N_3O_2$, 395.26; m/z found, 396.5 [M+H]$^+$. $^1$H NMR (CDCl$_3$): 7.66 (s, 1H), 7.10 (d, J=8.8, 2H), 6.83 (d, J=8.8, 2H), 6.44 (s, 1H), 4.25 (t, J=6.5, 2H), 4.16 (dd, J=8.9, 5.9, 1H), 3.79 (s, 3H), 3.68 (d, J=15.8, 1H), 3.51 (d, J=15.8, 1H), 2.98 (ddd, J=11.5, 5.6, 1.1, 1H), 2.53-2.35 (m, 10H), 1.98-1.90 (m, 2H), 1.61-1.38 (m, 4H), 1.46-1.38 (m, 2H).

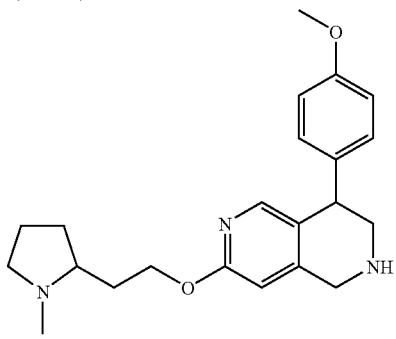

Example 9

4-(4-Methoxy-phenyl)-7-[2-(1-methyl-pyrrolidin-2-yl)-ethoxy]-1,2,3,4-tetrahydro-[2,6]-naphthyridine MS (ESI): mass calcd. for $C_{22}H_{29}N_3O_2$, 367.23; m/z found, 368.5 [M+H]$^+$. $^1$H NMR (CDCl$_3$): 7.72 (s, 1H), 7.01 (d, J=8.8, 2H), 6.84 (d, J=8.5, 2H), 6.45 (s, 1H), 4.34-4.22 (m, 2H), 4.11-3.97 (m, 3H), 3.79 (s, 3H), 3.32 (dd, J=13.0, 5.0, 1H), 3.10-3.02 (m, 2H), 2.34 (s, 3H), 2.23-2.10 (m, 3H), 2.05-1.95 (m, 1H), 1.85-1.49 (m, 5H).

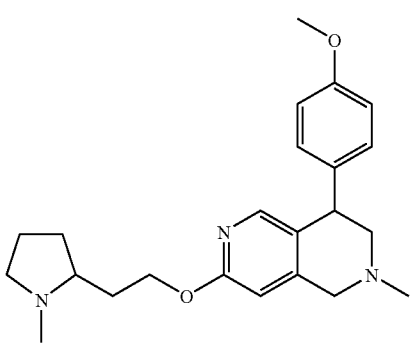

Example 10

4-(4-Methoxy-phenyl)-2-methyl-7-[2-(1-methyl-pyrrolidin-2-yl)-ethoxy]-1,2,3,4-tetrahydro-[2,6]-naphthyridine $^1$H NMR (CDCl$_3$): 7.60 (s, 1H), 7.03 (d, J=8.8, 1H), 6.76 (d, J=8.9, 2H), 6.37 (s, 1H), 4.26-4.05 (m, 3H), 3.72 (s, 3H), 3.62 (d, J=15.6, 1H), 3.44 (d, J=15.6, 1H), 3.03-2.96 (m, 1H), 2.91 (ddd, J=11.6, 5.5, 1.2, 1H), 2.43 (dd, J=11.6, 8.8, 1H), 2.34 (s, 3H), 2.27-2.25 (m, 3H), 1.96-1.87 (m, 1H), 1.76-1.41 (m, 4H).

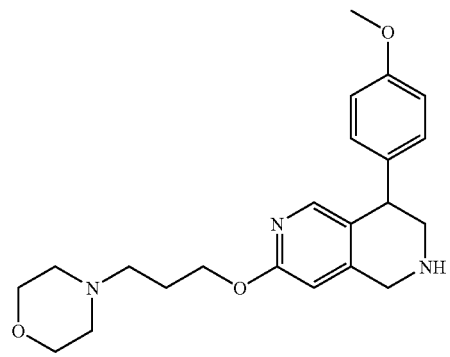

Example 11

4-(4-Methoxy-phenyl)-7-(3-morpholin-4-yl-propoxy)-1,2,3,4-tetrahydro-[2,6]-naphthyridine MS (ESI): mass calcd. for $C_{22}H_{29}N_3O_3$, 383.2; m/z found, 384.5 [M+H]$^+$. $^1$H NMR (CDCl$_3$): 7.74 (s, 1H), 7.07-7.01 (m, 2H), 6.90-6.85 (m, 2H), 6.48 (s, 1H), 4.32 (t, J=6.5, 2H), 4.14-3.97 (m, 3H), 3.82 (s, 3H), 3.75 (t, J=4.7, 4H), 3.39-3.31 (m, 1H), 3.12-3.04 (m, 1H), 2.59-2.21 (m, 7H), 2.21-2.05 (br s, 1H), 2.03-2.93 (m, 2H).

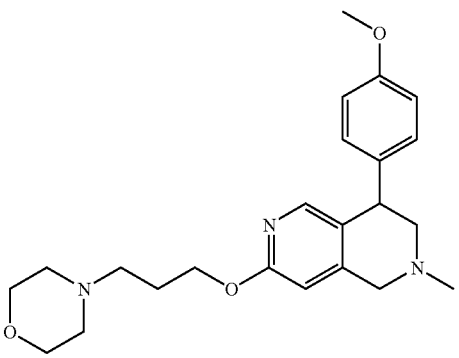

Example 12

4-(4-Methoxy-phenyl)-2-methyl-7-(3-morpholin-4-yl-propoxy)-1,2,3,4-tetrahydro-[2,6]-naphthyridine MS (ESI): mass calcd. for $C_{23}H_{31}N_3O_3$, 397.2; m/z found, 398.5 [M+H]$^+$. $^1$H NMR (CDCl$_3$): 7.59 (s, 1H), 7.05-7.01 (m, 2H), 6.89-6.74 (m, 2H), 6.80-6.74 (m, 2H), 6.37 (s, 1H), 4.21 (t, J=4.5, 2H), 4.12-4.05 (m, 1H), 3.72 (s, 3H), 3.69-3.58 (m, 6H), 3.48-3.40 (m, 1H), 2.95-2.88 (m, 1H), 2.49-2.36 (m, 8H), 2.34 (s, 3H), 1.95-1.82 (m, 3H).

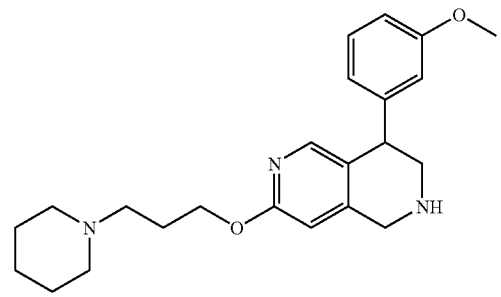

Example 13

4-(3-Methoxy-phenyl)-7-(3-piperidin-1-yl-propoxy)-1,2,3,4-tetrahydro-[2,6]-naphthyridine MS (ESI): mass calcd. for $C_{23}H_{31}N_3O_2$, 381.24; m/z found, 382.5 [M+H]$^+$. $^1$H NMR (CDCl$_3$): 7.65 (s, 1H), 7.15 (dd, J=7.9, 7.9, 1H), 6.71-6.68 (m, 1H), 6.55-6.54 (m, 1H), 6.37 (s, 1H), 4.19 (t, J=6.4, 2H), 4.02-3.90 (m, 3H), 3.70 (s, 3H), 3.27 (dd, J=13.2, 5.2, 1H), 3.02 (dd, J=13.3, 6.1, 1H), 2.49-2.31 (m, 6H), 1.95-1.87 (m, 2H), 1.58-1.52 (m, 4H), 1.42-1.33 (m, 2H).

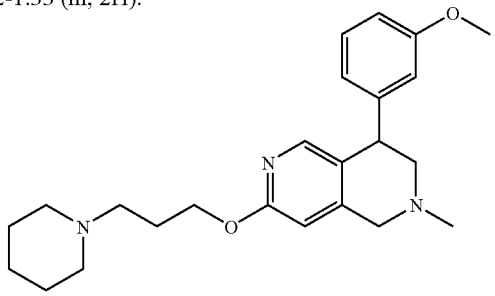

Example 14

4-(3-Methoxy-phenyl)-2-methyl-7-(3-piperidin-1-yl-propoxy)-1,2,3,4-tetrahydro-[2,6]-naphthyridine $^1$H NMR (CDCl$_3$): 7.61 (s, 1H), 7.14 (t, J=7.9, 1H), 6.74-6.65 (m, 3H), 6.37 (s, 1H), 4.18 (t, J=6.5, 2H), 4.10 (dd, J=8.6, 5.6, 1H), 3.70 (s, 3H), 3.61 (d, J=15.9, 1H), 3.45 (d, J=15.7, 1H), 2.92 (ddd, J=11.6, 5.5, 1.3, 1H), 2.48 (dd, J=11.5, 8.8, 1H), 2.43-2.29 (m, 9H), 1.92-1.85 (m, 2H), 1.56-1.50 (m, 4H), 1.41-1.33 (m, 2H).

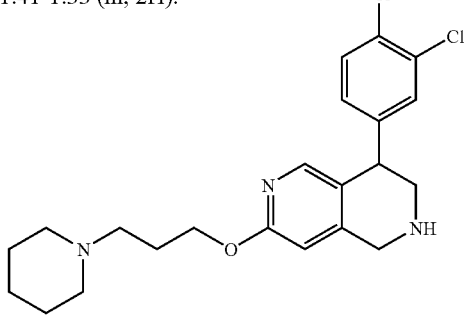

Example 15

4-(3,4-Dichloro-phenyl)-7-(3-piperidin-1-yl-propoxy)-1,2,3,4-tetrahydro-[2,6]-naphthyridine MS (ESI): mass calcd. for $C_{22}H_{27}Cl_2N_3O$, 419.2; m/z found, 420.4 [M+H]$^+$. $^1$H NMR (CDCl$_3$): 7.61 (s, 1H), 7.30 (d, J=8.2, 1H), 7.13-7.11 (m, 1H), 6.91-6.86 (m, 1H), 6.39 (s, 1H), 4.20 (t, J=6.5, 2H), 4.04-3.88 (m, 3H), 3.40 (s, 1H), 3.27 (dd, J=12.9, 5.1, 1H), 2.96 (dd, J=12.9, 6.1, 1H), 2.64-2.45 (m, 8H), 1.96-1.84 (m, 3H), 1.42-1.30 (m, 3H).

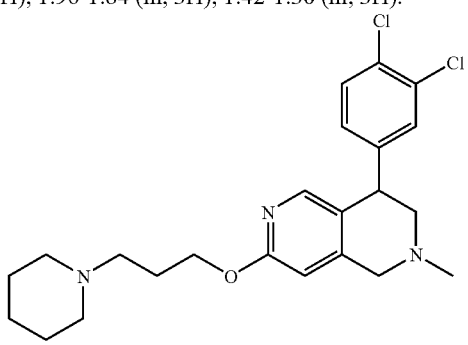

Example 16

4-(3,4-Dichloro-phenyl)-2-methyl-7-(3-piperidin-1-yl-propoxy)-1,2,3,4-tetrahydro-[2,6]-naphthyridine MS (ESI): mass calcd. for $C_{23}H_{29}Cl_2N_3O$, 433.2; m/z found, 434.5 [M+H]$^+$. $^1$H NMR (CDCl$_3$): 7.59 (s, 1H), 7.28 (d, J=8.4, 1H), 7.25-7.21 (m, 1H), 6.96 (dd, J=8.2, 2.2, 1H), 7.20 (s, 1H), 4.19 (t, J=6.5, 2H), 4.07 (t, J=6.3, 1H), 3.52 (s, 2H), 2.85 (dd, J=11.5, 5.3, 1H), 2.53-2.45 (m, 1H), 2.42-2.28 (m, 9H), 1.94-1.81 (m, 3H), 1.57-1.47 (m, 4H), 1.41-1.30 (m, 2H), 1.25-1.11 (m, 1H).

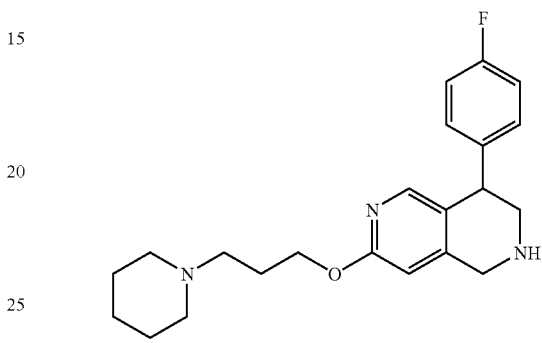

Example 17

4-(4-Fluoro-phenyl)-7-(3-piperidin-1-yl-propoxy)-1,2,3,4-tetrahydro-[2,6]naphthyridine MS (ESI): mass calcd. for $C_{22}H_{28}FN_3O$, 369.22; m/z found, 370.5 [M+H]$^+$. $^1$H NMR (CDCl$_3$): 7.68 (s, 1H), 7.08-6.93 (m, 4H), 6.46 (s, 1H), 4.26 (t, J=6.4, 2H), 4.10-3.98 (m, 4H), 3.35 (dd, J=13.1, 5.0, 1H), 3.03 (dd, J=13.1, 6.3, 1H), 2.50-2.33 (m, 6H), 2.00-1.90 (m, 2H), 1.63-1.55 (m, 4H), 1.48-1.40 (m, 2H).

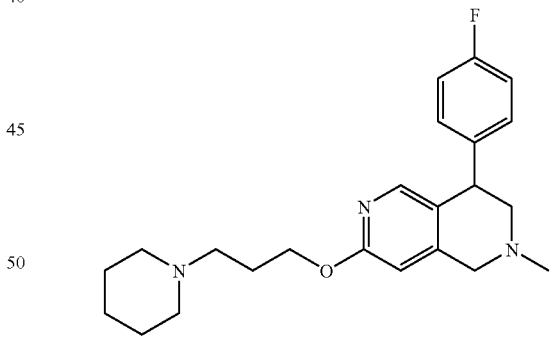

Example 18

4-(4-Fluoro-phenyl)-2-methyl-7-(3-piperidin-1-yl-propoxy)-1,2,3,4-tetrahydro-[2,6]-naphthyridine MS (ESI): mass calcd. for $C_{23}H_{30}FN_3O$, 383.24; m/z found, 384.5 [M+H]$^+$. $^1$H NMR (CDCl$_3$): 7.65 (s, 1H), 7.17-7.13 (m, 2H), 7.00-6.95 (m, 2H), 6.45 (s, 1H), 4.26 (t, J=6.6, 2H), 4.20-4.17 (m, 1H), 3.66 (d, J=15.8, 1H), 3.54 (d, J=15.8, 1H), 2.97 (ddd, J=11.5, 5.5, 1.2, 1H), 2.52 (dd, J=11.5, 8.2, 1H), 2.47-2.36 (m, 9H), 1.99-1.91 (m, 2H), 1.62-1.54 (m, 4H), 1.47-1.39 (m, 2H).

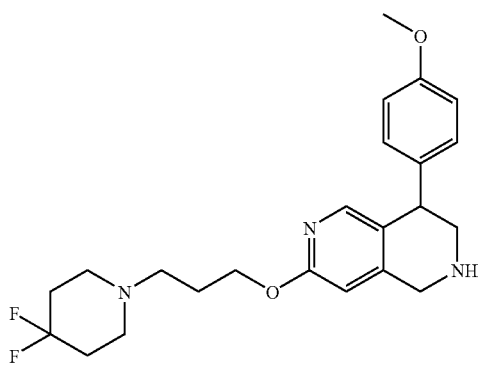

Example 19

7-[3-(4,4-Difluoro-piperidin-1-yl)-propoxy]-4-(4-methoxy-phenyl)-1,2,3,4-tetrahydro-[2,6]-naphthyridine MS (ESI): mass calcd. for $C_{23}H_{29}F_2N_3O_2$, 417.2; m/z found, 418.5 [M+H]$^+$. $^1$H NMR (CDCl$_3$): 7.71 (s, 1H), 7.05-6.96 (m, 2H), 6.88-6.78 (m, 2H), 6.44 (s, 1H), 4.32-4.24 (m, 2H), 4.13-3.95 (m, 3H), 3.79 (s, 3H), 3.37-3.28 (m, 1H), 3.09-3.00 (m, 1H), 2.62-2.48 (m, 6H), 2.07-1.88 (m, 6H).

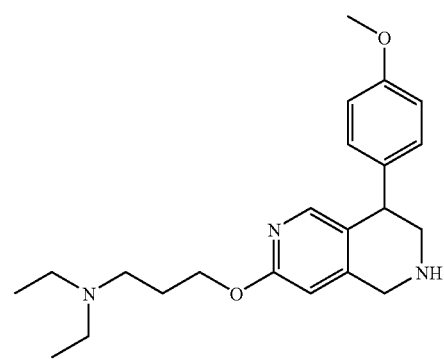

Example 20

Diethyl-{3-[8-(4-methoxy-phenyl)-5,6,7,8-tetrahydro-[2,6]naphthyridin-3-yloxy]-propyl}-amine MS (ESI): mass calcd. for $C_{22}H_{31}N_3O_2$, 369.2; m/z found, 370.5 [M+H]$^+$. $^1$H NMR (CDCl$_3$): 7.71 (s, 1H), 7.07-6.96 (m, 2H), 6.90-6.77 (m, 2H), 6.45 (s, 1H), 4.35-4.20 (m, 2H), 4.12-3.95 (m, 3H), 3.79 (s, 3H), 3.36-3.28 (m, 1H), 3.09-2.99 (m, 1H), 2.69-2.45 (m, 6H), 1.98-1.85 (m, 2H), 1.09-0.97 (m, 6H).

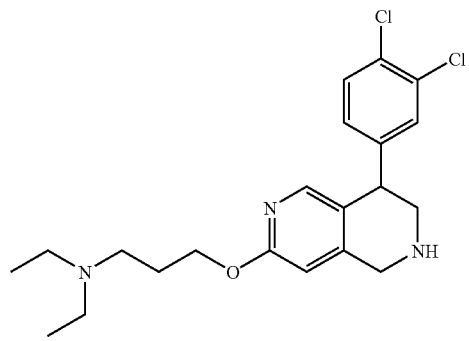

Example 21

{3-[8-(3,4-Dichloro-phenyl)-5,6,7,8-tetrahydro-[2,6]naphthyridin-3-yloxy]-propyl}-diethyl-amine MS (ESI): mass calcd. for $C_{21}H_{27}Cl_2N_3O$, 407.2; m/z found, 408.4 [M+H]$^+$. $^1$H NMR (CDCl$_3$): 7.69 (s, 1H), 7.40-7.34 (m, 1H), 7.21-7.19 (m, 1H), 6.99-6.93 (m, 1H), 6.47 (s, 1H), 4.27 (t, J=6.5, 2H), 1.12-3.97 (m, 3H), 3.35 (dd, J=12.9, 5.3, 1H), 3.04 (dd, J=12.9, 6.1, 1H), 2.65-2.48 (m, 6H), 1.96-1.85 (m, 2H), 1.07-0.98 (m, 6H).

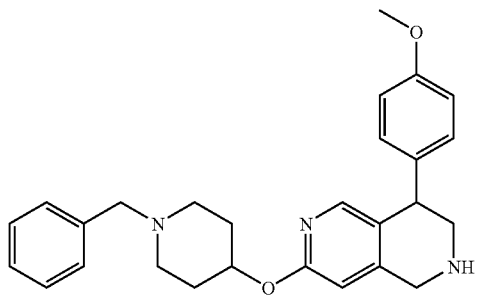

Example 22

7-(1-Benzyl-piperidin-4-yloxy)-4-(4-methoxy-phenyl)-1,2,3,4-tetrahydro-[2,6]-naphthyridine MS (ESI): mass calcd. for $C_{27}H_{31}N_3O_2$, 429.24; m/z found, 430.5 [M+H]$^+$. $^1$H NMR (CDCl$_3$): 7.69 (s, 1H), 7.34-7.28 (m, 5H), 7.01 (d, J=8.4, 2H), 6.84 (d, J=8.8, 2H), 6.44 (s, 1H), 5.02-4.94 (m, 1H), 4.08-3.96 (m, 3H), 3.79 9s, 3H), 3.52 (s, 2H), 3.31 (dd, J=12.9, 5.0, 1H), 3.03 (dd, J=12.9, 6.5, 1H), 2.78-2.70 (m, 2H), 2.33-2.25 (m, 2H), 2.06-1.96 (m, 2H), 1.85-1.75 (m, 2H).

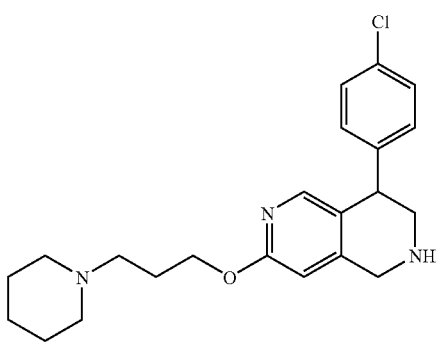

Example 23

4-(4-Chloro-phenyl)-7-(3-piperidin-1-yl-propoxy)-1,2,3,4-tetrahydro-[2,6]naphthyridine MS (ESI): mass calcd. for $C_{22}H_{28}ClN_3O$, 385.19; m/z found, 386.5 [M+H]$^+$. $^1$H NMR (CDCl$_3$): 7.68 (s, 1H), 7.27 (d, J=8.7, 2H), 7.03 (d, J=8.4, 2H), 6.46 (s, 1H), 4.26 (t, J=6.6, 2H), 4.10-3.98 (m, 3H), 3.34 (dd, J=13.3, 4.9, 1H), 3.03 (dd, J=12.9, 6.5, 1H), 2.48-2.35 (m, 6H), 2.00-1.91 (m, 2H), 1.62-1.55 (m, 4H), 1.47-1.40 (m, 2H).

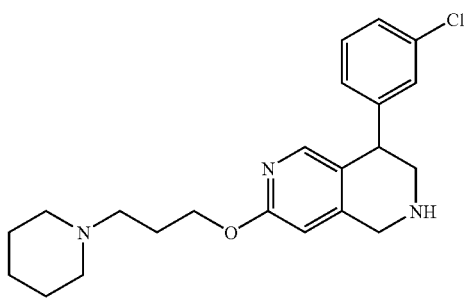

Example 24

4-(3-Chloro-phenyl)-7-(3-piperidin-1-yl-propoxy)-1,2,3,4-tetrahydro-[2,6]naphthyridine MS (ESI): mass calcd. for $C_{22}H_{28}ClN_3O$, 385.19; m/z found, 386.5 $[M+H]^+$.

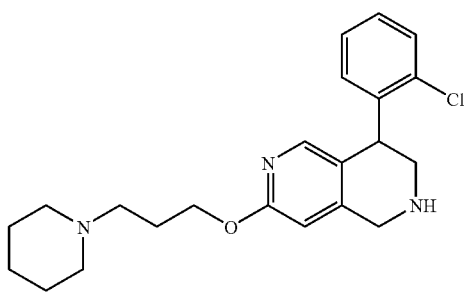

Example 25

4-(2-Chloro-phenyl)-7-(3-piperidin-1-yl-propoxy)-1,2,3,4-tetrahydro-[2,6]naphthyridine

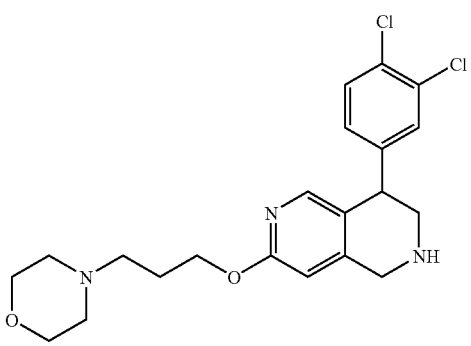

Example 26

4-(3,4-Dichloro-phenyl)-7-(3-morpholin-4-yl-propoxy)-1,2,3,4-tetrahydro-[2,6]-naphthyridine MS (ESI): mass calcd. for $C_{21}H_{25}Cl_2N_3O_2$, 421.1; m/z found, 422.4 $[M+H]^+$. $^1$H NMR (CDCl$_3$): 7.69 (s, 1H), 7.40-7.34 (m, 1H), 7.21-7.18 (m, 1H), 6.99-6.94 (m, 1H), 6.47 (s, 1H), 4.30 (t, J=6.5, 2H), 4.12-3.97 (m, 3H), 3.75-3.67 (m, 4H), 3.35 (dd, J=12.9, 5.3, 1H), 3.04 (dd, J=12.9, 6.1, 1H), 2.55-2.39 (m, 6H), 2.01-1.89 (m, 2H).

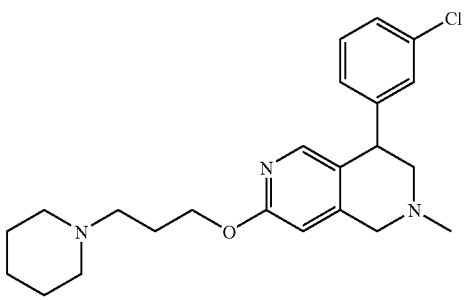

Example 27

4-(3-Chloro-phenyl)-2-methyl-7-(3-piperidin-1-yl-propoxy)-1,2,3,4-tetrahydro-[2,6]-naphthyridine MS (ESI): mass calcd. for $C_{23}H_{30}ClN_3O$, 399.21; m/z found, 400.5 $[M+H]^+$. $^1$H NMR (CDCl$_3$): 7.66 (s, 1H), 7.25-7.18 (m, 3H), 7.10-7.06 (m, 1H), 6.46 (s, 1H), 4.26 (t, J=6.5, 2H), 4.19-4.15 (m, 1H), 3.64 (d, J=15.7, 1H), 3.56 (d, J=15.7, 1H), 3.00-2.94 (m, 1H), 2.55 (dd, J=11.7, 8.0, 1H), 2.48-2.38 (m, 8H), 2.00-1.91 (m, 2H), 1.61-1.56 (m, 4H), 1.47-1.40 (m, 2H).

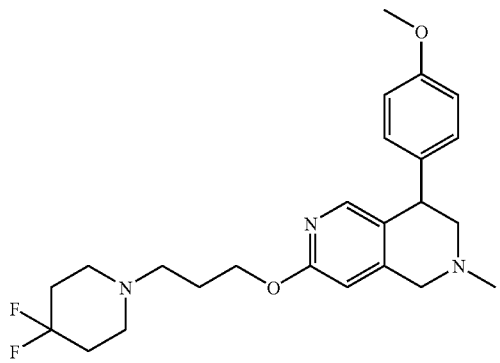

Example 28

7-[3-(4,4-Difluoro-piperidin-1-yl)-propoxy]-4-(4-methoxy-phenyl)-2-methyl-1,2,3,4-tetrahydro-[2,6]naphthyridine MS (ESI): mass calcd. for $C_{24}H_{31}F_2N_3O_2$, 431.2; m/z found, 432.5 $[M+H]^+$. $^1$H NMR (CDCl$_3$): 7.67 (s 1H), 7.14-7.06 (m, 2H), 6.86-6.81 (m, 2H), 6.44 (s, 1H), 4.27 (t, J=6.5, 2H), 4.16 (dd, J=8.4, 5.5, 1H), 3.79 (s, 3H), 3.72-3.65 (m, 1H), 3.48-3.44 (m, 1H), 3.01-2.95 (m, 1H), 2.61-2.47 (m, 7H), 2.41 (s, 3H), 2.06-1.88 (m, 6H).

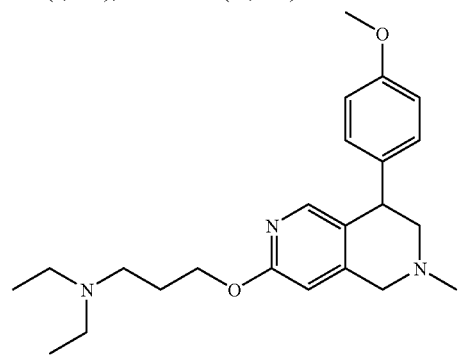

Example 29

Diethyl-{3-[8-(4-methoxy-phenyl)-6-methyl-5,6,7,8-tetrahydro-[2,6]naphthyridin-3-yloxy]-propyl}-amine MS (ESI): mass calcd. for $C_{23}H_{33}N_3O_2$, 383.3; m/z found, 384.5 [M+H]$^+$. $^1$H NMR (CDCl$_3$): 7.67 (s, 1H), 7.14-7.08 (m, 2H), 6.86-6.81 (m, 2H), 6.44 (s, 1H), 4.86-4.23 (m, 2H), 4.18-4.13 (m, 1H), 3.79 (s, 3H), 3.69 (d, J=15.8, 1H), 3.52 (d, J=15.6, 1H), 3.01-2.95 (m, 1H), 2.70-2.46 (m, 7H), 2.41 (s, 3H), 1.98-1.88 (m, 2H), 1.10-1.00 (m, 6H).

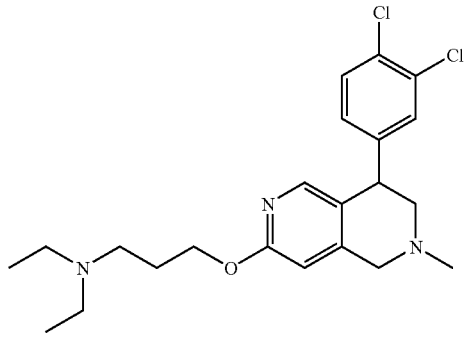

Example 30

{3-[8-(3,4-Dichloro-phenyl)-6-methyl-5,6,7,8-tetrahydro-[2,6]naphthyridin-3-yloxy]-propyl}-diethyl-amine MS (ESI): mass calcd. for $C_{22}H_{29}Cl_2N_3O$, 421.2; m/z found, 422.4 [M+H]$^+$. $^1$H NMR (CDCl$_3$): 7.71-7.61 (m, 1H), 7.50-7.40 (m, 1H), 7.34-7.27 (m, 1H), 7.13-7.01 (m, 1H), 6.63-6.54 (m, 1H), 4.71-4.24 (m, 6H), 3.82-3.64 (m, 2H), 3.33-3.07 (m, 8H), 2.49-2.12 (m, 2H), 1.41-1.21 (m, 6H).

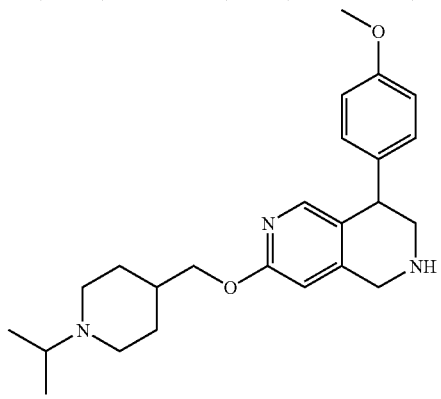

Example 31

7-(1-Isopropyl-piperidin-4-ylmethoxy)-4-(4-methoxy-phenyl)-1,2,3,4-tetrahydro-[2,6]-naphthyridine MS (ESI): mass calcd. for $C_{24}H_{33}N_3O_2$, 395.3; m/z found, 396.5 [M+H]$^+$. $^1$H NMR (CDCl$_3$): 7.71 (s, 1H), 7.05-6.96 (m, 2H), 6.88-6.81 (m, 2H), 6.45 (s, 1H), 4.13-3.95 (m, 5H), 3.79 (s, 3H), 3.32 (dd, J=12.9, 5.1, 1H), 3.04 (dd, J=12.9, 6.3, 1H), 2.95-2.88 (m, 2H), 2.76-2.66 (m, 1H), 2.20-2.09 (m, 2H), 1.92-1.70 (m, 4H), 1.46-1.32 (m, 2H), 1.09-1.01 (m, 6H).

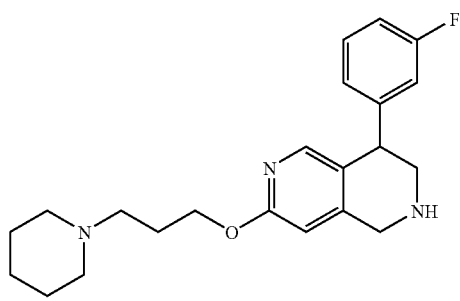

Example 32

4-(3-Fluoro-phenyl)-7-(3-piperidin-1-yl-propoxy)-1,2,3,4-tetrahydro-[2,6]naphthyridine MS (ESI): mass calcd. for $C_{22}H_{28}FN_3O$, 369.22; m/z found, 370.5 [M+H]$^+$. $^1$H NMR (CDCl$_3$): 7.70 (s, 1H), 7.29-7.23 (m, 1H), 6.95-6.88 (m, 2H), 6.80-6.76 (m, 1H), 6.46 (s, 1H), 4.27 (t, J=6.4, 2H), 4.10-3.98 (m, 3H), 3.35 (dd, J=13.0, 5.1, 1H), 3.07 (dd, J=13.0, 6.1, 1H), 2.50-2.31 (m, 5H), 1.99-1.89 (m, 2H), 1.62-1.55 (m, 4H), 1.46-1.40 (m, 2H).

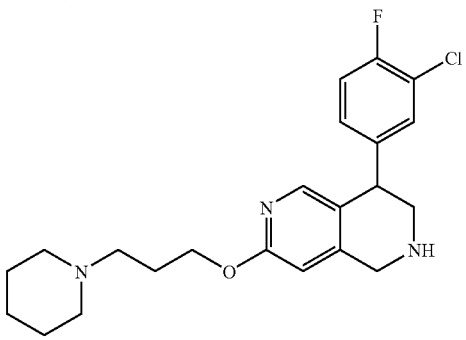

Example 33

4-(3-Chloro-4-fluoro-phenyl)-7-(3-piperidin-1-yl-propoxy)-1,2,3,4-tetrahydro-[2,6]naphthyridine MS (ESI): mass calcd. for $C_{22}H_{27}ClFN_3O$, 403.18; m/z found, 404.4 [M+H]$^+$. $^1$H NMR (CDCl$_3$): 7.68 (s, 1H), 7.13 (dd, J=7.1, 2.2, 1H), 7.07 (dd, J=8.6, 8.5, 1H), 7.00-6.95 (m, 1H), 6.47 (s, 1H), 4.27 (t, J=6.4, 2H), 4.10-3.97 (m, 3H), 3.34 (dd, J=12.9, 5.1, 1H), 3.03 (dd, J=12.9, 6.3, 1H), 2.49-2.36 (m, 6H), 2.00-1.92 (m, 2H), 1.62-1.55 (m, 4H), 1.47-1.40 (m, 2H).

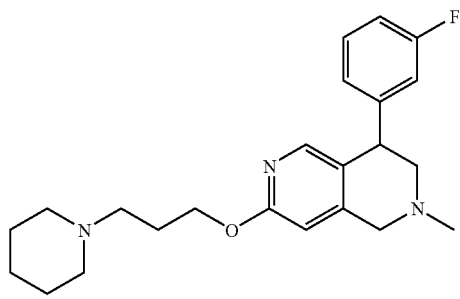

Example 34

4-(3-Fluoro-phenyl)-2-methyl-7-(3-piperidin-1-yl-propoxy)-1,2,3,4-tetrahydro-[2,6]-naphthyridine MS (ESI): mass calcd. for $C_{23}H_{30}FN_3O$, 383.24; m/z found, 384.5 [M+H]$^+$. $^1$H NMR (CDCl$_3$): 7.67 (s, 1H), 7.28-7.22 (m, 1H), 7.00-6.98 (m, 1H), 6.94-6.88 (m, 2H), 6.45 (s, 1H), 4.29 (t, J=6.6, 2H), 4.21-4.17 (m, 1H), 3.64 (d, J=15.7, 1H), 3.57 (d, J=16.0, 1H), 3.00-2.96 (m, 1H), 2.67-2.46 (m, 5H), 2.41 (s, 3H), 2.10-2.01 (m, 2H), 1.77-1.43 (m, 8H).

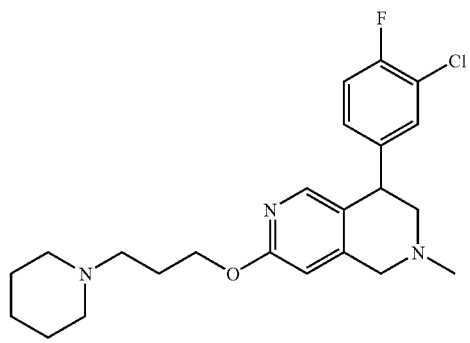

Example 35

4-(3-Chloro-4-fluoro-phenyl)-2-methyl-7-(3-piperidin-1-yl-propoxy)-1,2,3,4-tetrahydro-[2,6]naphthyridine MS (ESI): mass calcd. for $C_{23}H_{29}ClFN_3O$, 417.20; m/z found, 418.5 [M+H]$^+$. $^1$H NMR (CDCl$_3$): 7.65 (s, 1H), 7.25-7.22 (m, 1H), 7.07-7.04 (m, 2H), 6.46 (s, 1H), 4.27 (d, J=6.4, 2H), 4.16-4.13 (m, 1H), 3.65-3.55 (m, 2H), 2.93 (dd, J=11.5, 5.5, 1H), 2.60-2.40 (m, 6H), 2.40 (s, 3H), 2.04-1.96 (m, 2H), 1.72-1.52 (m, 8H).

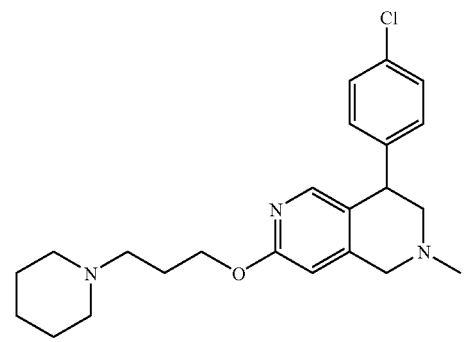

Example 36

4-(4-Chloro-phenyl)-2-methyl-7-(3-piperidin-1-yl-propoxy)-1,2,3,4-tetrahydro-[2,6]naphthyridine MS (ESI): mass calcd. for $C_{23}H_{30}ClN_3O$, 399.21; m/z found, 400.5 [M+H]$^+$. $^1$H NMR (CDCl$_3$): 7.64 (s, 1H), 7.26 (d, J=8.6, 2H), 7.13 (d, J=8.3, 2H), 6.45 (s, 1H), 4.25 (t, J=6.2, 2H), 4.18-4.15 (m, 1H), 3.65 (d, J=15.9, 1H), 3.56 (d, J=15.6, 1H), 2.97-2.93 (m, 1H), 2.53 (dd, J=11.5, 7.9, 1H), 2.50-2.38 (m, 9H), 1.99-1.92 (m, 2H), 1.63-1.56 (m, 4H), 1.47-1.40 (m, 2H).

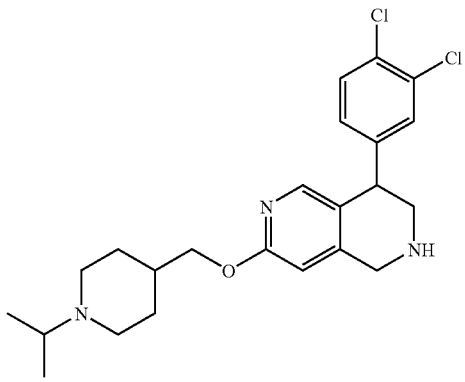

Example 37

4-(3,4-Dichloro-phenyl)-7-(1-isopropyl-piperidin-4-ylmethoxy)-1,2,3,4-tetrahydro-[2,6]naphthyridine MS (ESI): mass calcd. for $C_{24}H_{33}N_3O_2$, 395.3; m/z found, 396.5 [M+H]$^+$. $^1$H NMR (CDCl$_3$): 7.68 (s, 1H), 7.39-7.34 (m, 1H), 7.21-7.19 (m, 1H), 6.96 (dd, J=8.2, 2.2, 1H), 6.47 (s, 1H), 4.12-3.97 (m, 5H), 3.34 (dd, J=12.9, 5.1, 1H), 3.04 (dd, J=12.9, 6.1, 1H), 2.97-2.88 (m, 2H), 2.77-2.68 (m, 1H), 2.21-2.11 (m, 2H), 1.89-1.71 (m, 4H), 1.47-1.33 (m, 2H), 1.11-1.00 (m, 6H).

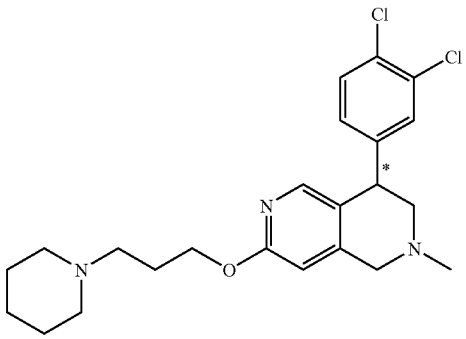

Example 38

4-(3,4-Dichloro-phenyl)-2-methyl-7-(3-piperidin-1-yl-propoxy)-1,2,3,4-tetrahydro-[2,6]-naphthyridine (enantiomer A).

Racemic 4-(3,4-dichloro-phenyl)-2-methyl-7-(3-piperidin-1-yl-propoxy)-1,2,3,4-tetrahydro-[2,6]-naphthyridine (Example 16) was separated into enantiomers by chiral HPLC (Conditions: AD-H 30% MeOH/Et$_3$N, 100 bar, 30° C., 3 mL/min). R$_T$=3.7 min.

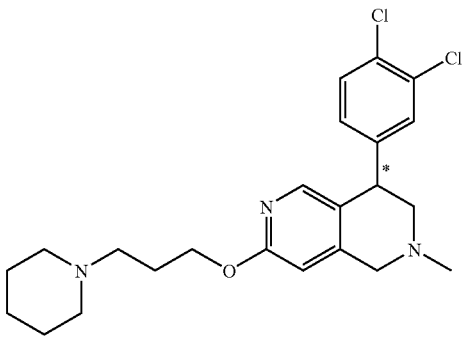

Example 39

4-(3,4-Dichloro-phenyl)-2-methyl-7-(3-piperidin-1-yl-propoxy)-1,2,3,4-tetrahydro-[2,6]-naphthyridine (enantiomer B)

This compound was obtained as described in Example 38. $R_T$=6.2 min.

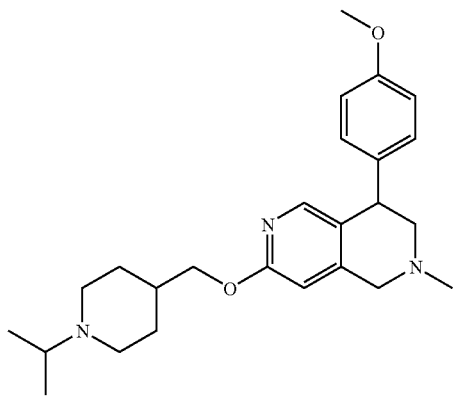

Example 40

7-(1-Isopropyl-piperidin-4-ylmethoxy)-4-(4-methoxy-phenyl)-2-methyl-1,2,3,4-tetrahydro-[2,6]-naphthyridine MS (ESI): mass calcd. for $C_{25}H_{35}N_3O_2$, 409.3; m/z found, 410.5 [M+H]$^+$. $^1$H NMR (CDCl$_3$): 7.72 (s, 1H), 7.15-7.08 (m, 2H), 6.93-6.87 (m, 2H), 6.53 (s, 1H), 4.93-4.41 (m, 2H), 4.40-4.04 (m, 4H), 3.81 (s, 3H), 3.79-3.65 (m, 1H), 3.61-3.45 (m, 3H), 2.99 (s, 3H), 2.84-2.66 (m, 2H), 2.14-1.89 (m, 5H), 1.49-1.20 (m, 6H).

Example 41

4-(3,4-Dichloro-phenyl)-7-(1-isopropyl-piperidin-4-ylmethoxy)-2-methyl-1,2,3,4-tetrahydro-[2,6]naphthyridine

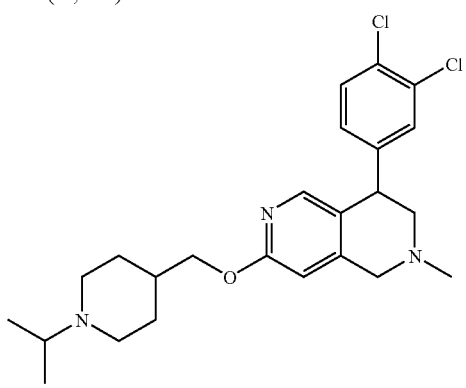

MS (ESI): mass calcd. for $C_{24}H_{31}Cl_2N_3O$, 447.2; m/z found, 448.4 [M+H]$^+$. $^1$H NMR (CDCl$_3$): 7.72 (s, 1H), 7.53-7.43 (m, 1H), 7.32-7.28 (m, 1H), 7.12-7.06 (m, 1H), 6.57 (s, 1H), 4.75-4.50 (m, 2H), 4.35-4.10 (m, 3H), 3.87-3.71 (m, 1H), 3.61-3.48 (m, 3H), 3.25-3.05 (m, 1H), 3.00 (s, 3H), 2.10-1.78 (m, 5H), 1.44-1.28 (m, 6H).

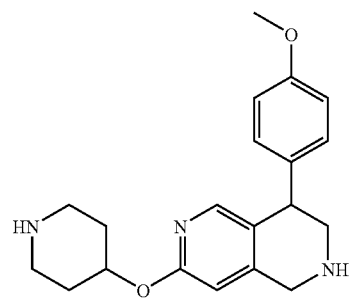

Example 42

4-(4-Methoxy-phenyl)-7-(piperidin-4-yloxy)-1,2,3,4-tetrahydro-[2,6]naphthyridine MS (ESI): mass calcd. for $C_{20}H_{25}N_3O_2$, 339.19; m/z found, 340.5 [M+H]$^+$. $^1$H NMR (CDCl$_3$): 7.69 (s, 1H), 7.01 (d, J=8.6, 2H), 6.84 (d, J=8.7, 2H), 6.44 (s, 1H), 5.13-5.01 (m, 1H), 4.11-3.96 (m, 3H), 3.79 (s, 3H), 3.36-3.28 (m, 1H), 3.15-3.00 (m, 3H), 2.81-2.69 (m, 2H), 2.08-1.94 (m, 3H), 1.70-1.57 (m, 3H).

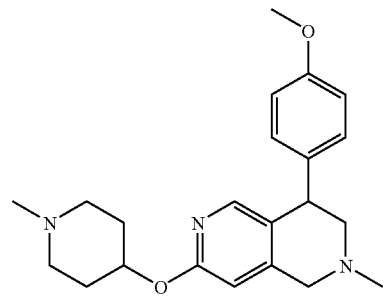

Example 43

4-(4-Methoxy-phenyl)-2-methyl-7-(1-methyl-piperidin-4-yloxy)-1,2,3,4-tetrahydro-[2,6]naphthyridine MS (ESI): mass calcd. for $C_{22}H_{29}N_3O_2$, 367.26; m/z found, 368.5 [M+H]$^+$. $^1$H NMR (CDCl$_3$): 7.65 (s, 1H), 7.11 (d, J=8.5, 2H), 6.83 (d, J=8.9, 2H), 6.44 (s, 1H), 5.01-4.94 (m, 1H), 4.15 (dd, J=8.6, 5.6, 1H), 3.79 (s, 3H), 3.68 (d, J=16.0, 1H), 3.50 (d, J=15.5, 1H), 2.98 (ddd, J=11.6, 5.5, 1.2, 1H), 2.76-2.66 (m, 2H), 2.51 (dd, J=11.6, 8.9, 1H), 2.41 (s, 3H), 2.33-2.25 (m, 5H), 2.06-1.99 (m, 2H), 1.86-1.76 (m, 2H).

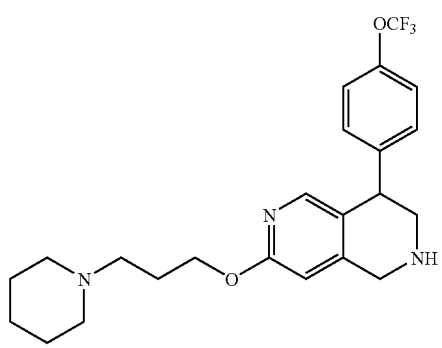

Example 44

7-(3-Piperidin-1-yl-propoxy)-4-(4-trifluoromethoxy-phenyl)-1,2,3,4-tetrahydro-[2,6]naphthyridine MS (ESI): mass calcd. for $C_{23}H_{28}F_3N_3O_2$, 435.2; m/z found, 436.5 [M+H]$^+$. $^1$H NMR (CDCl$_3$): 7.60 (s, 1H), 7.13-7.02 (m, 4H), 6.39 (s, 1H), 4.2 (t, J=6.5, 2H), 4.05-3.90 (m, 3H), 3.29 (dd, J=12.9, 5.1, 1H), 2.98 (dd, J=12.9, 6.3, 1H), 2.50-2.26 (m, 6H), 1.98-1.86 (m, 2H), 1.61-1.50 (m, 5H), 1.28-1.14 (m, 1H).

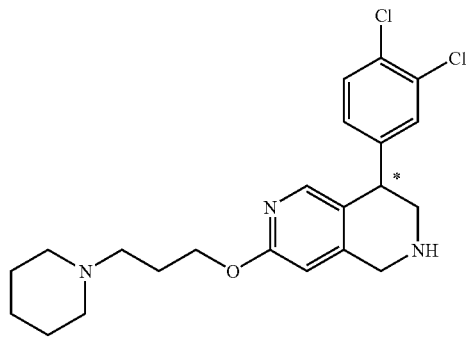

Example 45

4-(3,4-Dichloro-phenyl)-7-(3-piperidin-1-yl-propoxy)-1,2,3,4-tetrahydro-[2,6]-naphthyridine (enantiomer A)

Racemic 4-(3,4-dichloro-phenyl)-7-(3-piperidin-1-yl-propoxy)-1,2,3,4-tetrahydro-[2,6]-naphthyridine (Example 15) was separated into enantiomers by chiral HPLC (Conditions: OD 25% MeOH/Et$_3$N, 100 bar, 30° C., 2 mL/min). R$_T$=12.7 min.

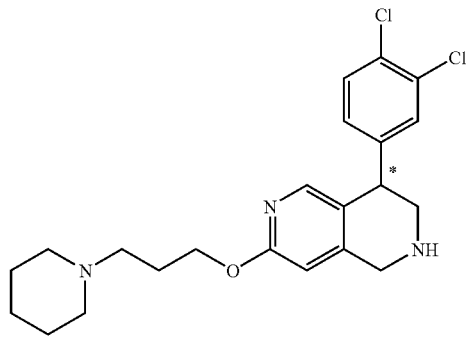

Example 46

4-(3,4-Dichloro-phenyl)-7-(3-piperidin-1-yl-propoxy)-1,2,3,4-tetrahydro-[2,6]-naphthyridine (enantiomer B)

This compound was obtained as described in Example 45. R$_T$=18.5 min.

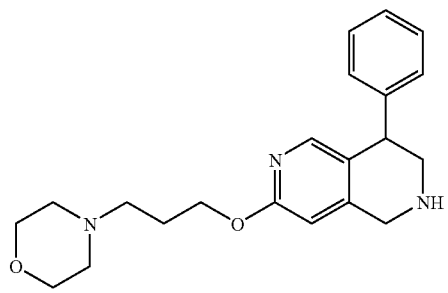

Example 47

7-(3-Morpholin-4-yl-propoxy)-4-phenyl-1,2,3,4-tetrahydro-[2,6]naphthyridine

MS (ESI): mass calcd. for $C_{21}H_{27}N_3O_2$, 353.21; m/z found, 354.4 [M+H]$^+$. $^1$H NMR (CDCl$_3$): 7.70 (s, 1H), 7.31-7.27 (m, 2H), 7.24-7.20 (m, 1H), 7.08 (d, J=7.1, 1H), 6.45 (s, 1H), 4.28 (t, J=6.7, 2H), 4.01-3.98 (m, 3H), 3.71-3.69 (m, 4H), 3.35 (dd, J=13.3, 5.2, 1H), 3.08 (dd, J=13.2, 6.3, 1H), 2.51-2.42 (m, 7H), 1.96-1.90 (m, 2H).

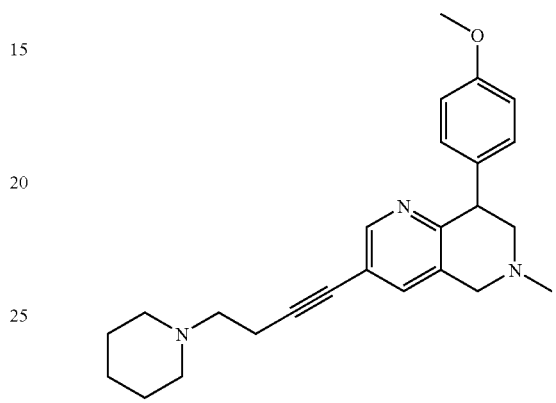

Example 48

8-(4-Methoxy-phenyl)-6-methyl-3-(4-piperidin-1-yl-but-1-ynyl)-5,6,7,8-tetrahydro-[1,6]naphthyridine trifluoroacetic acid salt

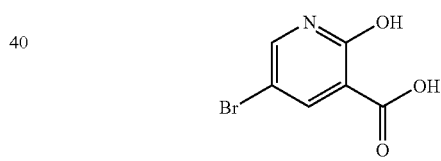

Step A. 5-Bromo-2-hydroxy-nicotinic acid. To a 0° C. solution of 50% aq. NaOH (45.4 g) and H$_2$O (251 mL) was added Br$_2$ (10 mL) dropwise over 5 min, additional 50% aq. NaOH (59.3 g), and 2-hydroxy-nicotinic acid (33.4 g). The resulting dark green solution was heated at 50° C. for 18 h, then was cooled to 0° C. and treated slowly with 12.1 N HCl until a solid precipitated. The solid was collected by vacuum filtration and dried under vacuum to give a white solid (40.8 g, 78%), which was taken on to the next step without purification. MS (ESI): mass calcd. for $C_6H_4BrNO_3$, 216.94; m/z found, 218.2 [M+H]$^+$. $^1$H NMR (DMSO-d$_6$): 14.33 (br s, 1H), 13.80 (br s, 1H), 8.37 (s, 1H), 8.30 (s, 1H).

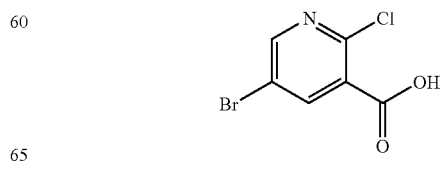

Step B. 5-Bromo-2-chloro-nicotinic acid. A mixture of 5-bromo-2-hydroxy-nictonic acid (32.9 g, 0.151 mol), SOCl$_2$ (167 mL), and DMF (10.5 mL) was heated at 70° C. for 4 h. The mixture was concentrated, cooled to 0° C., and quenched slowly with H$_2$O to give an off-white precipitate. The precipitate was stirred in H$_2$O for 1 h, and then was collected by filtration and dried under vacuum to give the title compound (35.5 g, 99%). The product was carried on to the next step without purification, but alternatively may be recrystallized from hot H$_2$O. MS (ESI): mass calcd. for C$_6$H$_3$BrClNO$_2$, 234.90; m/z found, 236.2 [M+H]$^+$. $^1$H NMR (acetone-d$_6$): 8.66 (d, J=2.5, 1H), 8.43 (d, J=2.5, 1H).

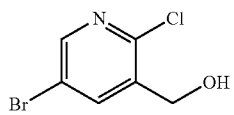

Step C. (5-Bromo-2-chloro-pyridin-3-yl)-methanol. A 0° C. mixture of 5-bromo-2-chloro-nicotinic acid (10.0 g, 42.3 mmol) and Et$_3$N (50.8 mmol) in THF (440 mL) was treated with isobutyl chloroformate (6.7 mL, 51 mmol). After 75 min, the mixture was filtered. The filtrate was concentrated to approximately 220 mL, diluted with H$_2$O, cooled to 0° C., and treated with NaBH$_4$ (3.38 g). After 2 h, the mixture was allowed to warm to rt and was stirred for 18 h. The mixture was diluted with EtOAc, washed with H$_2$O (3×), brine, dried (K$_2$CO$_3$), and concentrated to give an off-white solid. Chromatographic purification (SiO$_2$; EtOAc/hexanes) gave the title compound (6.61 g, 70%) as a white solid. MS (ESI): mass calcd. for C$_6$H$_5$BrClNO, 220.92; m/z found, 222.2 [M+H]$^+$. $^1$H NMR (acetone-d$_6$): 8.38 (d, J=2.5, 1H), 8.12 (m, 1H), 4.82 (brs, 1H), 4.69 (s, 2H).

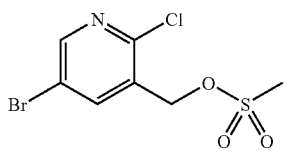

Step D. Methanesulfonic acid 5-bromo-2-chloro-pyridin-3-ylmethyl ester. A 0° C. mixture of (5-bromo-2-chloro-pyridin-3-yl)-methanol (1.00 g, 4.50 mmol) and DIPEA (2.40 mL, 13.5 mmol) in THF (22 mL) was treated with methanesulfonyl chloride (0.35 mL, 4.50 mmol). After 50 min, the mixture was diluted with DCM, washed with H$_2$O, satd. aq. NaHCO$_3$, and brine. The organic layer was dried (MgSO$_4$) and concentrated to give the title compound (1.47 g, >100%) as a yellow oil.

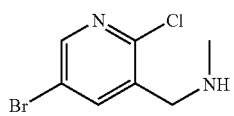

Step E. (5-Bromo-2-chloro-pyridin-3-ylmethyl)-methyl-amine. A solution of methanesulfonic acid 5-bromo-2-chloro-pyridiny-3-ylmethyl ester (6.84 g, 22.8 mmol) in EtOH (225 mL) was treated with MeNH$_2$ (40% in H$_2$O; 10 mL, 0.114 mol). After 2 h at rt, the mixture was concentrated and the residue was triturated with DCM. The mixture was filtered, and the filtrate was concentrated. The residue was chromatographed (SiO$_2$; EtOAc/hexanes) to give the title compound (3.23 g, 13.7 mmol) as a yellow oil. MS (ESI): mass calcd. for C$_7$H$_8$BrClN$_2$, 233.96; m/z found, 235.2 [M+H]$^+$. $^1$H NMR (CD$_3$OD): 8.34 (d, J=2.4, 1H), 8.04 (d, J=2.4, 1H), 4.8 (br s, 1H), 3.78 (s, 2H), 2.41 (s, 3H).

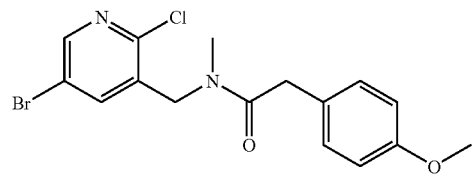

Step F. N-(5-Bromo-2-chloro-pyridin-3-ylmethyl)-2-(4-methoxy-phenyl)-N-methyl-acetamide. A 0° C. solution of (5-bromo-2-chloro-pyridin-3-ylmethyl)-methyl-amine (3.07 g, 13.0 mmol) and N-methylmorpholine (4.40 mL, 39.1 mmol) in DCM (130 mL) was treated with (4-methoxy-phenyl)-acetyl chloride (2.40 mL, 15.6 mmol) dropwise over 4 min. The resulting bright yellow solution was allowed to warm to rt and was stirred for 18 h. The mixture was diluted with DCM, washed with H$_2$O (2×), brine, dried (MgSO$_4$), and concentrated to a yellow oil. Chromatographic purification (SiO$_2$; EtOAc/hexanes) gave the title compound (4.71 g, 94%) as a pale-yellow oil. MS (ESI): mass calcd. for C$_{16}$H$_{16}$BrClN$_2$O$_2$, 382.01; m/z found, 383.3 [M+H]$^+$. $^1$H NMR (acetone-d$_6$, mixture of rotamers): 8.36 (d, J=2.3, 0.75H), 8.32 (d, J=2.1, 0.25H), 7.59-7.58 (m, 0.75H), 7.25-7.23 (m, 1.75H), 7.11 (d, J=8.5, 0.5H), 6.92-6.89 (m, 1.5H), 6.73 (d, J=8.6, 0.5H), 4.70 (s, 0.5H), 4.61 (s, 1.5H), 3.80-3.72 (m, 5H), 3.16 (s, 2.25H), 2.93 (s, 0.75H).

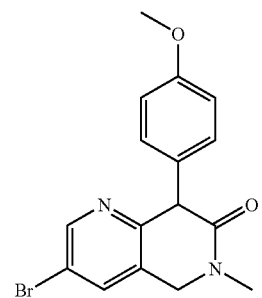

Step G. 3-Bromo-8-(4-methoxy-phenyl)-6-methyl-5,8-dihydro-6H-[1,6]naphthyridin-7-one. A slurry of NaH (95%; 530 mg, 17.3 mmol) in DMSO (3 mL) was treated with a solution of N-(5-bromo-2-chloro-pyridin-3-ylmethyl)-2-(4-methoxy-phenyl)-N-methyl-acetamide (2.21 g, 5.77 mmol) in DMSO (50 mL) over 5 min. After 2 h, the mixture was diluted with H$_2$O and extracted with EtOAc. The organic layer was washed with H$_2$O (3×), brine, dried (MgSO$_4$), and concentrated. The residue was purified (SiO$_2$; EtOH/hexanes) to give the title compound (1.30 g, 65%) as a reddish-tan foam. MS (ESI): mass calcd. for C$_{16}$H$_{15}$BrN$_2$O$_2$, 346.03; m/z found, 347.3 [M+H]$^+$. $^1$H NMR (acetone-d$_6$): 8.57 (d, J=1.9, 1H), 7.99-7.98 (m, 1H), 7.06-7.04 (m, 2H), 6.82-6.80 (m, 2H), 4.76 (d, J=16.8, 1H), 4.53 (d, J=16.8, 1H), 3.73 (s, 3H), 3.07 (s, 3H).

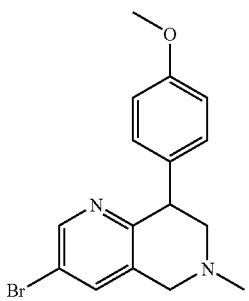

Step H. 3-Bromo-8-(4-methoxy-phenyl)-6-methyl-5,6,7,8-tetrahydro-[1,6]naphthyridine. A solution of 3-bromo-8-(4-methoxy-phenyl)-6-methyl-5,8-dihydro-6H-[1,6]naphthyridin-7-one (212 mg, 0.611 mmol) in THF (6.25 mL) was treated with BH$_3$.THF (1 M in THF; 2.0 mL). The mixture was heated at 60° C. for 2 h, then was allowed to cool to rt and was stirred for 18 h. The reaction was quenched by the slow addition of H$_2$O (5 mL) and conc. HCl (5 mL), and the resulting mixture was heated at 70° C. for 1 h. The mixture was cooled to rt, neutralized with 1 N NaOH to pH~10, and extracted with DCM. The organic layer was washed with H$_2$O, brine, dried (K$_2$CO$_3$), and concentrated. The residue was purified (SiO$_2$; EtOH/hexanes) to give the title compound (144 mg, 71%) as a colorless oil. Further purification by preparative reverse phase HPLC gave the product as the TFA salt. MS (ESI): mass calcd. for C$_{16}$H$_{17}$BrN$_2$O, 332.05; m/z found, 333.3 [M+H]$^+$. $^1$H NMR (CD$_3$OD): 8.52 (s, 1H), 7.97 (d, J=2.0, 1H), 7.07 (d, J=8.6, 2H), 6.92-6.90 (m, 2H), 4.93 (s, 2.5H), 4.69-4.56 (m, 3H), 3.94-3.90 (m, 1H), 3.79 (s, 3H), 3.65-3.61 (m, 1H), 3.08 (s, 3H).

Step I. A Smith process vial containing 3-bromo-8-(4-methoxy-phenyl)-6-methyl-5,6,7,8-tetrahydro-[1,6]naphthyridine (81.6 mg, 0.245 mmol), PPh$_3$ (22.6 mg, 0.086 mmol), Pd(PPh$_3$)$_2$Cl$_2$ (3.7 mg, 0.0053 mmol), CuI (18.7 mg, 0.098 mmol), 1-but-3-ynyl-piperidine (208.6 mg, 1.52 mmol), and Et$_2$NH (1.0 mL) in DMF (1 mL) was purged with N$_2$. The mixture was heated at 120° C. for 75 min, and then was allowed to cool to rt. The mixture was diluted with EtOAc, washed with H$_2$O (3×), brine, dried (K$_2$CO$_3$), and concentrated to give a reddish-brown oil. Chromatographic purification (SiO$_2$; 0-8% 2 N NH$_3$ in MeOH/DCM) gave a pale yellow oil, which was further purified by preparative reverse-phase HPLC to give 102.0 mg (67%) of the product as the TFA salt. MS (ESI): mass calcd. for C$_{25}$H$_{31}$N$_3$O, 389.25; m/z found, 390.5 [M+H]$^+$. $^1$H NMR (CD$_3$OD): 8.45 (s, 1H), 7.79 (s, 1H), 7.07 (d, J=8.6, 2H), 6.91-6.90 (m, 2H), 4.92 (s, 5H), 4.67-4.61 (m, 3H), 3.94-3.90 (m, 1H), 3.77 (s, 3H), 3.65-3.60 (m, 3H), 3.39 (t, J=7.3, 2H), 3.08 (s, 3H), 3.03-2.99 (m, 4H), 1.97-1.94 (m, 2H), 1.81-1.75 (m, 3H), 1.53-1.51 (m, 1H).

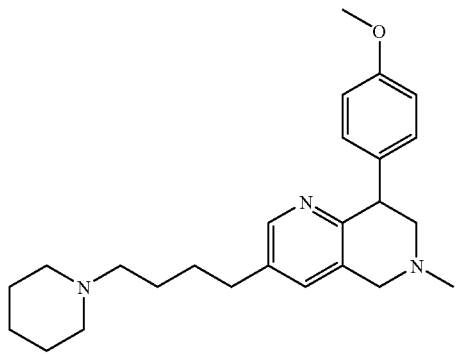

Example 49

8-(4-Methoxy-phenyl)-6-methyl-3-(4-piperidin-1-yl-butyl)-5,6,7,8-tetrahydro-[1,6]-naphthyridine trifluoroacetic acid salt A flask containing a mixture of 8-(4-methoxy-phenyl)-6-methyl-3-(4-piperidin-1-yl-but-1-ynyl)-5,6,7,8-tetrahydro-[1,6]naphthyridine (71.7 mg) and Pd/BaSO$_4$ (101.3 mg) in EtOH (5 mL) was evacuated and back-filled with N$_2$ (3×) and then with H$_2$ (3×). The mixture was treated with H$_2$ under balloon pressure for 4 h, then was filtered through a pad of diatomaceous earth. The filtrate was concentrated to give the title compound (47.3 mg, 96%). Treatment with TFA gave the TFA salt. MS (ESI): mass calcd. for C$_{25}$H$_{35}$N$_3$O, 393.28; m/z found, 394.5 [M+H]$^+$. $^1$H NMR (CD$_3$OD): 8.34 (s, 1H), 7.75 (s, 1H), 7.09 (d, J=8.6, 2H), 6.91 (d, 8.7, 2H), 4.90 (s, 6H), 4.70-4.64 (m, 3H), 3.94-3.90 (m, 1H), 3.77 (s, 3H), 3.64-3.58 (m, 1H), 3.53-3.50 (br m, 2H), 3.12-3.09 (m, 2H), 3.10 (s, 3H), 2.94-2.87 (m, 2H), 2.76 (t, J=7.7, 2H), 1.98-1.94 (br m, 2H), 1.84-1.69 (m, 7H), 1.54-1.48 (m, 1H).

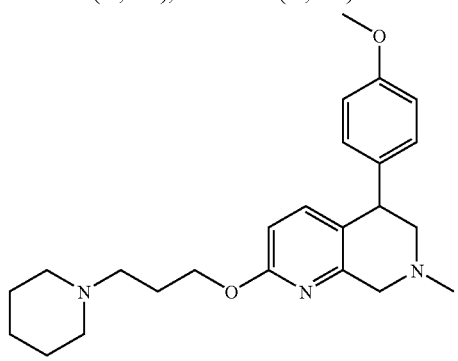

Example 50

5-(4-Methoxy-phenyl)-7-methyl-2-(3-piperidin-1-yl-propoxy)-5,6,7,8-tetrahydro-[1,7]naphthyridine

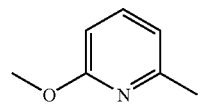

Step A. 2-Methoxy-6-methyl-pyridine. To a mixture of 6-methyl-pyridin-2-ol (10.0 g, 91.6 mmol) and Ag$_2$CO$_3$ (34.5 g, 125.1 mmol) in CHCl$_3$ (300 mL) was added MeI (64.4 mL, 1.04 mol) over 30 min. The mixture was stirred for 48 h at rt in the dark, then was filtered through a pad of SiO$_2$, washing with Et$_2$O. The filtrate was concentrated to provide the title compound (9.03 g, 80%). MS (ESI): mass calcd. for C$_7$H$_9$NO, 123.07; m/z found, 124.3 [M+H]$^+$. $^1$H NMR (CDCl$_3$): 7.46-7.41 (m, 1H), 6.70 (d, J=7.2, 1H), 6.53 (d, J=8.2, 1H), 3.91 (s, 3H), 2.44 (s, 3H).

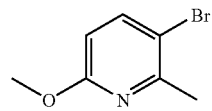

Step B. 3-Bromo-6-methoxy-2-methyl-pyridine. A mixture of 2-methoxy-6-methyl-pyridine (15.2 g, 123 mmol) and 1,3-dibromo-5,5-dimethyl hydantoin (35.3 g, 123 mmol) in THF (1 L) was stirred at rt for 48 h in the dark. The mixture was treated with 10% aq. Na$_2$S$_2$O$_3$ (100 mL) and stirred for 1 h. The mixture was extracted with Et$_2$O. The organic layer was washed with H$_2$O (2×), dried (MgSO$_4$), and concentrated. The residue was purified (SiO$_2$; 0-5% EtOAc/hexanes)

to give the title compound (18.7 g, 76%). MS (ESI): mass calcd. for C$_7$H$_8$BrNO, 200.98; m/z found, 202.2 [M+H]$^+$. $^1$H NMR (CDCl$_3$): 7.60 (d, J=8.6, 1H), 8.45 (d, J=8.7, 1H), 3.90 (s, 3H), 2.54 (s, 3H).

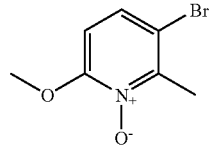

Step C. 3-Bromo-6-methoxy-2-methyl-pyridine N-oxide. A 5° C. solution of 3-bromo-6-methoxy-2-methyl-pyridine (20.8 g, 103 mmol) in CHCl$_3$ (550 mL) was treated with mCPBA (60%; 44.4 g, 154 mmol) slowly in portions over 1 h. The mixture was allowed to warm to rt, and then was heated at 50° C. for 18 h. The mixture was cooled to rt, treated with 5% aq. Na$_2$CO$_3$ (300 mL), and stirred for 1 h. The mixture was diluted with DCM and washed with H$_2$O (3×). The organic layer was separated, dried (MgSO$_4$), and concentrated to a light yellow oil (26.9 g). The oil was purified (SiO$_2$; 0-5% 2 M NH$_3$ in MeOH/DCM) to give the title compound (15.7 g, 70%). MS (ESI): mass calcd. for C$_7$H$_8$BrNO$_2$, 216.97; m/z found, 218.2 [M+H]$^+$. $^1$H NMR (CDCl$_3$): 7.44 (d, J=8.9, 1H), 6.68 (d, J=9.0, 1H), 4.05 (s, 3H), 2.74 (s, 3H).

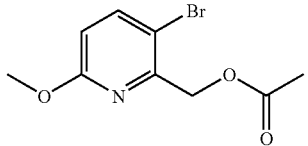

Step D. Acetic acid 3-bromo-6-methoxy-pyridin-2-ylmethyl ester. A solution of 3-bromo-6-methoxy-2-methyl-pyridine N-oxide (6.73 g, 30.9 mmol) in Ac$_2$O (42 mL) was heated at 120° C. for 3.5 h, then was cooled to rt. The mixture was diluted with MeOH (250 mL) and concentrated (3×) to yield a brown oil (7.29 g), which was purified (SiO$_2$; 0-12% 2 M NH$_3$ in MeOH/DCM) to give the title compound (6.42 g, 80%). $^1$H NMR (CDCl$_3$): 7.65 (d, J=8.7, 1H), 6.58 (d, J=8.7, 1H), 5.22 (s, 2H), 3.89 (s, 3H), 2.17 (s, 3H).

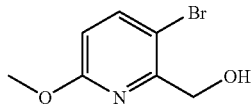

Step E. (3-Bromo-6-methoxy-pyridin-2-yl)-methanol. A mixture of acetic acid 3-bromo-6-methoxy-pyridine-2-ylmethyl ester (3.94 g, 15.2 mmol) and 1 M aq. K$_2$CO$_3$ (26.2 mL, 26.2 mmol) in MeOH (30 mL) was stirred at rt for 18 h. The mixture was concentrated, diluted with H$_2$O (15 mL), and extracted with DCM (3×). The combined extracts were washed with H$_2$O, dried, and concentrated to give the title compound (2.97 g, 90%). MS (ESI): mass calcd. for C$_7$H$_8$BrNO$_2$, 216.97; m/z found, 218.2 [M+H]$^+$. $^1$H NMR (CDCl$_3$): 7.68 (d, J=8.6, 1H), 6.60 (d, J=8.6, 1H), 4.67 (dd, J=4.7, 0.6, 2H), 4.01 (t, 4.7, 1H), 3.97 (s, 3H).

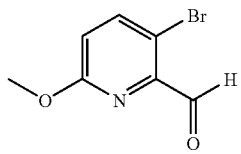

Step F. 3-Bromo-6-methoxy-pyridine-2-carbaldehyde. A mixture of (3-bromo-6-methoxy-pyridin-2-yl)-methanol (3.25 g, 14.9 mmol) and MnO$_2$ (9.07 g, 104 mmol) in CHCl$_3$ (50 mL) was heated at reflux for 18 h. The mixture was filtered while hot and the filtrate was concentrated. The residue was purified (SiO$_2$; 10% EtOAc/hexanes) to yield the title compound (2.55 g, 80%). MS (ESI): mass calcd. for C$_7$H$_6$BrNO$_2$, 214.96; m/z found, 218.2 [M+H]$^+$. $^1$H NMR (CDCl$_3$): 10.13 (s, 1H), 7.80 (d, J=8.7, 1H), 6.83 (d, J=8.7, 1H), 3.99 (s, 3H).

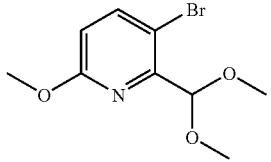

Step G. 3-Bromo-2-dimethoxymethyl-6-methoxy-pyridine. A solution of 3-bromo-6-methoxy-pyridine-2-carbaldehyde (4.63 g, 21.4 mmol) and trimethylorthoformate (120 mL) in MeOH (200 mL) was treated with conc. H$_2$SO$_4$ (4 mL). The mixture was stirred for 18 h, then was treated with 5% aq. NaHCO$_3$ (150 mL), with stirring, and was extracted with DCM (5×). The combined organic extracts were washed with brine (100 mL), H$_2$O (100 mL), dried (MgSO$_4$), and concentrated to yield the title compound (5.07 g, 90%). $^1$H NMR (CDCl$_3$): 7.67 (d, J=8.6, 1H), 6.61 (d, J=8.6, 1H), 5.56 (s, 1H), 3.95 (s, 3H), 3.52 (s, 6H).

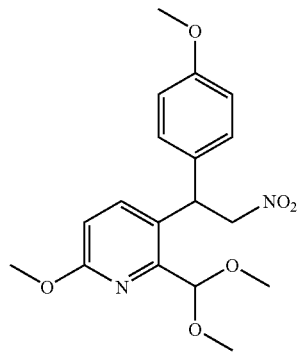

Step H. 2-Dimethoxymethyl-6-methoxy-3-[1-(4-methoxy-phenyl)-2-nitro-ethyl]-pyridine. A −78° C. solution of 3-bromo-2-dimethoxymethyl-6-methoxy-pyridine (4.05 g, 15.4 mmol) in toluene (120 mL) was treated with n-BuLi (1.6 M in hexanes; 10.6 mL, 17.0 mmol) over 15 min. After 40 min, a −78° C. solution of 1-methoxy-4-(2-nitro-vinyl)-benzene (2.99 g, 16.7 mmol) in toluene (72 mL) was added over 8 min. After 1 h, a solution of acetic acid (4 mL) in toluene (20 mL) was added dropwise at −78° C. After 30 min, the mixture was allowed to warm to rt, was diluted with brine, and extracted with DCM (3×). The combined organic extracts were dried and concentrated to yield crude red oily product (7.30 g). Purification (SiO$_2$; 0-15% EtOAc/hexanes) gave the title compound (2.70 g, 48%). MS (ESI): mass calcd. for C$_{18}$H$_{22}$N$_2$O$_6$, 362.15; m/z found, 363.4 [M+H]$^+$. $^1$H NMR (CDCl$_3$): 7.39 (d, J=8.7, 1H), 7.21 (d, J=8.7, 2H), 6.85 (d, J=8.7, 2H), 6.63 (d, J=8.6, 1H), 5.76 (dd, J=6.7, 2.7, 1H), 5.28 (s, 1H), 4.93-4.85 (m, 2H), 3.92 (s, 3H), 3.77 (s, 3H), 3.53 (s, 3H), 3.49 (s, 3H).

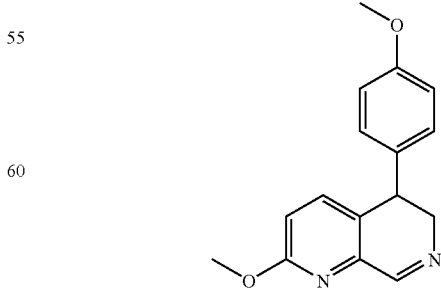

Step I. 2-Methoxy-5-(4-methoxy-phenyl)-5,6-dihydro-[1,7]naphthyridine. A solution of 2-dimethoxy-methyl-6-methoxy-3-[1-(4-methoxy-phenyl)-2-nitro-ethyl]-pyridine (3.78 g, 10.4 mmol) in acetic acid (10 mL) was treated with Zn powder (6.83 g, 104 mmol) and the mixture was heated at 40° C. for 18 h. The mixture was filtered, washing with MeOH. The filtrate was concentrated to give a white solid, which was dissolved in 6 N HCl (180 mL) and stirred for 18 h. The mixture was cooled to 20° C., neutralized with satd. aq. NaHCO₃ to pH~8, and extracted with DCM (3×). The combined organic extracts were washed with H₂O, dried (MgSO₄), and concentrated. Purification (SiO₂; 5% 2 M NH₃ in MeOH/DCM) gave the title compound (3.18 g, 95%). MS (ESI): mass calcd. for $C_{16}H_{16}N_2O_2$, 268.12; m/z found, 269.4 [M+H]⁺. ¹H NMR (CDCl₃): 7.26 (s, 1H), 7.10 (d, J=8.4, 1H), 7.00 (d, J=8.7, 2H), 6.84 (d, J=8.7, 2H), 6.50 (d, J=8.4, 1H), 4.10 (m, 1H), 3.91 (s, 3H), 3.79 (s, 3H), 3.33-3.36 (m, 1H), 3.04-2.99 (m, 1H).

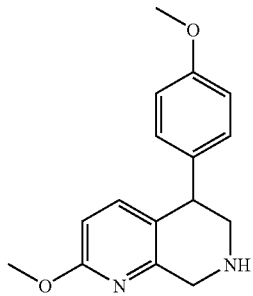

Step J. 2-Methoxy-5-(4-methoxy-phenyl)-5,6,7,8-tetrahydro-[1,7]naphthyridine. A solution of 2-methoxy-5-(4-methoxy-phenyl)-5,6-dihydro-[1,7]naphthyridine (3.18 g, 10.4 mmol) in EtOH (80 mL) was treated with NaBH₄ (2.00 g, 52.9 mmol) in portions over 2 h. The mixture was stirred 18 h, then was diluted with satd. aq. NaHCO₃ (50 mL) and extracted with DCM (3×). The combined organic extracts were washed with H₂O, dried (MgSO₄), and concentrated. The residue was purified (SiO₂; 2-4% 2 M NH₃ in MeOH/DCM) to give the title compound (2.54 g, 90%). MS (ESI): mass calcd. for $C_{16}H_{18}N_2O_2$, 270.14; m/z found, 271.4 [M+H]⁺. ¹H NMR (CDCl₃): 7.26 (s, 1H), 7.10 (d, J=8.4, 1H), 7.00 (d, J=8.7, 2H), 6.84 (d, J=8.7, 2H), 6.50 (d, J=8.4, 1H), 4.12-3.96 (m, 3H), 3.91 (s, 3H), 3.79 (s, 3H), 3.39-3.31 (m, 1H), 3.04-2.99 (m, 1H).

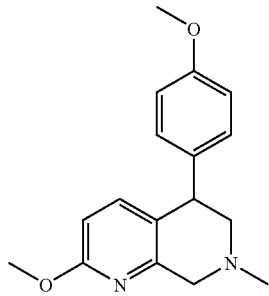

Step K. 2-Methoxy-5-(4-methoxy-phenyl)-7-methyl-5,6,7,8-tetrahydro-[1,7]naphthyridine. A mixture of 2-methoxy-5-(4-methoxy-phenyl)-5,6,7,8-tetrahydro-[1,7]naphthyridine (2.54 g, 9.40 mmol) and paraformaldehyde (4.22 g, 141 mmol) in MeOH (50 mL) was heated at 55° C. for 2.5 h, then was cooled to rt and treated with NaBH₄ (5.20 g, 136 mmol) in portions. After 18 h at rt, the mixture was diluted with satd. aq. NaHCO₃ (until pH~8) and extracted with DCM. The combined organic layers were washed with H₂O, dried, and concentrated to give the title compound (1.75 g, 65%). MS (ESI): mass calcd. for $C_{17}H_{20}N_2O_2$, 284.15; m/z found, 285.4 [M+H]⁺. ¹H NMR (CDCl₃): 7.10-7.05 (m, 3H), 6.85-6.80 (m, 2H), 6.47 (d, J=8.5, 1H), 4.16-4.10 (m, 1H), 3.90 (s, 3H), 3.78 (s, 3H), 3.75-3.77 (m, 1H), 3.59-3.52 (m, 1H), 3.03-2.97 (m, 1H), 2.53-2.47 (m, 1H), 2.44 (s, 3H).

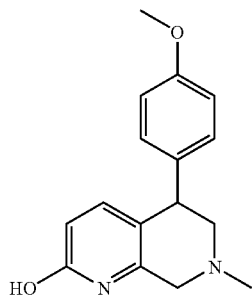

Step L. 5-(4-Methoxy-phenyl)-7-methyl-5,6,7,8-tetrahydro-[1,7]naphthyridin-2-ol. A solution of 2-methoxy-5-(4-methoxy-phenyl)-7-methyl-5,6,7,8-tetrahydro-[1,7]naphthyridine (1.75 g, 6.15 mmol) in 4 M HCl (100 mL) was heated at reflux for 5 h. The solution was concentrated to give 5-(4-methoxy-phenyl)-7-methyl-5,6,7,8-tetrahydro-[1,7]naphthyridin-2-ol hydrochloride. The salt was neutralized with satd. aq. NaHCO₃, and extracted with DCM. The organic layer was concentrated to give the title compound (1.14 g, 68%) as the free base. MS (ESI): mass calcd. for $C_{16}H_{18}N_2O_2$, 270.33; m/z found, 271.4 [M+H]⁺. ¹H NMR (CDCl₃): 7.12-7.07 (m, 2H), 7.03 (d, J=9.3, 1H), 6.87-6.82 (m, 2H), 6.37 (d, J=9.3, 1H), 4.00-4.92 (m, 1H), 3.80 (s, 3H), 3.69-3.62 (m, 1H), 3.56-3.50 (m, 1H), 3.01-2.95 (m, 1H), 2.52-2.45 (m, 1H), 2.44 (s, 3H).

Step M. To a mixture of 5-(4-methoxy-phenyl)-7-methyl-5,6,7,8-tetrahydro-[1,7]naphthyridin-2-ol (0.10 g, 0.37 mmol) and PPh₃ (0.097 g, 0.37 mmol) in THF (5 mL) was added a solution of di-tert-butyldiazodicarboxylate (0.085 g, 0.37 mmol) in THF (5 mL). After 30 min, a solution of 3-piperidin-1-yl-propan-1-ol (0.053 g, 0.37 mmol) in THF (5 mL) was added slowly. After 18 h, the mixture was concentrated, and the resulting solid was purified (SiO₂; 0-8% 2 M NH₃ in MeOH/DCM) to give the title compound (30 mg, 20%). MS (ESI): mass calcd. for $C_{24}H_{33}N_3O_2$, 395.26; m/z found, 396.6 [M+H]⁺. ¹H NMR (CDCl₃): 7.10-7.04 (m, 3H), 6.83 (d, J=8.6, 2H), 6.45 (d, J=8.4, 1H), 4.33-4.25 (m, 2H), 4.15-4.10 (m, 1H), 3.79 (s, 3H), 3.76-3.70 (m, 1H), 3.57-3.50 (m, 1H), 3.02-2.97 (m, 1H), 2.53-2.45 (m, 3H), 2.44 (s, 3H), 2.42-2.38 (m, 3H), 2.00-1.92 (m, 2H), 1.66-1.54 (m, 7H).

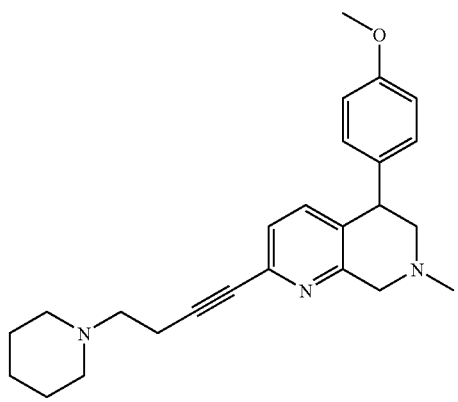

Example 51

5-(4-Methoxy-phenyl)-7-methyl-2-(4-piperidin-1-yl-but-1-ynyl)-5,6,7,8-tetrahydro-[1,7]naphthyridine

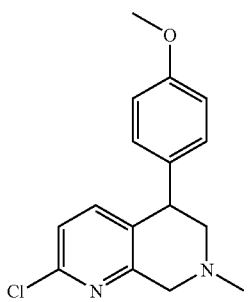

Step A. 2-Chloro-5-(4-methoxy-phenyl)-7-methyl-5,6,7,8-tetrahydro-[1,7]naphthyridine. A solution of 5-(4-methoxy-phenyl)-7-methyl-5,6,7,8-tetrahydro-[1,7]naphthyridin-2-ol hydrochloride (153 mg, 0.499 mmol) in POCl$_3$ (1 mL) was heated at 100° C. for 6 h. The mixture was cooled to rt, and was poured into a stirring mixture of ice and satd. aq. NaHCO$_3$, and was extracted with DCM (4×). The combined organic layers were washed with H$_2$O and brine, dried (MgSO$_4$), and concentrated to give the title compound (180 mg), which was carried directly on to the next step. MS (ESI): mass calcd. for $C_{16}H_{17}ClN_2O$, 288.10; m/z found, 289.8 [M+H]$^+$.

Step B. A flask containing a mixture of 2-chloro-5-(4-methoxy-phenyl)-7-methyl-5,6,7,8-tetrahydro-[1,7]naphthyridine (0.080 g, 0.28 mmol), Et$_2$NH (1.0 mL), 1-but-3-ynyl-piperidine (0.077 g, 0.56 mmol), CuI (5.3 mg, 27.8 umol), PPh$_3$ (36 mg, 0.14 mmol), and Pd(PPh$_3$)$_2$Cl$_2$ (0.020 g, 0.028 mmol) in DMF (0.5 mL) was evacuated and back-filled with N$_2$ (3×). The mixture was heated at 105 C for 18 h, then was cooled to rt, diluted with satd. aq. NaHCO$_3$, and extracted with DCM. The combined organic layers were washed with H$_2$O, dried, and concentrated. The residue was purified (SiO$_2$; 0-6% 2 M NH$_3$ in MeOH/DCM) to give the title compound (35 mg, 33%). MS (ESI): mass calcd. for $C_{25}H_{31}N_3O$, 389.25; m/z found, 390.6 [M+H]$^+$. $^1$H NMR (CDCl$_3$): 7.15-7.08 (m, 2H), 7.06 (d, J=8.7, 2H), 6.83 (d, J=8.7, 2H), 4.23-4.17 (m, 1H), 3.91-3.85 (m, 1H), 3.79 (s, 3H), 3.66-3.59 (m, 1H), 3.05-2.99 (m, 1H), 2.76-2.62 (m, 4H), 2.56-2.46 (m, 5H), 2.45 (s, 3H), 1.68-1.58 (m, 4H), 1.49-1.40 (m, 2H).

Biological Methods

H$_3$ Receptor Binding

Binding of compounds to the cloned human H$_3$ receptor, stably expressed in SK-N-MC cells, was performed (Lovenberg, T. W. et al. *J. Pharmacol. Exp. Ther.* 2000, 293, 771-778). Briefly, cell pellets from SK-N-MC cells expressing the human H$_3$ receptor were homogenized in 50 mM Tris-HCl/5 mM EDTA and re-centrifuged at 30,000 g for 30 min. Pellets were re-homogenized in 50 mM Tris/5 mM EDTA (pH 7.4). Membranes were incubated with 0.8 nM N-[$^3$H]-α-methylhistamine plus/minus test compounds for 60 min at 25° C. and harvested by rapid filtration over GF/C glass fiber filters (pretreated with 0.3% polyethylenimine) followed by four washes with ice-cold buffer. Nonspecific binding was defined in the presence of 10 μM histamine. IC$_{50}$ values were determined by a single site curve-fitting program (GraphPad, San Diego, Calif.) and converted to K$_i$ values based on a N-[$^3$H]-α-methylhistamine K$_d$ of 800 pM and a ligand concentration of 800 pM (Cheng & Prusoff, *Biochem. Pharmacol.* 1973, 22, 3099-3108). Data are presented in Table 1.

Rat Brain SERT

A rat brain without cerebellum (Zivic Laboratories, Inc.-Pittsburgh, Pa.) was homogenized in a 52.6 mM Tris pH 8/126.4 mM NaCl/5.26 mM KCl mixture and centrifuged at 1,000 rpm for 5 min. The supernatant was removed and re-centrifuged at 15,000 rpm for 30 min. Pellets were re-homogenized in a 52.6 mM Tris pH8/126.4 mM NaCl/5.26 mM KCl mixture. Membranes were incubated with 0.6 nM [$^3$H]-Citalopram plus/minus test compounds for 60 min at 25° C. and harvested by rapid filtration over GF/C glass fiber filters (pretreated with 0.3% polyethylenimine) followed by four washes with ice-cold buffer. Nonspecific binding was defined in the presence of 100 μM fluoxetine. IC$_{50}$ values were determined by a single site curve-fitting program (GraphPad, San Diego, Calif.) and converted to K$_i$ values based on a [$^3$H]-Citalopram K$_d$ of 0.6 nM and a ligand concentration of 0.6 nM. Data are presented in Table 1.

TABLE 1

| EX | Rat SERT K$_i$ (nM) | Human H$_3$ K$_i$ (nM) |
| --- | --- | --- |
| 1 | 1000 | 1 |
| 2 | 191 | 2 |
| 3 | 569 | 5 |
| 4 | 1667 | 1 |
| 5 | 1200 | 1 |
| 6 | 2284 | 4 |
| 7 | 583 | 4 |
| 8 | 34 | 12 |
| 9 | 43 | 3 |
| 10 | 20 | 4 |
| 11 | 53 | 43 |
| 12 | 29 | 90 |
| 13 | 179 | 1 |
| 14 | 59 | 8 |
| 15 | 20 | 5 |
| 16 | 15 | 18 |
| 17 | 312 | 2 |
| 18 | 186 | 9 |
| 19 | 56 | 208 |
| 20 | 129 | 23 |
| 21 | 15 | 7 |
| 22 | 87 | 3000 |
| 23 | 30 | 2 |
| 24 | 269 | 2 |
| 25 | 194 | 1 |
| 26 | 64 | 44 |
| 27 | 144 | 7 |
| 28 | 129 | 264 |
| 29 | 19 | 13 |
| 30 | 33 | 16 |
| 31 | 15 | 4 |
| 32 | 2000 | 2 |
| 33 | 142 | 1 |
| 34 | 186 | 2 |
| 35 | 26 | 7 |
| 36 | 22 | 15 |
| 37 | 18 | 13 |
| 38 | 56 | 50 |
| 39 | 233 | 42 |
| 40 | 45 | 13 |
| 41 | 23 | 13 |
| 42 | 106 | 3000 |
| 43 | 137 | 796 |
| 44 | 74 | 18 |
| 45 | 101 | 4 |
| 46 | 17 | 13 |
| 47 | 1000 | 11 |
| 48 | 1000 | 45 |
| 49 | 623 | 78 |
| 50 | 4 | 1 |
| 51 | 21 | 11 |

Human SERT

Homogenized HEK293 (Human Embryonic Kidney) membranes expressing the human SERT were incubated with ³H-citalopram (SERT) at rt for 1 h in 50 mM Tris, 120 mM NaCl, 5 mM KCl (pH 7.4). Nonspecific binding was determined in the presence of 10 μM fluoxetine for the SERT. The membranes were washed and the radioactivity was counted as above. Calculations for $K_i$ at the SERT were based on a $K_d$ value for ³H-citalopram and a ligand concentration of 3.1 nM. Data are presented in Table 2.

TABLE 2

| EX | Human SERT $K_i$ (nM) |
|---|---|
| 1 | 3000 |
| 2 | 768 |
| 3 | 1137 |
| 4 | 2333 |
| 5 | NT |
| 6 | 147 |
| 7 | 2000 |
| 8 | 107 |
| 9 | NT |
| 10 | NT |
| 11 | 189 |
| 12 | 70 |
| 13 | NT |
| 14 | 303 |
| 15 | 33 |
| 16 | 120 |
| 17 | 1032 |
| 18 | 362 |
| 19 | 51 |
| 20 | 226 |
| 21 | 26 |
| 22 | NT |
| 23 | 141 |
| 24 | NT |
| 25 | 1333 |
| 26 | 611 |
| 27 | 826 |
| 28 | NT |
| 29 | 66 |
| 30 | 30 |
| 31 | 93 |
| 32 | NT |
| 33 | NT |
| 34 | NT |
| 35 | 147 |
| 36 | 106 |
| 37 | 37 |
| 38 | NT |
| 39 | NT |
| 40 | 62 |
| 41 | 31 |
| 42 | NT |
| 43 | 1021 |
| 44 | 70 |
| 45 | NT |
| 46 | 16 |
| 47 | NT |
| 48 | 2000 |
| 49 | 2000 |
| 50 | 7 |
| 51 | 32 |

NT = not tested

Cyclic AMP Accumulation

Sublines of SK-N-MC cells were created that expressed a reporter construct and the human $H_3$ receptor. The reporter gene (β-galactosidase) is under the control of multiple cyclic AMP responsive elements. In 96-well plates, histamine was added directly to the cell media followed 5 min later by an addition of forskolin (5 μM final concentration). When appropriate, antagonists were added 10 min prior to agonist addition. After a 6-h incubation at 37° C., the media was aspirated and the cells washed with 200 μL of phosphate-buffered saline followed by a second aspiration. Cells were lysed with 25 μL 0.1× assay buffer (10 mM Na-phosphate, pH 8, 0.2 mM $MgSO_4$, 0.01 mM $MnCl_2$) and incubated at rt for 10 min. Cells were then incubated for 10 min with 100 μL of 1× assay buffer containing 0.5% Triton and 40 mM β-mercaptoethanol. Color was developed using 25 μL of 1 mg/mL substrate solution (chlorophenolred β-D galactopyranoside; Roche Molecular Biochemicals, Indianapolis, Ind.) Color was quantitated on a microplate reader at absorbance 570 nM. The $pA_2$ values were calculated by Schild regression analysis of the $pEC_{50}$ values and are presented in Table 3.

TABLE 3

| EX | $pA_2$ |
|---|---|
| 1 | 9.1 |
| 2 | 9.0 |
| 4 | 9.1 |
| 5 | 8.7 |
| 6 | 8.2 |
| 7 | 9.2 |
| 13 | 9.0 |
| 15 | 7.9 |
| 16 | 7.7 |
| 17 | 8.6 |
| 18 | 8.4 |
| 21 | 7.8 |
| 23 | 8.4 |
| 24 | 8.6 |
| 25 | 9.0 |
| 31 | 8.4 |
| 32 | 8.6 |
| 33 | 8.5 |
| 34 | 9.0 |
| 47 | 7.9 |

What is claimed is:

1. A compound of formula (I):

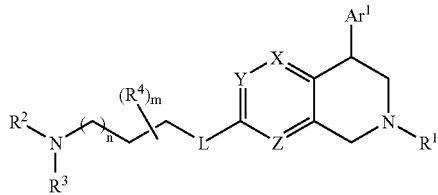

wherein
one or two of X, Y, and Z is N, and the remaining of X, Y, and Z are $CR^5$;
L is —O— or —$CH_2$— and n is 1 or 2; or L is —C≡C— and n is 0 or 1;
m is 0, 1, or 2;
$R^1$ is —H; or is —$C_{1-6}$alkyl, —$C_{3-6}$alkenyl, —$C_{3-6}$alkynyl, —$C_{3-7}$cycloalkyl, —$C_{1-6}$alkyl$C_{3-7}$cycloalkyl, —COO$C_{1-6}$alkyl, or —COObenzyl, each optionally mono-, di-, or tri-substituted with $R^a$;
$R^a$ is selected from the group consisting of —OH, —O$C_{1-6}$alkyl, phenyl optionally substituted with —O$C_{1-4}$alkyl or halo, —CN, —$NO_2$, —N($R^b$)$R^c$ (wherein $R^b$ and $R^c$ are independently —H or —$C_{1-6}$alkyl), —C(O)N($R^b$)$R^c$, —N($R^b$)C(O)$R^b$, —N($R^b$)$SO_2C_{1-6}$alkyl, —C(O)$C_{1-6}$alkyl, —S(O)$_{0-2}$—$C_{1-6}$alkyl, —$SO_2$N($R^b$)$R^c$, —$SCF_3$, halo, —$CF_3$, —$OCF_3$, —COOH, and —COO$C_{1-6}$alkyl;
$R^2$ and $R^3$ are independently selected from —H, or from the group consisting of:
A) —$C_{1-6}$alkyl, —$C_{3-6}$alkenyl, —$C_{3-6}$alkynyl, —$C_{3-7}$cycloalkyl, —$C_{1-6}$alkyl$C_{3-7}$cycloalkyl, benzyl;

B) phenyl or pyridyl, optionally fused at two adjacent carbon ring members to a three- or four-membered hydrocarbon moiety to form a fused five- or six-membered aromatic ring, which moiety has one carbon atom replaced by >O, >S, >NH, or >N($C_{1-4}$alkyl), and which moiety has up to one additional carbon atom optionally replaced by —N=;

C) a 4-8 membered heterocyclic ring, said heterocyclic ring having a carbon atom which is the point of attachment, having 1 or 2 heteroatom members selected from >O, >S(O)$_{0-2}$, and >NH, and having 0 or 1 double bonds; and D) a monocyclic aromatic hydrocarbon group having five or six ring atoms, having a carbon atom which is the point of attachment, having one carbon atom replaced by >O, >S, >NH, or >N($C_{1-4}$alkyl), having up to one additional carbon atom optionally replaced by —N=, and optionally benzofused or pyridofused;

where each of A)-D) is optionally mono-, di-, or tri-substituted with a moiety selected from the group consisting of —OH, —$C_{1-4}$alkylOH, —O$C_{1-6}$alkyl, —CN, —NO$_2$, —N($R^d$)$R^e$ (wherein $R^d$ and $R^e$ are independently —H or —$C_{1-6}$alkyl), —C(O)N($R^d$)$R^e$, —N($R^d$)C(O)$R^d$, —N($R^d$)SO$_2$$C_{1-6}$alkyl, —C(O)$C_{1-6}$alkyl, —S(O)$_{0-2}$—$C_{1-6}$alkyl, —SO$_2$N($R^d$)$R^e$, —SCF$_3$, halo, —CF$_3$, —OCF$_3$, —COOH, —COO$C_{1-6}$alkyl, —OC(O)N($R^d$)$R^e$, and —OC(O)O$R^d$;

or, alternatively, $R^2$ and $R^3$ may be taken together with the nitrogen to which they are attached to form a 4-8 membered heterocyclic ring, said heterocyclic ring having 0 or 1 additional heteroatom members separated from the nitrogen of attachment by at least one carbon member and selected from >O, >S(O)$_{0-2}$, >NH, and >N$R^f$, having 0 or 1 double bonds, having 0, 1, or 2 carbon members separated from the nitrogen of attachment by at least one carbon member which is a carbonyl, optionally benzo or pyrido fused, optionally having one carbon member that forms a bridge, and having 0-5 carbon member substituents $R^{ff}$, $R^f$ is selected from the group consisting of —$C_{1-6}$alkyl optionally mono-, di-, or tri-substituted with halo, —$C_{3-6}$alkenyl, —$C_{3-6}$alkynyl, —$C_{3-7}$cycloalkyl, —$C_{1-6}$alkyl$C_{3-7}$cycloalkyl, —$C_{2-6}$alkylOH, —C(O)N($R^g$)$R^h$ (wherein $R^g$ and $R^h$ are independently —H or —$C_{1-6}$alkyl), —C(O)$R^i$ (where $R^i$ is —$C_{1-6}$alkyl, —$C_{3-8}$cycloalkyl, phenyl, or 5- or 6-membered aromatic heterocyclyl, each optionally mono-, di-, or tri-substituted with —$C_{1-3}$alkyl, —OH, —O$C_{1-6}$alkyl, —CF$_3$, or halo), —S(O)$_{0-2}$—$C_{1-6}$alkyl, and —COO$C_{1-6}$alkyl;

$R^{ff}$ is selected from the group consisting of —$C_{1-6}$alkyl optionally mono-, di-, or tri-substituted with halo, —$C_{2-6}$alkenyl, —$C_{2-6}$alkynyl, —$C_{3-7}$cycloalkyl, —$C_{1-6}$alkyl$C_{3-7}$cycloalkyl, halo, —OH, —$C_{1-6}$alkylOH, —O$C_{1-6}$alkyl, —O$C_{2-3}$alkylO—, —CN, —NO$_2$, —N($R^g$)$R^h$ (wherein $R^g$ and $R^h$ are independently —H or —$C_{1-6}$alkyl), —C(O)N($R^g$)$R^h$, —N($R^g$)C(O)$R^g$, —N($R^g$)SO$_2$$C_{1-6}$alkyl, —C(O)$R^i$ (where $R^i$ is —$C_{1-6}$alkyl, —$C_{3-8}$cycloalkyl, phenyl, or 5- or 6-membered aromatic heterocyclyl, each optionally mono-, di-, or tri-substituted with —$C_{1-3}$alkyl, —OH, —O$C_{1-6}$alkyl, —CF$_3$, or halo), —S(O)$_{0-2}$—$C_{1-6}$alkyl, —SO$_2$N($R^y$)$R^z$, —SCF$_3$, —OCF$_3$, —COOH, and —COO$C_{1-6}$alkyl;

$R^4$ is —OH, —O$C_{1-6}$alkyl, —CF$_3$, —$C_{1-6}$alkyl, or halo; two $R^4$ substituents may be taken together to form methylene or ethylene; or one of $R^4$ is taken together with $R^2$ to form methylene, ethylene, or propylene; wherein each methylene, ethylene, or propylene is optionally substituted with —OH, —O$C_{1-6}$alkyl, —S$C_{1-6}$alkyl, —CF$_3$, —$C_{1-6}$alkyl, amino, or halo;

$R^5$ is selected from the group consisting of —H, —$C_{1-6}$alkyl, —OH, —O$C_{1-6}$alkyl, —S$C_{1-6}$alkyl, and halo;

$Ar^1$ is an aryl or heteroaryl ring selected from the group consisting of:

a) phenyl, optionally mono-, di-, or tri-substituted with $R^j$ or di-substituted on adjacent carbons with —O$C_{1-4}$alkyleneO- optionally mono- or di-substituted with fluoro, —(CH$_2$)$_{2-3}$NH—, —(CH$_2$)$_{1-2}$NH(CH$_2$)—, —(CH$_2$)$_{2-3}$N($C_{1-4}$alkyl)-, or —(CH$_2$)$_{1-2}$N($C_{1-4}$alkyl)(CH$_2$)—;

$R^j$ is selected from the group consisting of

1) —OH, —$C_{1-6}$alkyl, —O$C_{1-6}$alkyl optionally mono-, di-, or tri-substituted with halo, —$C_{2-6}$alkenyl, —O$C_{3-6}$alkenyl, —$C_{2-6}$alkynyl, —O$C_{3-6}$alkynyl, —$C_{3-6}$cycloalkyl, —O$C_{3-6}$cycloalkyl, —CN, —NO$_2$, —N($R^k$)$R^l$ (wherein $R^k$ and $R^l$ are independently —H or —$C_{1-6}$alkyl), —N($R^k$)COR$^l$, —N($R^k$)SO$_2$$C_{1-6}$alkyl, —C(O)$C_{1-6}$alkyl, —S(O)$_{0-2}$—$C_{1-6}$alkyl, —C(O)N($R^m$)$R^n$ (wherein $R^m$ and $R^n$ are independently —H or —$C_{1-6}$alkyl, or $R^m$ and $R^n$ taken together with their nitrogen of attachment form a 4-8 membered heterocyclic ring having 1 or 2 heteroatom members selected from >O, >S(O)$_{0-2}$, >NH, and >N$C_{1-6}$alkyl, having 0 or 1 double bonds, having 0 or 1 carbonyl members), —SO$_2$N($R^m$)$R^n$, —SCF$_3$, halo, —CF$_3$, —COOH, —COO$C_{1-6}$alkyl, and —COO$C_{3-7}$cycloalkyl; and 2) a 4-8 membered saturated or partially saturated heterocyclic ring, having 1 or 2 heteroatom members selected from >O, >S(O)$_{0-2}$, >NH, and >N$C_{1-6}$alkyl, having 0 or 1 carbonyl members; said ring optionally mono-, di-, or tri-substituted with $R^p$;

$R^p$ is a substituent independently selected from the group consisting of —OH, —$C_{1-6}$alkyl, —O$C_{1-6}$alkyl, phenyl, —CN, —NO$_2$, —N($R^q$)$R^r$ (wherein $R^q$ and $R^r$ are independently —H, —$C_{1-6}$alkyl, or —$C_{2-6}$alkenyl), —C(O)N($R^q$)$R^r$, —N($R^q$)C(O)$R^r$, —N($R^q$)SO$_2$$C_{1-6}$alkyl, —C(O)$C_{1-6}$alkyl, —S(O)$_{0-2}$—$C_{1-6}$alkyl, —SO$_2$N($R^q$)$R^r$, —SCF$_3$, halo, —CF$_3$, —OCF$_3$, —OCHF$_2$, —COOH, and —COO$C_{1-6}$alkyl;

b) phenyl or pyridyl fused at two adjacent carbon ring members to a three membered hydrocarbon moiety to form a fused five membered aromatic ring, which moiety has one carbon atom replaced by >O, >S, >NH, or >N($C_{1-4}$alkyl), and which moiety has up to one additional carbon atom optionally replaced by —N=, the fused rings optionally mono-, di-, or tri-substituted with $R^t$;

$R^t$ is a substituent independently selected from the group consisting of —OH, —$C_{1-6}$alkyl, —O$C_{1-6}$alkyl, phenyl, —CN, —NO$_2$, —N($R^u$)$R^v$ (wherein $R^u$ and $R^v$ are independently —H or —$C_{1-6}$alkyl), —C(O)N($R^u$)$R^v$, —N($R^u$)C(O)$R^v$, —N($R^u$)SO$_2$$C_{1-6}$alkyl, —C(O)$C_{1-6}$alkyl, —S(O)$_{0-2}$—$C_{1-6}$alkyl, —SO$_2$N($R^u$)$R^v$, —SCF$_3$, halo, —CF$_3$, —OCF$_3$, —OCHF$_2$, —COOH, and —COO$C_{1-6}$alkyl;

c) phenyl fused at two adjacent ring members to a four membered hydrocarbon moiety to form a fused six membered aromatic ring, which moiety has 0, 1, or 2 carbon atoms replaced by —N═, the fused rings optionally mono-, di-, or tri-substituted with $R^t$;

d) a monocyclic aromatic hydrocarbon group having five ring atoms, having a carbon atom which is the point of attachment, having one carbon atom replaced by >O, >S, >NH, or >N($C_{1-4}$alkyl), having up to one additional carbon atom optionally replaced by —N═, optionally mono- or di-substituted with $R^t$, and optionally benzofused or pyridofused at two adjacent carbon atoms, where the benzofused or pyridofused moiety is optionally mono-, di-, or tri-substituted with $R^t$; and e) a monocyclic aromatic hydrocarbon group having six ring atoms, having a carbon atom which is the point of attachment, having one or two carbon atoms replaced by —N═, optionally mono- or di-substituted with $R^t$, and optionally benzofused or pyridofused at two adjacent carbon atoms, where the benzofused or pyridofused moiety is optionally mono- or di-substituted with $R^t$;

and enantiomers, diastereomers, hydrates, solvates thereof, and pharmaceutically acceptable salts, esters and amides thereof.

2. The compound of claim 1 wherein X is N.

3. The compound of claim 1 wherein Y is N.

4. The compound of claim 1 wherein Z is N.

5. The compound of claim 1 wherein Y and Z are N.

6. The compound of claim 1 wherein L is —O— and n is 1.

7. The compound of claim 1 wherein L is —$CH_2$— and n is 1.

8. The compound of claim 1 wherein L is —C≡C— and n is 0.

9. The compound of claim 1 wherein m is 0 or 1.

10. The compound of claim 1 wherein $R^1$ is selected from the group consisting of hydrogen, methyl, ethyl, propyl, isopropyl, butyl, pentyl, hexyl, benzyl, allyl, propargyl, cyclopropyl, cyclobutyl, cyclopentyl, cyclohexyl, cyclopropylmethyl, —$COOCH_3$, —COO-t-butyl, and —COObenzyl.

11. The compound of claim 1 wherein $R^1$ is methyl, ethyl, propyl, allyl, propargyl, or benzyl.

12. The compound of claim 1 wherein $R^1$ is hydrogen or methyl.

13. The compound of claim 1 wherein $R^2$ and $R^3$ are independently selected from —H, or, optionally substituted, from the group consisting of:

A) methyl, ethyl, isopropyl, butyl, pentyl, hexyl, allyl, propargyl, cyclopropyl, cyclobutyl, cyclopentyl, cyclohexyl, cyclopropylmethyl, benzyl, B) phenyl, pyridyl, 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5,6,7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl, C) azetidinyl, pyrrolidinyl, piperidinyl, and D) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, and 3-indazolyl.

14. The compound of claim 1 wherein $R^2$ and $R^3$, optionally substituted, are independently selected from methyl, ethyl, isopropyl, pyrrolidinyl, piperidinyl, 2-benzothiazolyl, and methoxyethyl.

15. The compound of claim 1 wherein $R^2$ and $R^3$ are, independently, ethyl, isopropyl, methoxyethyl, or 2-benzothiazolyl.

16. The compound of claim 1 wherein $R^2$ and $R^3$, optionally substituted, are taken together with the nitrogen to which they are attached to form a ring selected from the group consisting of azetidinyl, pyrrolidinyl, piperidinyl, morpholinyl, thiomorpholinyl, piperazinyl, homopiperidinyl, 1,3-dihydro-isoindol-2-yl, 5,6-dihydro-4H-pyrimidin-1-yl, and 1,1-dioxo-$1\lambda^6$-thiomorpholin-4-yl.

17. The compound of claim 1 wherein $R^2$ and $R^3$ are taken together with the nitrogen to which they are attached to form a 4-8 membered heterocyclic ring, said heterocyclic ring selected from piperidine, pyrrolidine, and morpholine, said ring substituted with 1 or 2 substituents $R^f$.

18. The compound of claim 1 wherein $R^f$ is selected from the group consisting of methyl, ethyl, isopropyl, butyl, hexyl, —$CF_3$, —$CHF_2$, vinyl, allyl, propargyl, cyclopropyl, cyclopentyl, cyclopropylmethyl, cyclobutylethyl, bromo, chloro, fluoro, iodo, —OH, hydroxymethyl, hydroxyethyl, methoxy, ethoxy, isopropoxy, pentyloxy, —O($CH_2)_2$O—, —O($CH_2)_3$O—, —CN, amino, methylamino, dimethylamino, diethylamino, diethylcarbamoyl, methanesulfanyl, methanesulfonyl, methanesulfonamido, —C(O)$R^t$, —COOH, and ethoxycarbonyl.

19. The compound of claim 1 wherein $R^f$ is selected from the group consisting of methyl, fluoro, —OH, —$CF_3$, hydroxymethyl, hydroxyethyl, dimethylamino, ethoxycarbonyl, and —O($CH_2)_2$O—.

20. The compound of claim 1 wherein $R^t$ is selected from the group consisting of methyl, pyridyl, isopropyl, cyclobutyl, cyclopropyl, N-methylpyrrolyl, and 1-methyl imidazolyl.

21. The compound of claim 1 wherein $R^2$ and $R^3$ are taken together with the nitrogen to which they are attached to form azetidinyl, 2-methylpyrrolidinyl, 3-hydroxypyrrolidinyl, 3-dimethylaminopyrrolidinyl, 2,5-dimethylpyrrolidinyl, 2-trifluoromethylpyrrolidinyl, 2-hydroxymethylpyrrolidinyl, piperidinyl, 4-fluoropiperidinyl, 3,3-difluoropiperidinyl, 4,4-difluoropiperidinyl, 3-trifluoromethylpiperidinyl, 4-trifluoromethylpiperidinyl, 1,4-dioxa-8-aza-spiro[4.5]dec-8-yl, morpholinyl, 4-cyanopiperidinyl, 4-carboethoxypiperidinyl, 3-hydroxypiperidinyl, 4-hydroxypiperidinyl, 2-hydroxymethylpiperidinyl, 3-hydroxymethylpiperidinyl, 4-hydroxymethylpiperidinyl, 4-hydroxyethylpiperidinyl, 3-methylmorpholin-4-yl, 3-hydroxymethylmorpholin-4-yl, 2-hydroxymethylmorpholin-4-yl, 2,6-dimethylmorpholin-4-yl, 1,3-dihydro-isoindol-2-yl, 5,6-dihydro-4H-pyrimidin-1-yl, 1,1-dioxo-$1\lambda^6$-thiomorpholin-4-yl, or 2-methylmorpholin-4-yl.

22. The compound of claim 1 wherein $R^2$ and $R^3$ are taken together with the nitrogen to which they are attached to form piperidinyl, 4-fluoropiperidinyl, 4,4-difluoropiperidinyl, morpholinyl, or 3-methylmorpholin-4-yl.

23. The compound of claim 1 wherein $R^4$ is methoxy, ethoxy, isopropoxy, pentyloxy, —$CF_3$, methyl, ethyl, propyl, isobutyl, pentyl, chloro, or fluoro.

24. The compound of claim 1 wherein $R^4$ is hydroxy, methyl, methoxy, fluoro, or —$CF_3$.

25. The compound of claim 1 wherein two $R^4$ are taken together to form methylene.

26. The compound of claim 1 wherein $R^2$ and one of $R^4$ are taken together to form ethylene or propylene.

27. The compound of claim 1 wherein $R^5$ is hydrogen, methyl, ethyl, isopropyl, hexyl, hydroxyl, methoxy, ethoxy, isopropoxy, methylsulfanyl, bromo, chloro, fluoro, or iodo.

28. The compound of claim 1 wherein $R^5$ is hydrogen.

29. The compound of claim 1 wherein $Ar^1$, optionally substituted, is selected from the group consisting of:
   a) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl,
   b) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl,
   c) naphthyl, 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl,
   d) furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, 3-indazolyl, and
   e) pyridinyl, pyridinyl-N-oxide, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl, [1,5], [1,6], [1,7], or [1,8]naphthyridin-2-, 3-, or 4-yl, [2,5], [2,6], [2,7], [2,8]naphthyridin-1-, 3-, or 4-yl.

30. The compound of claim 1 wherein $Ar^1$, optionally substituted, is selected from the group consisting of phenyl, pyridyl, pyrazinyl, thiazolyl, pyrazolyl, and thiophenyl.

31. The compound of claim 1 wherein $Ar^1$ is selected from the group consisting of phenyl, 2-methoxyphenyl, 3-methoxyphenyl, 4-methoxyphenyl, 2,4-dimethoxyphenyl, 2,5-dimethoxyphenyl, 3,4-dimethoxyphenyl, 3,5-dimethoxyphenyl, 3,4,5-trimethoxyphenyl, 2-methylphenyl, 3-methylphenyl, 4-methylphenyl, 4-ethylphenyl, 3-ethynylphenyl, 4-ethynylphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 3-iodophenyl, 4-iodophenyl, 2-trifluoromethylphenyl, 3-trifluoromethylphenyl, 4-trifluoromethylphenyl, 3-trifluoromethoxyphenyl, 4-trifluoromethoxyphenyl, 4-difluoromethoxyphenyl, 3-cyanophenyl, 4-cyanophenyl, 3-acetylphenyl, 4-acetylphenyl, 3,4-difluorophenyl, 3,4-dichlorophenyl, 2,3-difluorophenyl, 2,3-dichlorophenyl, 2,4-difluorophenyl, 2,4-dichlorophenyl, 2,5-dichlorophenyl, 3,5-dichlorophenyl, 3-nitrophenyl, 4-nitrophenyl, 3-chloro-4-fluorophenyl, 3-chloro-4-methoxyphenyl, 3-chloro-4-difluoromethoxyphenyl, 3-fluoro-4-chlorophenyl, benzo[1,3]dioxol-4 or 5-yl, 2-hydroxyphenyl, 3-hydroxyphenyl, 4-hydroxyphenyl, 4-hydroxy-2-methylphenyl, 4-hydroxy-3-fluorophenyl, 3,4-dihydroxyphenyl, 4-aminophenyl, 4-dimethylaminophenyl, 4-carbamoylphenyl, 4-fluoro-3-methylphenyl, 4-methanesulfanylphenyl, 4-methanesulfinylphenyl, 4-methanesulfonylphenyl, 4-trifluoromethanesulfanylphenyl, thiophen-2-yl, thiophen-3-yl, 2-pyridinyl, 3-pyridinyl, 4-pyridinyl, 2-chloro-5-pyridinyl, 2-dimethylamino-5-pyridinyl, 2-methoxy-5-pyridinyl, 2-thiomethyl-5-pyridinyl, 2-hydroxy-5-pyridinyl, oxazol-5-yl, thiazol-5-yl, thiazol-2-yl, 2H-pyrazol-3-yl, pyrazin-2-yl, 1-naphthyl, 2-naphthyl, 4-imidazol-1-ylphenyl, 4-pyrazol-1-ylphenyl, 1H-indol-5-yl, 1H-benzimidazol-5-yl, benzo[b]thiophen-7-yl, and 4-biphenyl.

32. The compound of claim 1 wherein $Ar^1$, optionally substituted with halo, is 4-methoxyphenyl or 4-methanesulfanylphenyl.

33. A compound selected from the group consisting of:
   4-(2-Fluoro-phenyl)-7-(3-piperidin-1-yl-propoxy)-1,2,3,4-tetrahydro-[2,6]naphthyridine;
   4-(2-Fluoro-phenyl)-2-methyl-7-(3-piperidin-1-yl-propoxy)-1,2,3,4-tetrahydro-[2,6]-naphthyridine;
   2-Methyl-4-phenyl-7-(3-piperidin-1-yl-propoxy)-1,2,3,4-tetrahydro-[2,6]-naphthyridine;
   4-Phenyl-7-(3-piperidin-1-yl-propoxy)-1,2,3,4-tetrahydro-[2,6]naphthyridine;
   Diethyl-[3-(8-phenyl-5,6,7,8-tetrahydro-[2,6]naphthyridin-3-yloxy)-propyl]-amine;
   4-(4-Methoxy-phenyl)-7-(3-piperidin-1-yl-propoxy)-1,2,3,4-tetrahydro-[2,6]-naphthyridine;
   Diethyl-[3-(6-methyl-8-phenyl-5,6,7,8-tetrahydro-[2,6]naphthyridin-3-yloxy)-propyl]-amine;
   4-(4-Methoxy-phenyl)-2-methyl-7-(3-piperidin-1-yl-propoxy)-1,2,3,4-tetrahydro-[2,6]-naphthyridine;
   4-(4-Methoxy-phenyl)-7-[2-(1-methyl-pyrrolidin-2-yl)-ethoxy]-1,2,3,4-tetrahydro-[2,6]-naphthyridine;
   4-(4-Methoxy-phenyl)-2-methyl-7-[2-(1-methyl-pyrrolidin-2-yl)-ethoxy]-1,2,3,4-tetrahydro-[2,6]-naphthyridine;
   4-(4-Methoxy-phenyl)-7-(3-morpholin-4-yl-propoxy)-1,2,3,4-tetrahydro-[2,6]-naphthyridine;
   4-(4-Methoxy-phenyl)-2-methyl-7-(3-morpholin-4-yl-propoxy)-1,2,3,4-tetrahydro-[2,6]-naphthyridine;
   4-(3-Methoxy-phenyl)-7-(3-piperidin-1-yl-propoxy)-1,2,3,4-tetrahydro-[2,6]-naphthyridine;
   4-(3-Methoxy-phenyl)-2-methyl-7-(3-piperidin-1-yl-propoxy)-1,2,3,4-tetrahydro-[2,6]-naphthyridine;
   4-(3,4-Dichloro-phenyl)-7-(3-piperidin-1-yl-propoxy)-1,2,3,4-tetrahydro-[2,6]-naphthyridine;
   4-(3,4-Dichloro-phenyl)-2-methyl-7-(3-piperid in-1-yl-propoxy)-1,2,3,4-tetrahydro-[2,6]-naphthyridine;
   4-(4-Fluoro-phenyl)-7-(3-piperidin-1-yl-propoxy)-1,2,3,4-tetrahydro-[2,6]naphthyridine;
   4-(4-Fluoro-phenyl)-2-methyl-7-(3-piperidin-1-yl-propoxy)-1,2,3,4-tetrahydro-[2,6]-naphthyridine;
   7-[3-(4,4-Difluoro-piperidin-1-yl)-propoxy]-4-(4-methoxy-phenyl)-1,2,3,4-tetrahydro-[2,6]-naphthyridine;
   Diethyl-{3-[8-(4-methoxy-phenyl)-5,6,7,8-tetrahydro-[2,6]naphthyridin-3-yloxy]-propyl}-amine;
   {3-[8-(3,4-Dichloro-phenyl)-5,6,7,8-tetrahydro-[2,6]naphthyridin-3-yloxy]-propyl}-diethyl-amine;
   7-(1-Benzyl-piperidin-4-yloxy)-4-(4-methoxy-phenyl)-1,2,3,4-tetrahydro-[2,6]-naphthyridine;
   4-(4-Chloro-phenyl)-7-(3-piperidin-1-yl-propoxy)-1,2,3,4-tetrahydro-[2,6]naphthyridine;
   4-(3-Chloro-phenyl)-7-(3-piperidin-1-yl-propoxy)-1,2,3,4-tetrahydro-[2,6]naphthyridine;
   4-(2-Chloro-phenyl)-7-(3-piperidin-1-yl-propoxy)-1,2,3,4-tetrahydro-[2,6]naphthyridine;
   4-(3,4-Dichloro-phenyl)-7-(3-morpholin-4-yl-propoxy)-1,2,3,4-tetrahydro-[2,6]-naphthyridine;
   4-(3-Chloro-phenyl)-2-methyl-7-(3-piperidin-1-yl-propoxy)-1,2,3,4-tetrahydro-[2,6]-naphthyridine;
   7-[3-(4,4-Difluoro-piperidin-1-yl)-propoxy]-4-(4-methoxy-phenyl)-2-methyl-1,2,3,4-tetrahydro-[2,6]naphthyridine;
   Diethyl-{3-[8-(4-methoxy-phenyl)-6-methyl-5,6,7,8-tetrahydro-[2,6]naphthyridin-3-yloxy]-propyl}-amine;

{3-[8-(3,4-Dichloro-phenyl)-6-methyl-5,6,7,8-tetrahydro-[2,6]naphthyridin-3-yloxy]-propyl}-diethylamine;

7-(1-Isopropyl-piperidin-4-ylmethoxy)-4-(4-methoxyphenyl)-1,2,3,4-tetrahydro-[2,6]-naphthyridine;

4-(3-Fluoro-phenyl)-7-(3-piperidin-1-yl-propoxy)-1,2,3,4-tetrahydro-[2,6]naphthyridine;

4-(3-Chloro-4-fluoro-phenyl)-7-(3-piperidin-1-yl-propoxy)-1,2,3,4-tetrahydro-[2,6]naphthyridine;

4-(3-Fluoro-phenyl)-2-methyl-7-(3-piperidin-1-yl-propoxy)-1,2,3,4-tetrahydro-[2,6]-naphthyridine;

4-(3-Chloro-4-fluoro-phenyl)-2-methyl-7-(3-piperid in-1-yl-propoxy)-1,2,3,4-tetrahydro-[2,6]naphthyridine;

4-(4-Chloro-phenyl)-2-methyl-7-(3-piperidin-1-yl-propoxy)-1,2,3,4-tetrahydro-[2,6]naphthyridine;

4-(3,4-Dichloro-phenyl)-7-(1-isopropyl-piperidin-4-ylmethoxy)-1,2,3,4-tetrahydro-[2,6]naphthyridine;

4-(3,4-Dichloro-phenyl)-2-methyl-7-(3-piperidin-1-yl-propoxy)-1,2,3,4-tetrahydro-[2,6]-naphthyridine (enantiomer A);

4-(3,4-Dichloro-phenyl)-2-methyl-7-(3-piperidin-1-yl-propoxy)-1,2,3,4-tetrahydro-[2,6]-naphthyridine (enantiomer B);

7-(1-Isopropyl-piperidin-4-ylmethoxy)-4-(4-methoxyphenyl)-2-methyl-1,2,3,4-tetrahydro-[2,6]-naphthyridine;

4-(3,4-Dichloro-phenyl)-7-(1-isopropyl-piperidin-4-ylmethoxy)-2-methyl-1,2,3,4-tetrahydro-[2,6]naphthyridine;

4-(4-Methoxy-phenyl)-7-(piperidin-4-yloxy)-1,2,3,4-tetrahydro-[2,6]naphthyridine;

4-(4-Methoxy-phenyl)-2-methyl-7-(1-methyl-piperidin-4-yloxy)-1,2,3,4-tetrahydro-[2,6]naphthyridine;

7-(3-Piperidin-1-yl-propoxy)-4-(4-trifluoromethoxy-phenyl)-1,2,3,4-tetrahydro-[2,6]naphthyridine;

4-(3,4-Dichloro-phenyl)-7-(3-piperidin-1-yl-propoxy)-1,2,3,4-tetrahydro-[2,6]-naphthyridine (enantiomer A);

4-(3,4-Dichloro-phenyl)-7-(3-piperidin-1-yl-propoxy)-1,2,3,4-tetrahydro-[2,6]-naphthyridine (enantiomer B);

7-(3-Morpholin-4-yl-propoxy)-4-phenyl-1,2,3,4-tetrahydro-[2,6]naphthyridine;

8-(4-Methoxy-phenyl)-6-methyl-3-(4-piperidin-1-yl-but-1-ynyl)-5,6,7,8-tetrahydro-[1,6]naphthyridine;

8-(4-Methoxy-phenyl)-6-methyl-3-(4-piperidin-1-yl-butyl)-5,6,7,8-tetrahydro-[1,6]-naphthyridine;

5-(4-Methoxy-phenyl)-7-methyl-2-(3-piperidin-1-yl-propoxy)-5,6,7,8-tetrahydro-[1,7]naphthyridine; and 5-(4-Methoxy-phenyl)-7-methyl-2-(4-piperidin-1-yl-but-1-ynyl)-5,6,7,8-tetrahydro-[1,7]naphthyridine.

34. A pharmaceutical composition comprising a pharmaceutically acceptable carrier and an effective amount of at least one compound of formula (I).

* * * * *